US012636381B2

(12) United States Patent
Musunuru et al.

(10) Patent No.: US 12,636,381 B2
(45) Date of Patent: May 26, 2026

(54) IN UTERO CRISPR-MEDIATED THERAPEUTIC EDITING OF GENES

(71) Applicants: THE TRUSTEES OF THE UNIVERSITY OF PENNSYLVANIA, Philadelphia, PA (US); THE CHILDREN'S HOSPITAL OF PHILADELPHIA, Philadelphia, PA (US)

(72) Inventors: Kiran Musunuru, Philadelphia, PA (US); William H. Peranteau, Philadelphia, PA (US); Edward Morrisey, Newton Square, PA (US)

(73) Assignees: THE TRUSTEES OF THE UNIVERSITY OF PENNSYLVANIA, Philadelphia, PA (US); THE CHILDREN'S HOSPITAL OF PHILADELPHIA, Philadelphia, PA (US)

( * ) Notice: Subject to any disclaimer, the term of this patent is extended or adjusted under 35 U.S.C. 154(b) by 1368 days.

(21) Appl. No.: 17/052,170

(22) PCT Filed: Apr. 30, 2019

(86) PCT No.: PCT/US2019/030083
§ 371 (c)(1),
(2) Date: Oct. 30, 2020

(87) PCT Pub. No.: WO2019/213183
PCT Pub. Date: Nov. 7, 2019

(65) Prior Publication Data
US 2024/0075164 A1      Mar. 7, 2024

Related U.S. Application Data

(60) Provisional application No. 62/664,904, filed on Apr. 30, 2018.

(51) Int. Cl.
| | |
|---|---|
| *A61K 48/00* | (2006.01) |
| *A61P 3/00* | (2006.01) |
| *C12N 9/02* | (2006.01) |
| *C12N 9/22* | (2006.01) |
| *C12N 15/113* | (2010.01) |
| *C12N 15/86* | (2006.01) |

(52) U.S. Cl.
CPC ............. *A61K 48/005* (2013.01); *A61P 3/00* (2018.01); *C12N 9/0069* (2013.01); *C12N 9/22* (2013.01); *C12N 15/113* (2013.01); *C12N 15/86* (2013.01); *C12N 2310/11* (2013.01); *C12N 2310/20* (2017.05); *C12N 2710/10343* (2013.01); *C12N 2750/14143* (2013.01); *C12Y 113/11027* (2013.01)

(58) Field of Classification Search
CPC ....... A61K 48/005; A61P 3/00; C12N 9/0069; C12N 9/22; C12N 15/113; C12N 15/86; C12N 2310/11; C12N 2310/20; C12N 2710/10343; C12N 2750/14143; C12N 9/6424; C12Y 113/11027
See application file for complete search history.

(56) References Cited

U.S. PATENT DOCUMENTS

| | | | |
|---|---|---|---|
| 4,186,183 A | 1/1980 | Steck et al. |
| 4,217,344 A | 8/1980 | Vanlerberghe et al. |
| 4,235,871 A | 11/1980 | Papahadjopoulos et al. |
| 4,261,975 A | 4/1981 | Fullerton et al. |
| 4,485,054 A | 11/1984 | Mezei et al. |
| 4,501,728 A | 2/1985 | Geho et al. |
| 4,774,085 A | 9/1988 | Fidler |
| 4,797,368 A | 1/1989 | Carter et al. |
| 4,837,028 A | 6/1989 | Allen |
| 4,873,316 A | 10/1989 | Meade et al. |
| 4,897,355 A | 1/1990 | Eppstein et al. |
| 4,946,787 A | 8/1990 | Eppstein et al. |
| 5,049,386 A | 9/1991 | Eppstein et al. |
| 5,173,414 A | 12/1992 | Lebkowski et al. |

(Continued)

FOREIGN PATENT DOCUMENTS

| | | |
|---|---|---|
| WO | 1991/016024 A1 | 10/1991 |
| WO | 1991/017424 A1 | 11/1991 |

(Continued)

OTHER PUBLICATIONS

Chadwick AC, Wang X, Musunuru K. In Vivo Base Editing of PCSK9 (Proprotein Convertase Subtilisin/Kexin Type 9) as a Therapeutic Alternative to Genome Editing. Arterioscler Thromb Vasc Biol. Sep. 2017;37(9):1741-1747. doi: 10.1161/ATVBAHA.117. 309881. Epub Jul. 27, 2017. PMID: 28751571; PMCID: PMC5570639. (Year: 2017).*

(Continued)

*Primary Examiner* — Brian Whiteman
*Assistant Examiner* — Amanda M Zahorik
(74) *Attorney, Agent, or Firm* — Howson & Howson, LLP; Kathleen D. Rigaut; Richard F. Kane

(57) ABSTRACT

A method for in utero genome editing, the method comprising administering to a subject an adenoviral vector, wherein the subject is a fetus, the adenoviral vector comprising CRISPR-mediated base editor and a guide RNA (gRNA), the gRNA targeting a mutation in a therapeutic gene; and introducing a modified codon in the therapeutic gene by base editing the therapeutic gene, wherein the gene editing is performed by the adenoviral vector, an adeno-associated viral vector or lipid based nanoparticle.

16 Claims, 47 Drawing Sheets
Specification includes a Sequence Listing.

(56)                    References Cited

U.S. PATENT DOCUMENTS

| | | |
|---|---|---|
| 2011/0059502 A1 | 3/2011 | Chalasani |
| 2016/0145646 A1 | 5/2016 | Frendewey et al. |
| 2016/0346362 A1 | 12/2016 | Quake et al. |

FOREIGN PATENT DOCUMENTS

| | | |
|---|---|---|
| WO | 1993/024641 A2 | 12/1993 |
| WO | WO-2017201258 A1 * | 11/2017 ......... A61K 31/7105 |

OTHER PUBLICATIONS

Pierre Billon, Eric E. Bryant, Sarah A. Joseph, Tarun S. Nambiar, Samuel B. Hayward, Rodney Rothstein, Alberto Ciccia, CRISPR-Mediated Base Editing Enables Efficient Disruption of Eukaryotic Genes through Induction of Stop Codons, Molecular Cell, vol. 67, Issue 6, 2017, pp. 1068-1079.e4 (Year: 2017).*

Komor, A., Kim, Y., Packer, M. et al. Programmable editing of a target base in genomic DNA without double-stranded DNA cleavage. Nature 533, 420-424 (2016). https://doi.org/10.1038/nature17946 (Year: 2016).*

Lipshutz, Gerald S., Linda Flebbe-Rehwaldt, and Karin ML Gaensler. "Reexpression following readministration of an adenoviral vector in adult mice after initial in utero adenoviral administration." Molecular Therapy 2.4 (2000): 374-380. (Year: 2000).*

Pankowicz FP, Barzi M, Legras X, Hubert L, Mi T, Tomolonis JA, Ravishankar M, Sun Q, Yang D, Borowiak M, Sumazin P, Elsea SH, Bissig-Choisat B, Bissig KD. Reprogramming metabolic pathways in vivo with CRISPR/Cas9 genome editing to treat hereditary tyrosinaemia. Nat Commun. Aug. 30, 2016;7:12642. (Year: 2016).*

NCBI Reference Sequence: NM_008277.3, Mus musculus 4-hydroxyphenylpyruvic acid dioxygenase (Hpd), mRNA, Oct. 7, 2017 revision (Year: 2017).*

Waddington et al. In Utero gene therapy: current challenges and perspectives. Molecular Therapy. vol. 11, Issue 5, p. 661-676. May 2005. (Year: 2005).*

Billon et al. Mol Cell . Sep. 21, 2017;67(6):1068-1079.e4. doi: 10.1016/j.molcel.2017.08.008. Epub Sep. 7, 2017. (Year: 2017).*

Komor AC, Zhao KT, Packer MS, Gaudelli NM, Waterbury AL, Koblan LW, Kim YB, Badran AH, Liu DR. Improved base excision repair inhibition and bacteriophage Mu Gam protein yields C:G-to-T:A base editors with higher efficiency and product purity. Sci Adv. Aug. 30, 2017;3(8):eaao4774. (Year: 2017).*

Jia et al. Multiple sgRNAs facilitate base editing-mediated i-stop to induce complete and precise gene disruption. Protein Cell 2019, 10(11):832-839. (Year: 2019).*

International Search Report and Written Opinion, dated Sep. 19, 2019, issued in corresponding International Application No. PCT/US2019/030083, filed Apr. 30, 2019.

Chadwick, Alexandra C. et al., "In Vivo Base Editing of PCSK9 (Proprotein Convertase Subtilisin/Kexin Type 9) as a Therapeutic Alternative to Genome Editing," Arteriosclerosis, Thrombosis, and Vascular Biology, vol. 37, No. 9, Sep. 2017, pp. 1741-1747.

Carreras, Alba et al., "In vivo genome and base editing of a human PCSK9 knock-in hypercholesterolemic mouse model," BMC Biology, vol. 17, No. 4, Dec. 2019, pp. 1-14.

Kaufman, R.J. et al., "Translational efficiency of polycistronic mRNAs and their utilization to express heterologous genes in mammalian cells," The EMBO Journal, vol. 6, No. 1, Jan. 1987, pp. 187-193.

Pinkert, Carl A. et al., "An albumin enhancer located 10 kb upstream functions along with its promoter to direct efficient, liver-specific expression in transgenic mice," Genes & Development, vol. 1, 1987, pp. 268-276.

Calame, Kathryn et al., "Transcriptional Controlling Elements in the Immunoglobulin and T Cell Receptor Loci," Advances in Immunology, vol. 43, 1988, pp. 235-275.

Winoto, Astar et al., "A novel, inducible and T cell-specific enhancer located at the 3' end of the T cell receptor α locus," The EMBO Journal, vol. 8, No. 3, Mar. 1989, pp. 729-733.

Banerji, J. et al., "A lymphocyte-specific cellular enhancer is located downstream of the joining region in immunoglobulin heavy chain genes," Cell, vol. 33, No. 3, Jul. 1983, pp. pp. 729-740.

Queen, C. et al., "Immunoglobulin gene transcription is activated by downstream sequence elements," vol. 33, No. 3, Jul. 1983, pp. pp. 741-748.

Byrne, G.W. et al., "Multiplex gene regulation: A two-tiered approach to transgene regulation in transgenic mice," PNAS, vol. 86, Jul. 1989, pp. 5473-5477.

Edlund, Thomas et al., "Cell-Specific Expression of the Rat Insulin Gene: Evidence for Role of Two Distinct 5' Flanking Elements," Science, vol. 230, No. 4728, Nov. 1985, pp. 912-916.

Kessel, M. et al., "Murine developmental control genes," Science, vol. 249, No. 4967, Jul. 1990, pp. 374-379.

Camper, Sally A. et al., "Postnatal repression of the α-fetoprotein gene is enhancer independent," Genes & Development, vol. 3, 1989, pp. 537-546.

Nakamura, Yasukazu et al., Nakamura, Y., et al. "Codon usage tabulated from the international DNA sequence databases: status for the year 2000" Nucleic Acids Research, vol. 28, No. Jan. 1, 2000, p. 292.

Anderson, W.F., "Human gene therapy," Science, vol. 256, No. 5058, May 1992, pp. 808-813.

Miller, A.D., "Human gene therapy comes of age," Nature, vol. 357, No. 6378, Jun. 1992, pp. 455-460.

Van Brunt, Jennifer, "Molecular Farming: Transgenic Animals as Bioreactors," Biotechnology, vol. 6, No. 10, Oct. 1988, pp. 1149-1154.

Kremer, E.J. et al., "Adenovirus and adeno-associated virus mediated gene transfer," British Medical Bulletin, vol. 51, No. 1, Jan. 1995, pp. 31-44.

Yu, M. et al., "Progress towards gene therapy for HIV infection," Gene Therapy, vol. 1, No. 1, Jan. 1994, pp. 13-26.

Crystal, R.G., "Transfer of genes to humans: early lessons and obstacles to success," Science, vol. 270, No. 5235, Oct. 1995, pp. 404-410.

Behr, Jean-Paul, "Gene Transfer with Synthetic Cationic Amphiphiles: Prospects for Gene Therapy," Bioconjugate Chemistry, vol. 5, No. 5, Sep. 1994, pp. 382-389.

Remy, Jean-Serge et al., "Gene Transfer with a Series of Lipophilic DNA-Binding Molecules," Bioconjugate Chemistry, vol. 5, No. 6, Nov. 1994, pp. 647-654.

Gao, X. et al., "Cationic liposome-mediated gene transfer," Gene Therapy, vol. 2, No. 10, Dec. 1995, pp. 710-722.

Ahmad, Imran et al., "Antibody-mediated Specific Binding and Cytotoxicity of Liposome-entrapped Doxorubicin to Lung Cancer Cells in Vitro," Cancer Research, vol. 52, Sep. 1992, pp. 4817-4820.

Johann, S. V. et al., GLVR1, a receptor for gibbon ape leukemia virus, is homologous to a phosphate permease of Neurospora crassa and is expressed at high levels in the brain and thymus, Journal of Virology, vol. 66, No. 3, Mar. 1992, pp. 1635-1640.

Wilson, Carolyn et al., "Formation of infectious hybrid virions with gibbon ape leukemia virus and human T-cell leukemia virus retroviral envelope glycoproteins and the gag and pol proteins of Moloney murine leukemia virus," Journal of Virology, vol. 63, No. 5, May 1989, pp. 2374-2378.

Miller, A. Dusty et al., "Construction and properties of retrovirus packaging cells based on gibbon ape leukemia virus," Journal of Virology, vol. 65, No. 5, May 1991, pp. 2220-2224.

West, Michael H. P. et al., "Gene expression in adeno-associated virus vectors: The effects of chimeric mRNA structure, helper virus, and adenovirus VA, RNA," Virology, vol. 160, No. 1, Sep. 1987, pp. 38-47.

Kotin, Robert M., "Prospects for the Use of Adeno-Associated Virus as a Vector for Human Gene Therapy," Human Gene Therapy, vol. 5, No. 7, Jul. 1994, pp. 793-801.

Muzyczka, Nicholas, "Adeno-associated Virus (AAV) Vectors: Will They Work?" Journal of Clinical Investigation, vol. 94, Oct. 1994, p. 1351.

(56)           References Cited

OTHER PUBLICATIONS

Tratschin, Jon-Duri et al., "Adeno-associated virus vector for high-frequency integration, expression, and rescue of genes in mammalian cells," Molecular and Cellular Biology, vol. 5, No. 11, Nov. 1985, pp. 3251-3260.

Tratschin, Jon-Duri et al., A human parvovirus, adeno-associated virus, as a eucaryotic vector: transient expression and encapsidation of the procaryotic gene for chloramphenicol acetyltransferase, Molecular and Cellular Biology, vol. 4, No. 10, Oct. 1984, pp. 2072-2081.

Hermonat, Paul L. et al., "Use of adeno-associated virus as a mammalian DNA cloning vector: transduction of neomycin resistance into mammalian tissue culture cells," PNAS, vol. 81, No. 20, Oct. 1984, pp. 6466-6470.

Samulski, Richard Jude et al. "Helper-free stocks of recombinant adeno-associated viruses: normal integration does hot require viral gene expression," Journal of Virology, vol. 63, No. 9, Sep. 1989, pp. 3822-3828.

* cited by examiner

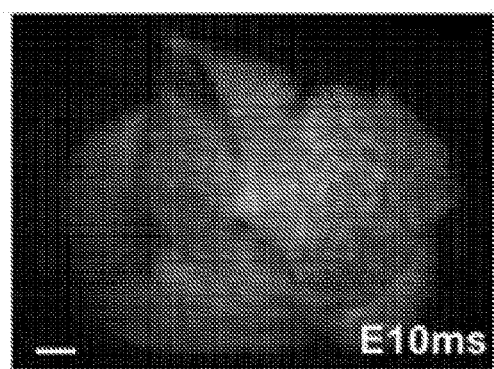
FIG. 1A
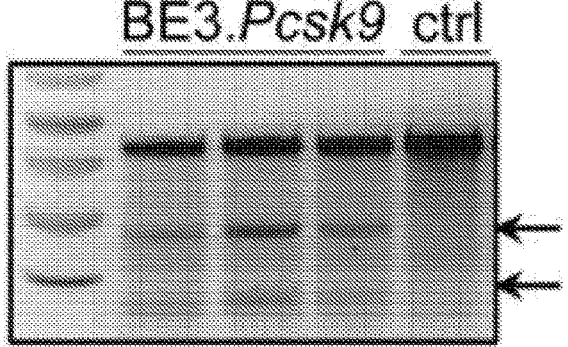
FIG. 1B

FIG. 1E
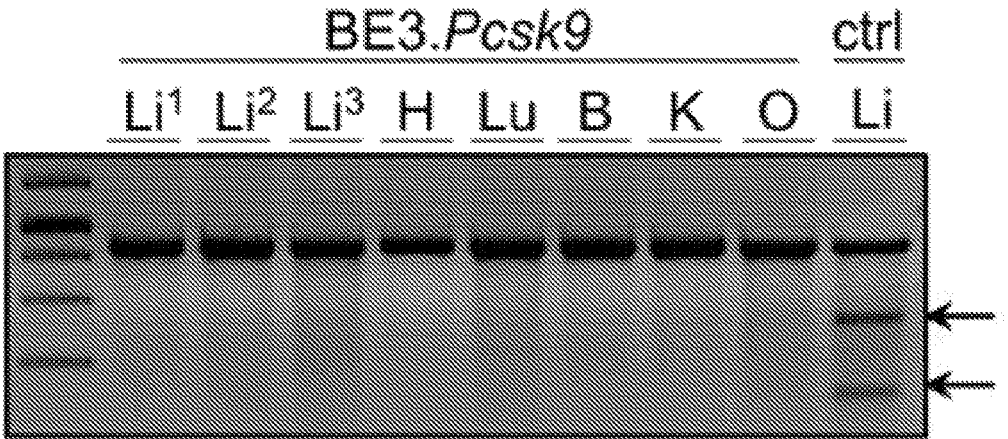

FIG. 1F
2 weeks - liver
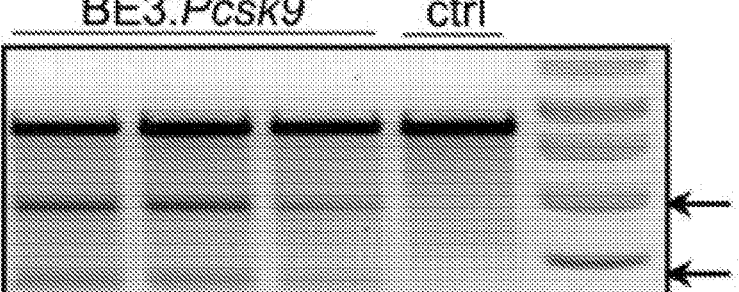
1 month - liver
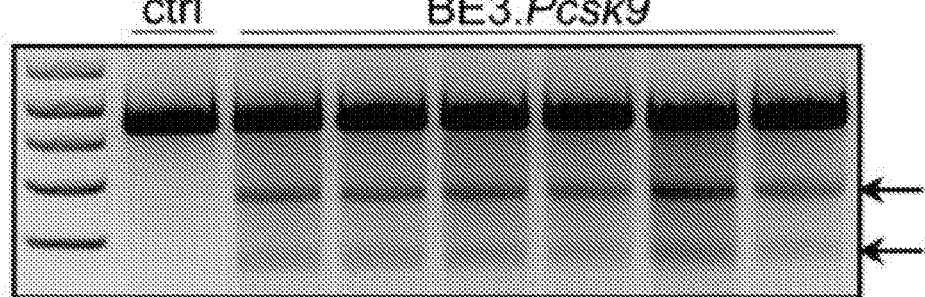
3 months - liver
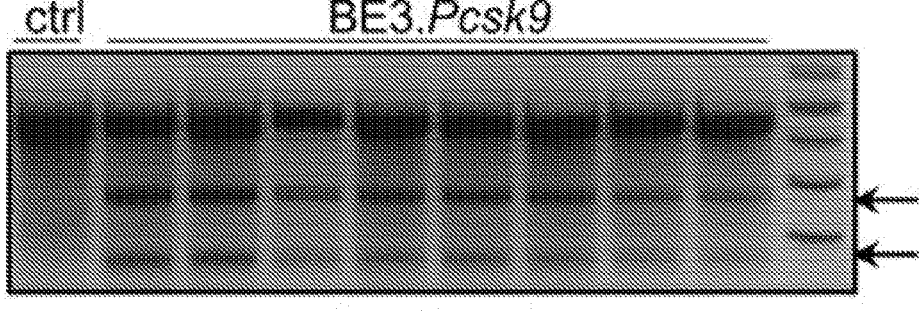
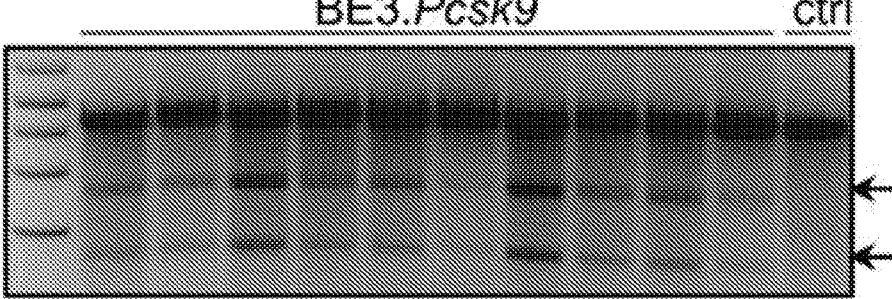

FIG. 1H

| sequence | mutation | type | frequency (out of total reads for 3 month old BE3.*Pcsk9* mouse) |
|---|---|---|---|
| TGGAACC | W159 | wild-type | |
| TAAAACC | W159X | nonsense | 15.0% |
| TGAAACC | W159X | nonsense | 5.07% |
| TTAAACC | W159L | missense | 1.58% |
| TATAACC | W159Y | missense | 0.48% |
| TACAACC | W159Y | missense | 0.22% |
| TAGAACC | W159X | nonsense | 0.11% |
| TCAAACC | W159S | missense | 0.07% |
| other base edits | missense / nonsense / wild-type | | 1.81% |
| indels | frameshift / in-frame | | 2.20% |

FIG. 11

| site | location | sequence | base edits BE3.Pcsk9 (n=2) | base edits ctrl | indels BE3.Pcsk9 (n=2) | indels ctrl |
|---|---|---|---|---|---|---|
| Pcsk9 | Exon:Pcsk9 | CAGGTTCCATGGGATGCTCT GGG | 14.5% / 18.4% | 0.32% | 1.13% / 1.17% | 0.11% |
| OT1 | Intergenic:Snx8-Efr3b | CGCGGTCTATGGGATGCTCT GGG | 0.06% / 0.11% | 0.06% | 0.02% / 0.04% | 0.03% |
| OT2 | Intron:Spata5 | CAGTTCCATGGGGTGCTCT TGG | 0.05% / 0.08% | 0.06% | 0.03% / 0.04% | 0.04% |
| OT3 | Intron:Ephb1 | TGTTTCCATGGGATGCTCT TGG | 0.10% / 0.14% | 0.08% | 0.02% / 0.05% | 0.01% |
| OT4 | Intron:Cnnm1 | CAAGCTCTAAGGGGATGCTCT GGG | 0.06% / 0.05% | 0.09% | 0.04% / 0.04% | 0.03% |
| OT5 | Exon:Cd5 | CACGATGGAGGGGATGCTCT TGG | ---- / ---- | ---- | 0.04% / 0.03% | 0.04% |
| OT6 | Exon:Mansc4 | CCGCTTCCCGGGGATGCTCT TGG | 0.19% / 0.18% | 0.16% | 0.04% / 0.04% | 0.04% |
| OT7 | Intron:Shisa9 | CAGGTTTATGGTATGCTCT AGG | ---- / ---- | ---- | 0.04% / 0.04% | 0.03% |
| OT8 | Exon:Gpr165 | GAAGTTCATTGGATGCTCT GGG | 0.03% / 0.02% | 0.02% | 0.02% / 0.01% | 0.02% |
| OT9 | Exon:Mtg1-Spm | CTGGTTCCATGGGAGGCTCAAGG | 0.06% / 0.05% | 0.06% | 0.06% / 0.07% | 0.07% |

FIG. 2A
FIG. 2B
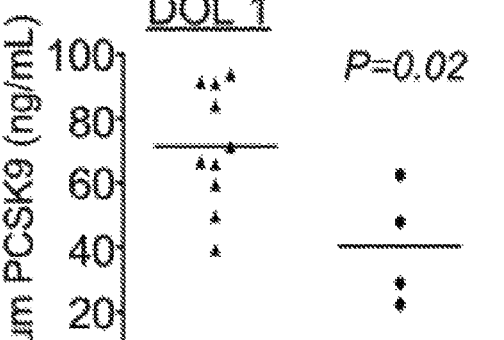
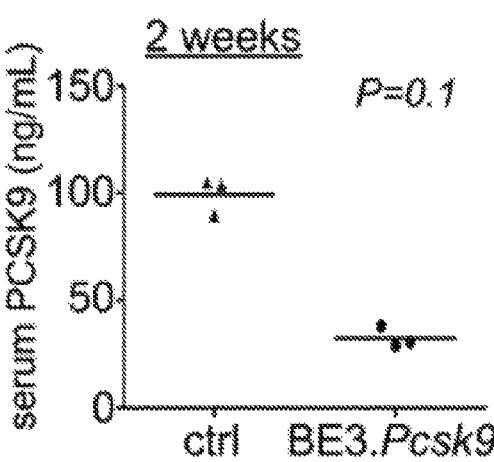

FIG. 2C
FIG. 2D
FIG. 2E
FIG. 2F
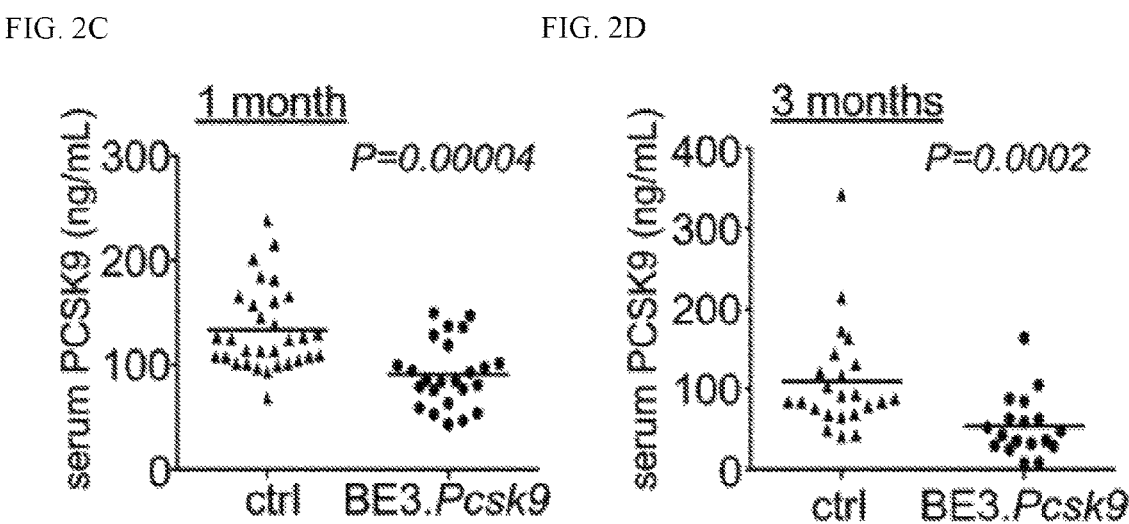
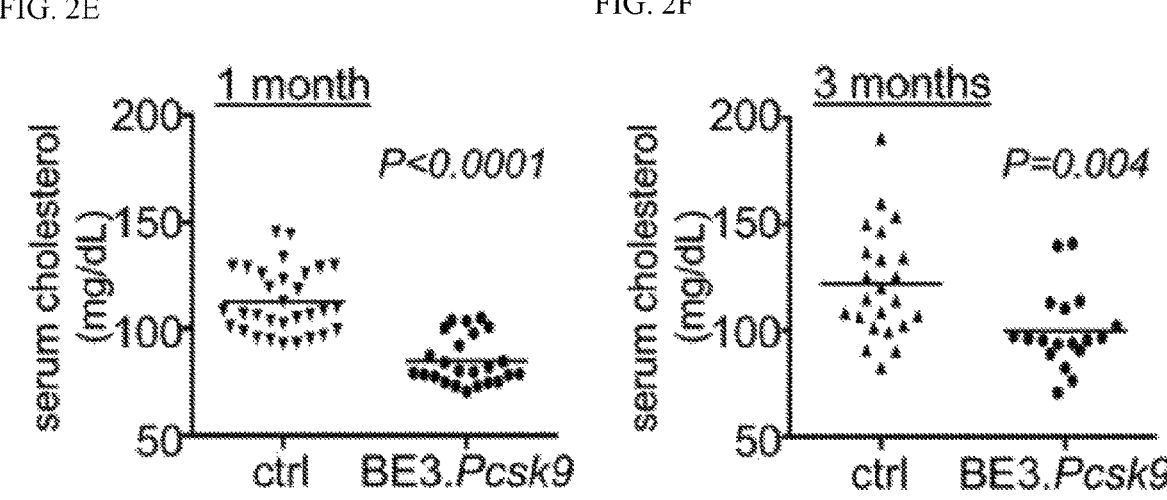

FIG. 2G
FIG. 2H
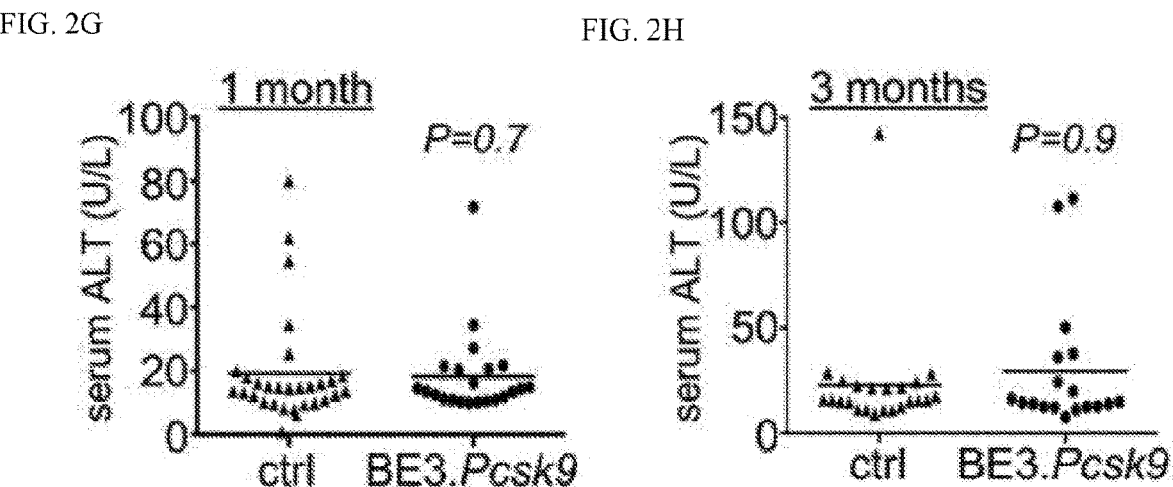
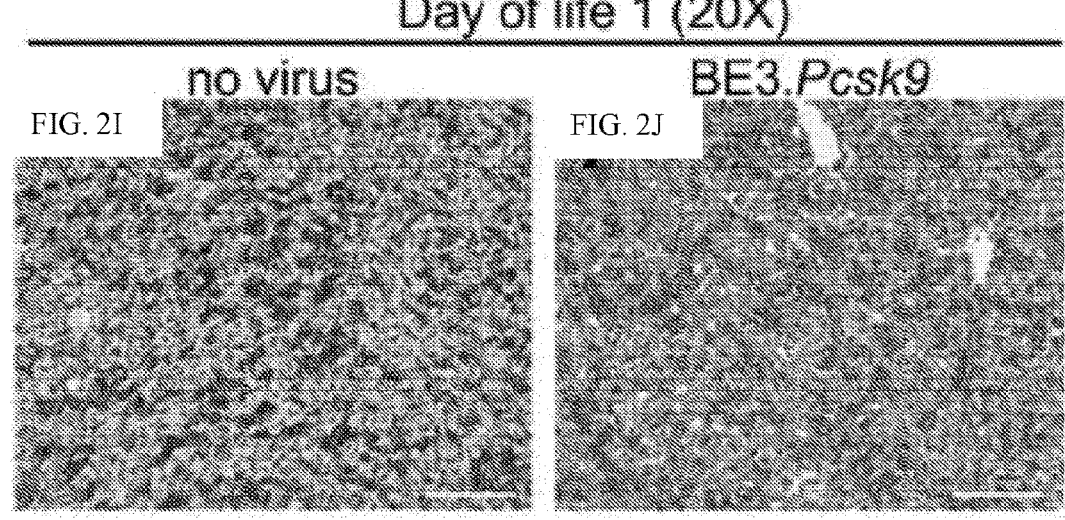
FIG. 2I
FIG. 2J 3 months (10X)
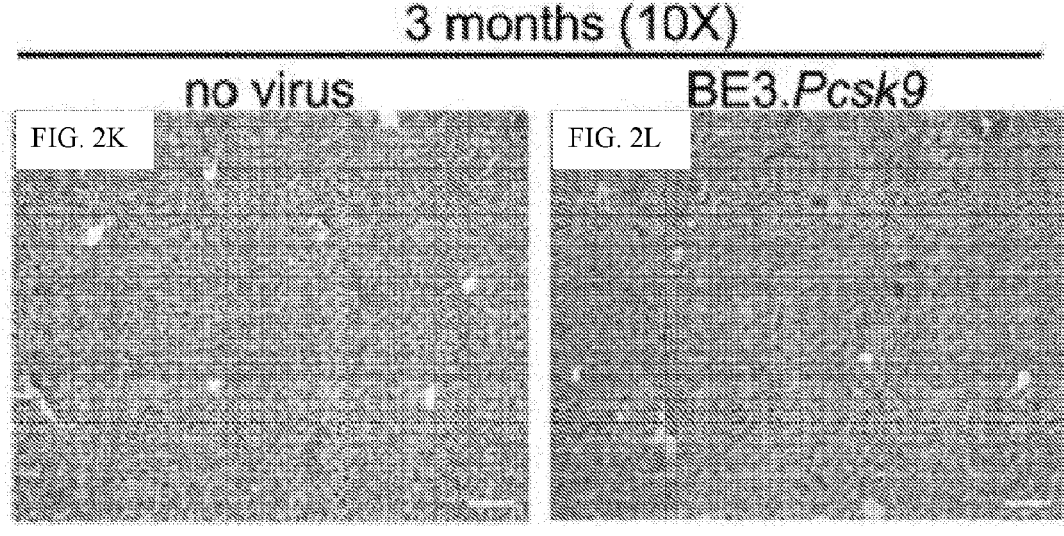
FIG. 2M
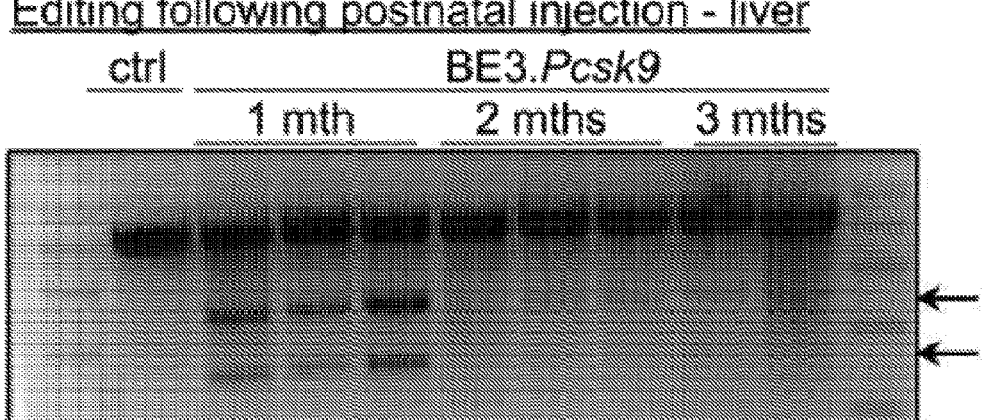

FIG. 3A

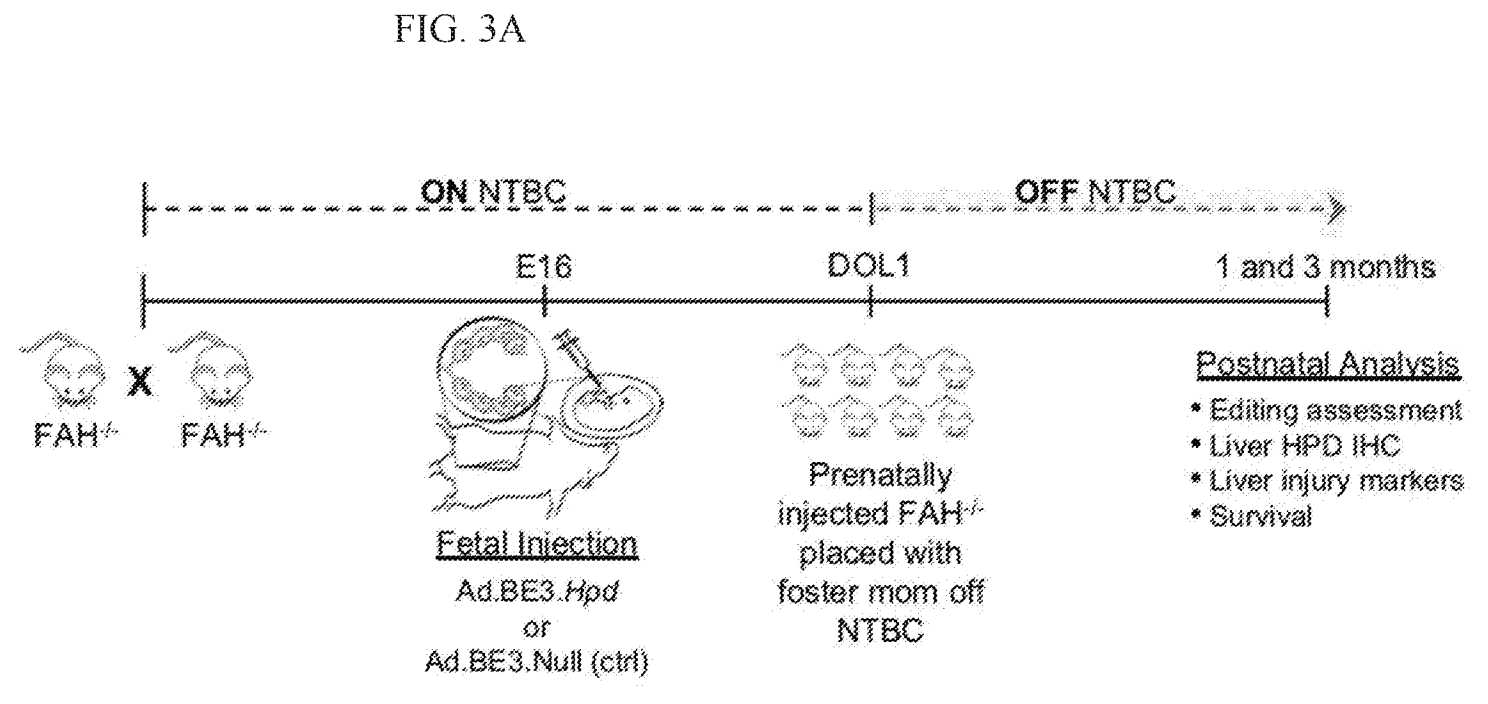

ON NTBC

OFF NTBC

FAH⁻/⁻ X FAH⁻/⁻

E16

Fetal Injection
Ad.BE3.Hpd
or
Ad.BE3.Null (ctrl)

DOL1

Prenatally
injected FAH⁻/⁻
placed with
foster mom off
NTBC 1 and 3 months

Postnatal Analysis
* Editing assessment
* Liver HPD IHC
* Liver injury markers
* Survival

FIG. 3C

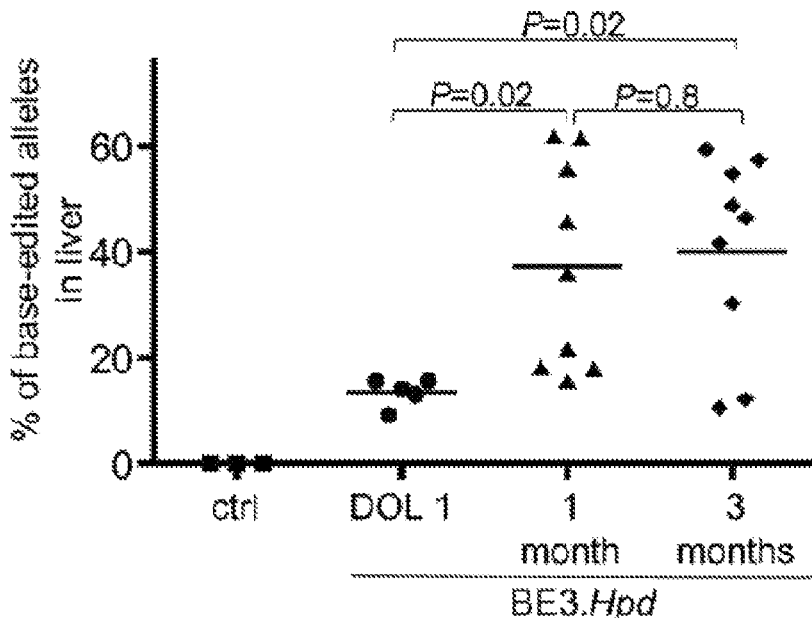

FIG. 3D

| sequence | mutation | type | mean frequency (out of total reads) ± SEM for all mice @ 3 months (N = 9) |
|---|---|---|---|
| TTCAACGT | Q352 | wild-type | |
| TTTAACGT | Q352X | nonsense | 35.84 ± 6.34% |
| TTTAATGT | Q352X | nonsense | 1.01 ± 0.02% |
| TTCAATGT | Q352Q | wild-type* | 0.12 ± 0.02% |
| TTTAGCGT | Q352X | nonsense | 0.04 ± 0.01% |
| TTTAAAGT | Q352X | nonsense | 0.03 ± 0.01% |
| TTTACCGT | Q352Y | missense | 0.03 ± 0.01% |
| other base edits | missense / nonsense / wild-type | | 0.2 ± 0.03% |
| indels | frameshift / in-frame | | 4.14 ± 0.64% |

* targeted codon unchanged but downstream C changed to T (in bold) resulting in R353C

FIG. 3F

| site | location | sequence | base edits | | indels | |
|---|---|---|---|---|---|---|
| | | | BE3.Hpd (N=2) | ctrl | BE3.Hpd (N=2) | ctrl |
| Hpd | Exon:Hpd | CATTCAAGGTCACAACCACC AGG | 45.89% / 61.66% | 0.03% | 5.89% / 6.97% | 0.02% |
| OT1 | Intergenic:Cbln2_Gm3086 | CATTCAACTCACAACCACA AGG | 0.11% / 0.10% | 0.09% | 0.03% / 0.04% | 0.02% |
| OT2 | Intergenic:B930078G14Rik=Fam155a | CGGTTAAGGTCACAACCACC TGG | ----- / ----- | ----- | 0.05% / 0.05% | 0.03% |
| OT3 | Intron:Shank2 | GGAGCAACGTCACAACCACC AGG | 0.09% / 0.11% | 0.10% | 0.03% / 0.03% | 0.04% |
| OT4 | Intron:Lrrc4c | TATTCAAAAGCACAACCACC TGG | 0.01% / 0.01% | 0.01% | 0.03% / 0.05% | 0.03% |
| OT5 | intergenic:5730420D15Rik-Mrp142 | ATTTCAAGGTCACAACCACA GGG | 0.02% / 0.01% | 0.02% | 0.03% / 0.04% | 0.02% |
| OT6 | intergenic:Gm2574-Gm24728 | AATTCAAGGTCACAACCCCC AGG | 0.01% / 0.02% | 0.01% | 0.13% / 0.13% | 0.13% |
| OT7 | Intron:Epha5 | CATAAATGTCACAACCACA TGG | ----- / ----- | ----- | 0.08% / 0.08% | 0.03% |
| OT8 | Exon:Lpin1 | CCTTCACCGTCACAAACACC TGG | 0.58% / 0.82% | 0.57% | 0.16% / 0.18% | 0.12% |
| OT9 | Exon:Arphl8 | CATACAACATCACAACCATC AGG | 0.04% / 0.07% | 0.04% | 0.01% / 0.01% | 0.02% |
| OT10 | Exon:A4galt | CTTTCATCAGCACAACCACC TGG | 0.04% / 0.04% | 0.05% | 0.04% / 0.04% | 0.04% |

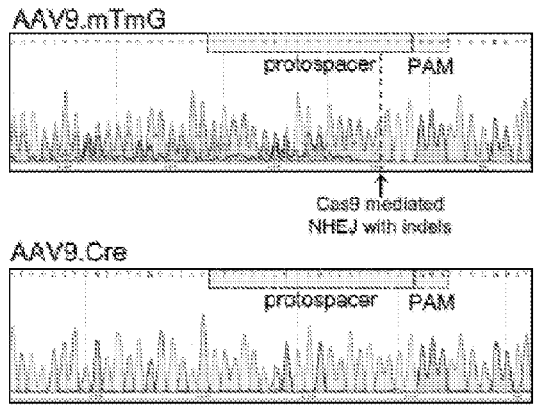
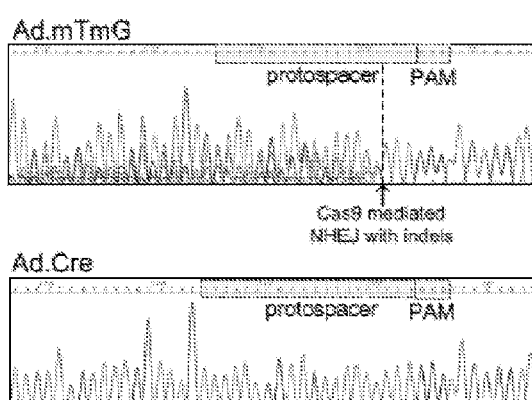
FIG. 5C

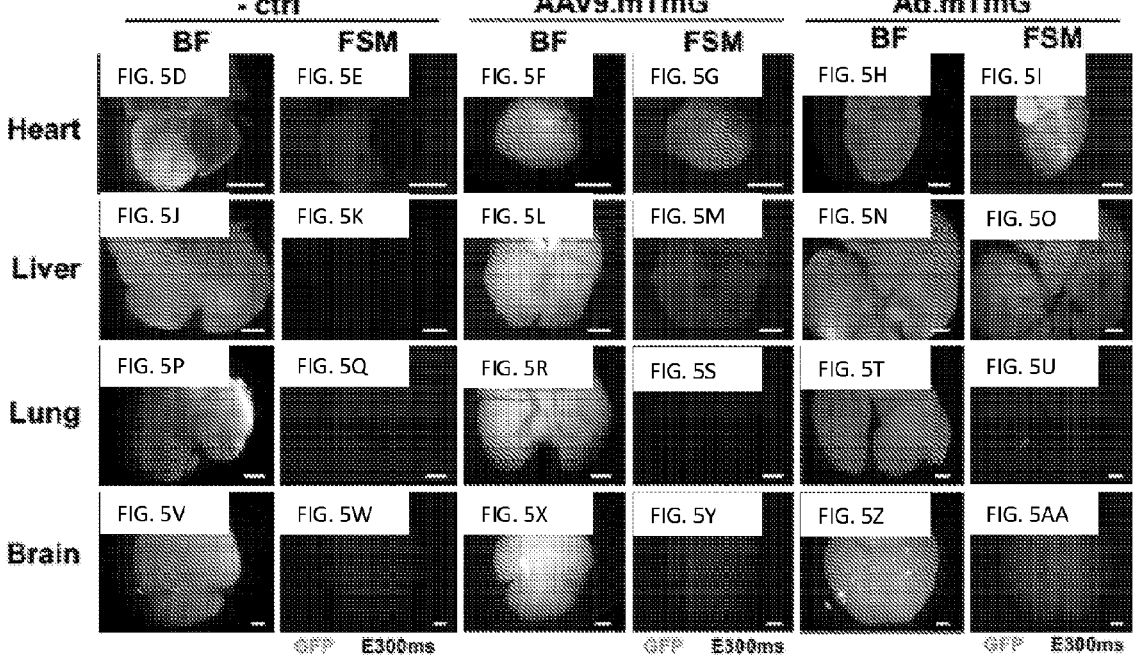

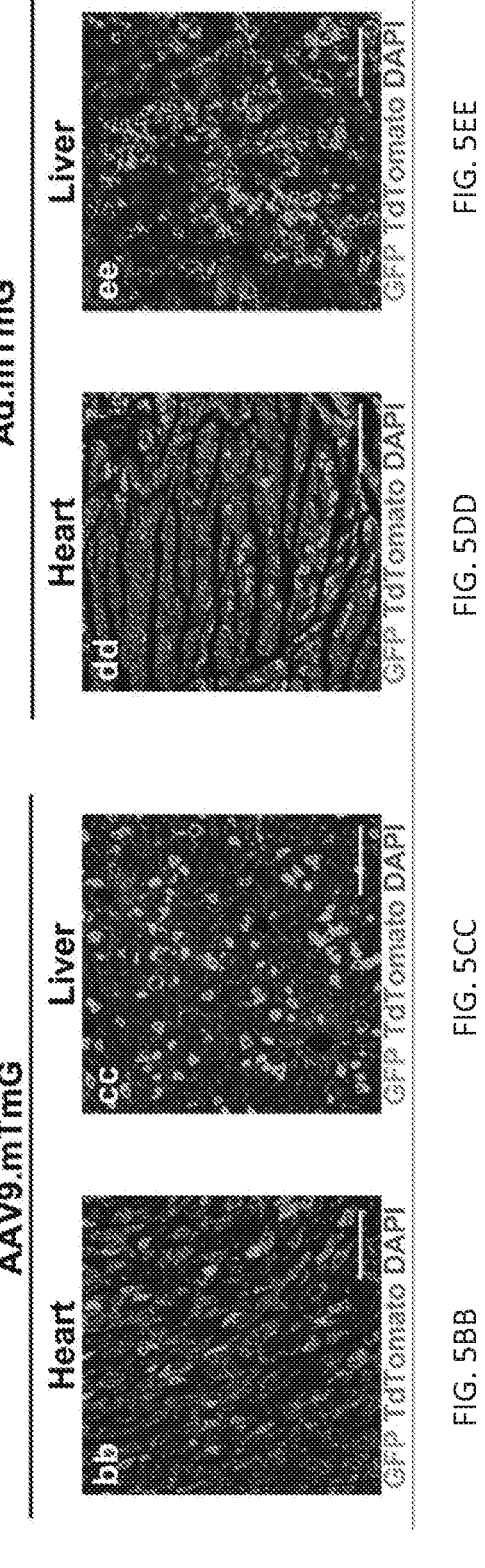

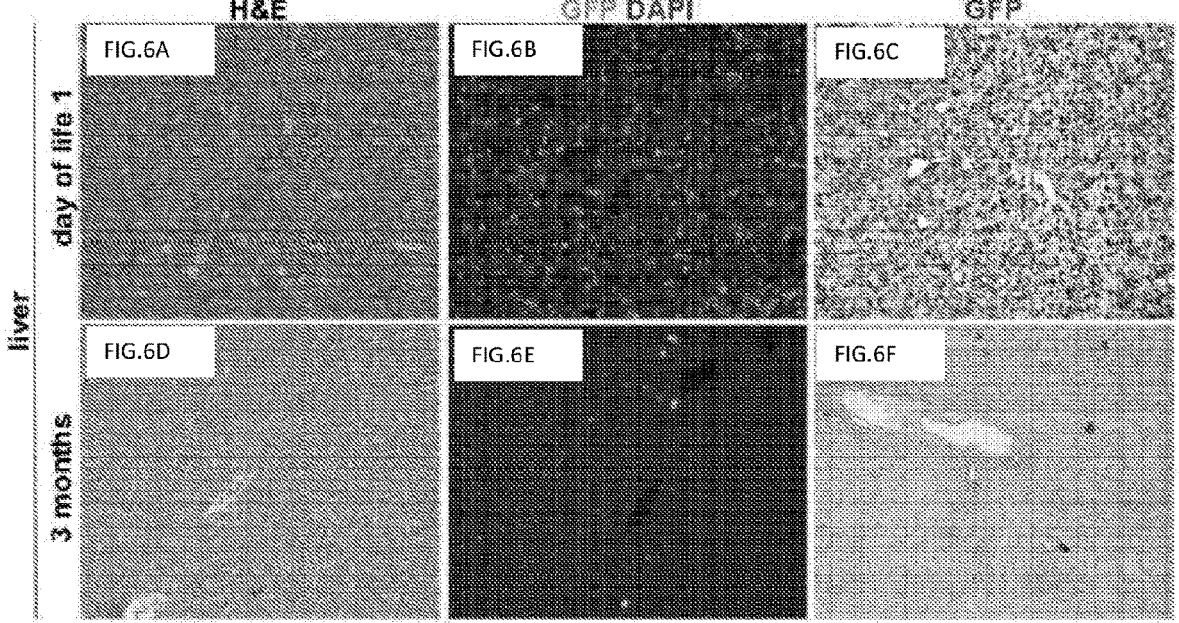

FIG. 7B

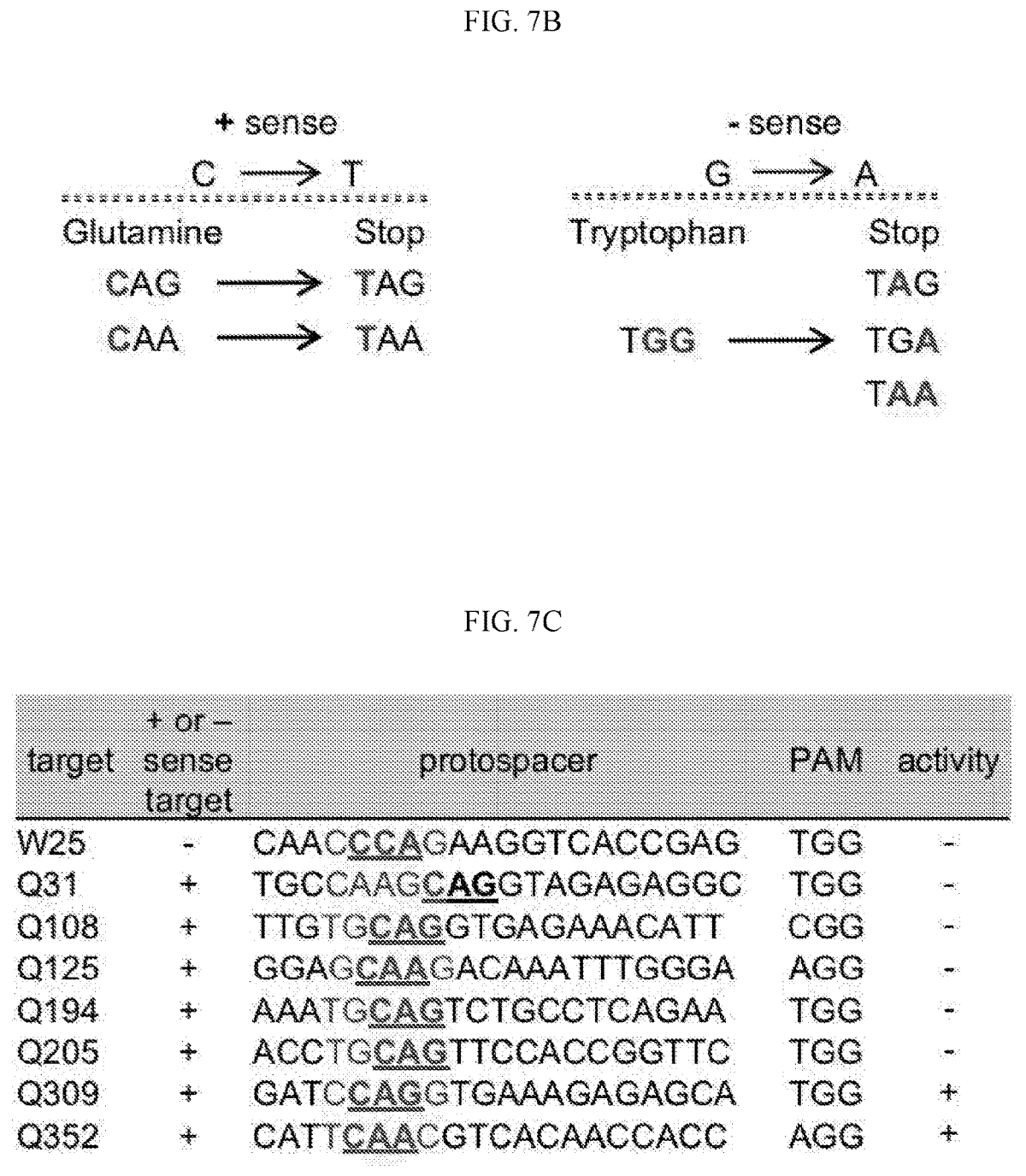

+ sense

C ⟶ T

Glutamine          Stop

CAG ⟶ TAG

CAA ⟶ TAA

− sense

G ⟶ A

Tryptophan          Stop

TAG

TGG ⟶ TGA

TAA

FIG. 7C

| target | + or −<br>sense<br>target | protospacer | PAM | activity |
|---|---|---|---|---|
| W25 | − | CAACCCAGAAGGTCACCGAG | TGG | − |
| Q31 | + | TGCCAGCCAGGTAGAGAGGC | TGG | − |
| Q108 | + | TTGTGCAGGTGAGAAACATT | CGG | − |
| Q125 | + | GGAGCAAGACAAATTTGGGA | AGG | − |
| Q194 | + | AAATGCAGTCTGCCTCAGAA | TGG | − |
| Q205 | + | ACCTGCAGTTCCACCGGTTC | TGG | − |
| Q309 | + | GATCCAGGTGAAAGAGAGCA | TGG | + |
| Q352 | + | CATTCAACGTCACAACCACC | AGG | + |

FIG. 7M

Pcsk9 targeting in
N2a cells

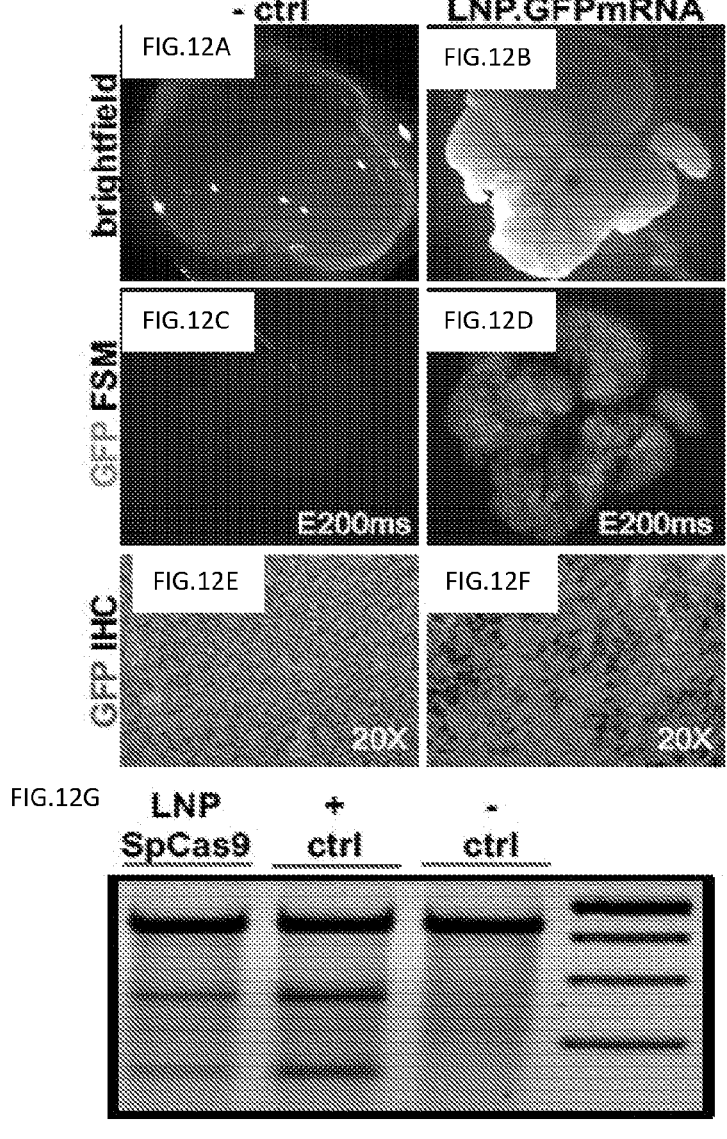

*FAH* sequence                                                allele     frequency ACCATCAGCGGGCCGGTGA<u>G</u>TATCTGGCTGCACTGAGGGC     wild-type
ACCATCAGCGGGCCGGTGA<u>A</u>TATCTGGCTGCACTGAGGGC     Quebec A??TCAGCGGGCCGG?????ATC?GGCTGCACTGAGGGC          wild-type
ACCATCAGCGGGCCGGTAAATATCTGGCTGCACTGAGGGC      293.BE3

ACCATCAGCGGGCCGGTAAATCTGGCTGCACTG???GC        293.BE3
...............GTAA<u>G</u>TGTC................   ABE edit      5.1%
...............GTGA<u>G</u>TGTC...............ABE edit      1.9%
...............GTAGGTGTC..............         ABE edit      0.9%
...............GTGGGTGTC.............          ABE edit      0.8%
...............GTAA<u>G</u>TATC..............      ABE edit      0.1%

FIG. 14

SEQUENCE LISTING

<160> NUMBER OF SEQ ID NOS: 125

<210> SEQ ID NO 1
<211> LENGTH: 23
<212> TYPE: DNA
<213> ORGANISM: Artificial Sequence
<220> FEATURE:
<223> OTHER INFORMATION: protospacer and PAM sequence

<400> SEQUENCE: 1
ctggttccat gggaggctca agg                                                      23

<210> SEQ ID NO 2
<211> LENGTH: 23
<212> TYPE: DNA
<213> ORGANISM: Artificial Sequence
<220> FEATURE:
<223> OTHER INFORMATION: protospacer and PAM sequence

<400> SEQUENCE: 2
gaagtttcat tggatgctct ggg                                                      23

<210> SEQ ID NO 3
<211> LENGTH: 23
<212> TYPE: DNA
<213> ORGANISM: Artificial Sequence
<220> FEATURE:
<223> OTHER INFORMATION: protospacer and PAM sequence

<400> SEQUENCE: 3
caggttttat ggtatgctct agg                                                      23

<210> SEQ ID NO 4
<211> LENGTH: 23
<212> TYPE: DNA
<213> ORGANISM: Artificial Sequence
<220> FEATURE:
<223> OTHER INFORMATION: protospacer and PAM sequence

<400> SEQUENCE: 4
ccgcttcccg gggatgctct tgg                                                      23

<210> SEQ ID NO 5
<211> LENGTH: 23
<212> TYPE: DNA
<213> ORGANISM: Artificial Sequence
<220> FEATURE:
<223> OTHER INFORMATION: protospacer and PAM sequence

<400> SEQUENCE: 5
caggatggag gggatgctct tgg                                                      23

<210> SEQ ID NO 6
<211> LENGTH: 23
<212> TYPE: DNA
<213> ORGANISM: Artificial Sequence
<220> FEATURE:
<223> OTHER INFORMATION: protospacer and PAM sequence

<400> SEQUENCE: 6
caagctctaa gggatgctct ggg                                                      23

<210> SEQ ID NO 7
<211> LENGTH: 23
<212> TYPE: DNA
<213> ORGANISM: Artificial Sequence
<220> FEATURE:
<223> OTHER INFORMATION: protospacer and PAM sequence

<400> SEQUENCE: 7
tgttttccat gggatgctct tgg                                        23

<210> SEQ ID NO 8
<211> LENGTH: 23
<212> TYPE: DNA
<213> ORGANISM: Artificial Sequence
<220> FEATURE:
<223> OTHER INFORMATION: protospacer and PAM sequence

<400> SEQUENCE: 8
cagtttccat ggggtgctct tgg                                        23

<210> SEQ ID NO 9
<211> LENGTH: 23
<212> TYPE: DNA
<213> ORGANISM: Artificial Sequence
<220> FEATURE:
<223> OTHER INFORMATION: protospacer and PAM sequence

<400> SEQUENCE: 9
cgcggtctat gggatgctct ggg                                        23

<210> SEQ ID NO 10
<211> LENGTH: 23
<212> TYPE: DNA
<213> ORGANISM: Artificial Sequence
<220> FEATURE:
<223> OTHER INFORMATION: protospacer and PAM sequence

<400> SEQUENCE: 10
caggttccat gggatgctct ggg                                        23

<210> SEQ ID NO 11
<211> LENGTH: 23
<212> TYPE: DNA
<213> ORGANISM: Artificial Sequence
<220> FEATURE:
<223> OTHER INFORMATION: protospacer and PAM sequence

<400> SEQUENCE: 11
ctttcatcag cacaaccacc tgg                                        23

<210> SEQ ID NO 12
<211> LENGTH: 23
<212> TYPE: DNA
<213> ORGANISM: Artificial Sequence
<220> FEATURE:
<223> OTHER INFORMATION: protospacer and PAM sequence

<400> SEQUENCE: 12
catacaacat cacaaccatc agg                                        23

<210> SEQ ID NO 13
<211> LENGTH: 23
<212> TYPE: DNA
<213> ORGANISM: Artificial Sequence
<220> FEATURE:
<223> OTHER INFORMATION: protospacer and PAM sequence

<400> SEQUENCE: 13
ccttcaccgt cacaaacacc tgg                                        23

56

-continued

```
<210> SEQ ID NO 14
<211> LENGTH: 23
<212> TYPE: DNA
<213> ORGANISM: Artificial Sequence
<220> FEATURE:
<223> OTHER INFORMATION: protospacer and PAM sequence

<400> SEQUENCE: 14
cataaaatgt cacaaccaca tgg                                             23

<210> SEQ ID NO 15
<211> LENGTH: 23
<212> TYPE: DNA
<213> ORGANISM: Artificial Sequence
<220> FEATURE:
<223> OTHER INFORMATION: protospacer and PAM sequence

<400> SEQUENCE: 15
aattcaaggt cacaaccccc agg                                             23

<210> SEQ ID NO 16
<211> LENGTH: 23
<212> TYPE: DNA
<213> ORGANISM: Artificial Sequence
<220> FEATURE:
<223> OTHER INFORMATION: protospacer and PAM sequence

<400> SEQUENCE: 16
atttcaaagt cacaaccaca ggg                                             23

<210> SEQ ID NO 17
<211> LENGTH: 23
<212> TYPE: DNA
<213> ORGANISM: Artificial Sequence
<220> FEATURE:
<223> OTHER INFORMATION: protospacer and PAM sequence

<400> SEQUENCE: 17
tattcaaaac cacaaccacc tgg                                             23

<210> SEQ ID NO 18
<211> LENGTH: 23
<212> TYPE: DNA
<213> ORGANISM: Artificial Sequence
<220> FEATURE:
<223> OTHER INFORMATION: protospacer and PAM sequence

<400> SEQUENCE: 18
ggagcaacgt cacaaccacc agg                                             23

<210> SEQ ID NO 19
<211> LENGTH: 23
<212> TYPE: DNA
<213> ORGANISM: Artificial Sequence
<220> FEATURE:
<223> OTHER INFORMATION: protospacer and PAM sequence

<400> SEQUENCE: 19
cggttaaggt cacaaccacc tgg                                             23

<210> SEQ ID NO 20
<211> LENGTH: 23
<212> TYPE: DNA
<213> ORGANISM: Artificial Sequence
<220> FEATURE:
<223> OTHER INFORMATION: protospacer and PAM sequence
```

-continued

```
<400> SEQUENCE: 20
cattcaacct cacaaccaca agg                                      23

<210> SEQ ID NO 21
<211> LENGTH: 23
<212> TYPE: DNA
<213> ORGANISM: Artificial Sequence
<220> FEATURE:
<223> OTHER INFORMATION: protospacer and PAM sequence

<400> SEQUENCE: 21
cattcaacgt cacaaccacc agg                                      23

<210> SEQ ID NO 22
<211> LENGTH: 20
<212> TYPE: DNA
<213> ORGANISM: Artificial Sequence
<220> FEATURE:
<223> OTHER INFORMATION: protospacer sequence

<400> SEQUENCE: 22
caggttccat gggatgctct                                          20

<210> SEQ ID NO 23
<211> LENGTH: 50
<212> TYPE: DNA
<213> ORGANISM: Artificial Sequence
<220> FEATURE:
<223> OTHER INFORMATION: target site sequence

<400> SEQUENCE: 23 aaactttta aaaccaacct ttttcgaaat tataattaag ggttccggat          50

<210> SEQ ID NO 24
<211> LENGTH: 49
<212> TYPE: DNA
<213> ORGANISM: Artificial Sequence
<220> FEATURE:
<223> OTHER INFORMATION: target site sequence

<400> SEQUENCE: 24
aaattcgtat agcatacaca atacgaaaat atatttaagg gttccggat          49

<210> SEQ ID NO 25
<211> LENGTH: 50
<212> TYPE: DNA
<213> ORGANISM: Artificial Sequence
<220> FEATURE:
<223> OTHER INFORMATION: target site sequence

<400> SEQUENCE: 25
ataacttcgt atagcataca ttatacgaag ttatattaag ggttccggat         50

<210> SEQ ID NO 26
<211> LENGTH: 47
<212> TYPE: DNA
<213> ORGANISM: Artificial Sequence
<220> FEATURE:
<223> OTHER INFORMATION: target site sequence

<400> SEQUENCE: 26
aacttcgtat agcatacatt atacgaagtt atattaaggg ttccgat            47

<210> SEQ ID NO 27
```

-continued

```
<211> LENGTH: 26
<212> TYPE: DNA
<213> ORGANISM: Artificial Sequence
<220> FEATURE:
<223> OTHER INFORMATION: target site sequence

<400> SEQUENCE: 27
atcgtgcagg taagaaagca cctggg                                         26

<210> SEQ ID NO 28
<211> LENGTH: 26
<212> TYPE: DNA
<213> ORGANISM: Artificial Sequence
<220> FEATURE:
<223> OTHER INFORMATION: target site sequence

<400> SEQUENCE: 28
aaaacctgca gttccaccgc ttctgg                                         26

<210> SEQ ID NO 29
<211> LENGTH: 26
<212> TYPE: DNA
<213> ORGANISM: Artificial Sequence
<220> FEATURE:
<223> OTHER INFORMATION: target site sequence

<400> SEQUENCE: 29
tagctctctg cgatccattg tggtgg                                         26

<210> SEQ ID NO 30
<211> LENGTH: 23
<212> TYPE: DNA
<213> ORGANISM: Artificial Sequence
<220> FEATURE:
<223> OTHER INFORMATION: protospacer and PAM sequence

<400> SEQUENCE: 30
gtgcaggtaa gaaagcacct ggg                                            23

<210> SEQ ID NO 31
<211> LENGTH: 23
<212> TYPE: DNA
<213> ORGANISM: Artificial Sequence
<220> FEATURE:
<223> OTHER INFORMATION: protospacer and PAM sequence

<400> SEQUENCE: 31
acctgcagtt ccaccgcttc tgg                                            23

<210> SEQ ID NO 32
<211> LENGTH: 23
<212> TYPE: DNA
<213> ORGANISM: Artificial Sequence
<220> FEATURE:
<223> OTHER INFORMATION: protospacer and PAM sequence

<400> SEQUENCE: 32
ctctctgcta tccattgtgg tgg                                            23

<210> SEQ ID NO 33
<211> LENGTH: 23
<212> TYPE: DNA
<213> ORGANISM: Artificial Sequence
<220> FEATURE:
<223> OTHER INFORMATION: protospacer and PAM sequence

<400> SEQUENCE: 33
```
cctgcagatc ttcaccaaac cgg                                        23

<210> SEQ ID NO 34
<211> LENGTH: 20
<212> TYPE: DNA
<213> ORGANISM: Artificial Sequence
<220> FEATURE:
<223> OTHER INFORMATION: protospacer and PAM sequence

<400> SEQUENCE: 34
catccagcgc cacaaccacc                                           20

<210> SEQ ID NO 35
<211> LENGTH: 23
<212> TYPE: DNA
<213> ORGANISM: Artificial Sequence
<220> FEATURE:
<223> OTHER INFORMATION: protospacer and PAM sequence

<400> SEQUENCE: 35
caccaggtac tgcttgtccc cgg                                        23

<210> SEQ ID NO 36
<211> LENGTH: 20
<212> TYPE: DNA
<213> ORGANISM: Artificial Sequence
<220> FEATURE:
<223> OTHER INFORMATION: protospacer sequence

<400> SEQUENCE: 36
cattcaacgt cacaaccacc                                           20

<210> SEQ ID NO 37
<211> LENGTH: 25
<212> TYPE: DNA
<213> ORGANISM: Artificial Sequence
<220> FEATURE:
<223> OTHER INFORMATION: protospacer and PAM sequence

<400> SEQUENCE: 37
acattatacg aagttatatt aaggg                                     25

<210> SEQ ID NO 38
<211> LENGTH: 23
<212> TYPE: DNA
<213> ORGANISM: Artificial Sequence
<220> FEATURE:
<223> OTHER INFORMATION: protospacer and PAM sequence

<400> SEQUENCE: 38
cattcaacgt cacaaccacc agg                                        23

<210> SEQ ID NO 39
<211> LENGTH: 23
<212> TYPE: DNA
<213> ORGANISM: Artificial Sequence
<220> FEATURE:
<223> OTHER INFORMATION: protospacer and PAM sequence

<400> SEQUENCE: 39
gatccaggtg aaagagagca tgg                                        23

<210> SEQ ID NO 40
<211> LENGTH: 23
<212> TYPE: DNA

-continued

```
<213> ORGANISM: Artificial Sequence
<220> FEATURE:
<223> OTHER INFORMATION: protospacer and PAM sequence

<400> SEQUENCE: 40
acctgcagtt ccaccggttc tgg                                              23

<210> SEQ ID NO 41
<211> LENGTH: 23
<212> TYPE: DNA
<213> ORGANISM: Artificial Sequence
<220> FEATURE:
<223> OTHER INFORMATION: protospacer and PAM sequence

<400> SEQUENCE: 41
aaatgcagtc tgcctcagaa tgg                                              23

<210> SEQ ID NO 42
<211> LENGTH: 23
<212> TYPE: DNA
<213> ORGANISM: Artificial Sequence
<220> FEATURE:
<223> OTHER INFORMATION: protospacer and PAM sequence

<400> SEQUENCE: 42
ggagcaagac aaatttggga agg                                              23

<210> SEQ ID NO 43
<211> LENGTH: 23
<212> TYPE: DNA
<213> ORGANISM: Artificial Sequence
<220> FEATURE:
<223> OTHER INFORMATION: protospacer and PAM sequence

<400> SEQUENCE: 43
ttgtgcaggt gagaaacatt cgg                                              23

<210> SEQ ID NO 44
<211> LENGTH: 23
<212> TYPE: DNA
<213> ORGANISM: Artificial Sequence
<220> FEATURE:
<223> OTHER INFORMATION: protospacer and PAM sequence

<400> SEQUENCE: 44
tgccaagcag gtagagaggc tgg                                              23

<210> SEQ ID NO 45
<211> LENGTH: 23
<212> TYPE: DNA
<213> ORGANISM: Artificial Sequence
<220> FEATURE:
<223> OTHER INFORMATION: protospacer and PAM sequence

<400> SEQUENCE: 45
caacccagaa ggtcaccgag tgg                                              23

<210> SEQ ID NO 46
<211> LENGTH: 20
<212> TYPE: DNA
<213> ORGANISM: Artificial Sequence
<220> FEATURE:
<223> OTHER INFORMATION: protospacer and PAM sequence

<400> SEQUENCE: 46
caggttccat gggatgctct                                                  20
```

```
<210> SEQ ID NO 47
<211> LENGTH: 20
<212> TYPE: DNA
<213> ORGANISM: Artificial Sequence
<220> FEATURE:
<223> OTHER INFORMATION: protospacer and PAM sequence

<400> SEQUENCE: 47
cattcaacgt cacaaccacc                                             20

<210> SEQ ID NO 48
<211> LENGTH: 20
<212> TYPE: DNA
<213> ORGANISM: Artificial Sequence
<220> FEATURE:
<223> OTHER INFORMATION: protospacer and PAM sequence

<400> SEQUENCE: 48
ggtgctagcc ttgcgttccg                                             20

<210> SEQ ID NO 49
<211> LENGTH: 22
<212> TYPE: DNA
<213> ORGANISM: Artificial Sequence
<220> FEATURE:
<223> OTHER INFORMATION: protospacer and PAM sequence

<400> SEQUENCE: 49
acattatacg aagttatatt aa                                          22

<210> SEQ ID NO 50
<211> LENGTH: 21
<212> TYPE: DNA
<213> ORGANISM: Artificial Sequence
<220> FEATURE:
<223> OTHER INFORMATION: primer sequence

<400> SEQUENCE: 50
tctcccccgc acttagtttc c                                           21

<210> SEQ ID NO 51
<211> LENGTH: 22
<212> TYPE: DNA
<213> ORGANISM: Artificial Sequence
<220> FEATURE:
<223> OTHER INFORMATION: primer sequence

<400> SEQUENCE: 51
ggactcagat gctgggctga tg                                          22

<210> SEQ ID NO 52
<211> LENGTH: 15
<212> TYPE: DNA
<213> ORGANISM: Artificial Sequence
<220> FEATURE:
<223> OTHER INFORMATION: mutated target sequence

<400> SEQUENCE: 52
gtcattcaac gtcac                                                  15

<210> SEQ ID NO 53
<211> LENGTH: 21
<212> TYPE: DNA
<213> ORGANISM: Artificial Sequence
<220> FEATURE:
```

<223> OTHER INFORMATION: primer sequence

<400> SEQUENCE: 53
cctgtccgtt cgctttggaa g                                                 21

<210> SEQ ID NO 54
<211> LENGTH: 22
<212> TYPE: DNA
<213> ORGANISM: Artificial Sequence
<220> FEATURE:
<223> OTHER INFORMATION: primer sequence

<400> SEQUENCE: 54
aaatctgtgc ggagccgaaa tc                                                22

<210> SEQ ID NO 55
<211> LENGTH: 21
<212> TYPE: DNA
<213> ORGANISM: Artificial Sequence
<220> FEATURE:
<223> OTHER INFORMATION: primer sequence

<400> SEQUENCE: 55
agagagcaca gagaggtcag t                                                 21

<210> SEQ ID NO 56
<211> LENGTH: 20
<212> TYPE: DNA
<213> ORGANISM: Artificial Sequence
<220> FEATURE:
<223> OTHER INFORMATION: primer sequence

<400> SEQUENCE: 56
ttcaggggct ggagttacgg                                                   20

<210> SEQ ID NO 57
<211> LENGTH: 20
<212> TYPE: DNA
<213> ORGANISM: Artificial Sequence
<220> FEATURE:
<223> OTHER INFORMATION: primer sequence

<400> SEQUENCE: 57
catgtgtgga tgggggctta                                                   20

<210> SEQ ID NO 58
<211> LENGTH: 20
<212> TYPE: DNA
<213> ORGANISM: Artificial Sequence
<220> FEATURE:
<223> OTHER INFORMATION: primer sequence

<400> SEQUENCE: 58
ctttggtggt gcagtagcct                                                   20

<210> SEQ ID NO 59
<211> LENGTH: 20
<212> TYPE: DNA
<213> ORGANISM: Artificial Sequence
<220> FEATURE:
<223> OTHER INFORMATION: primer sequence

<400> SEQUENCE: 59
gcatacttga aggctgtgcc                                                   20

-continued

```
<210> SEQ ID NO 60
<211> LENGTH: 20
<212> TYPE: DNA
<213> ORGANISM: Artificial Sequence
<220> FEATURE:
<223> OTHER INFORMATION: primer sequence

<400> SEQUENCE: 60
aatgtcactc cggcttctgt                                          20

<210> SEQ ID NO 61
<211> LENGTH: 21
<212> TYPE: DNA
<213> ORGANISM: Artificial Sequence
<220> FEATURE:
<223> OTHER INFORMATION: primer sequence

<400> SEQUENCE: 61
ccctgcggct aataaaccag a                                        21

<210> SEQ ID NO 62
<211> LENGTH: 21
<212> TYPE: DNA
<213> ORGANISM: Artificial Sequence
<220> FEATURE:
<223> OTHER INFORMATION: primer sequence

<400> SEQUENCE: 62
gaggatcctg tgtaacgggt g                                        21

<210> SEQ ID NO 63
<211> LENGTH: 20
<212> TYPE: DNA
<213> ORGANISM: Artificial Sequence
<220> FEATURE:
<223> OTHER INFORMATION: primer sequence

<400> SEQUENCE: 63
gccaccaaac ctgatgacct                                          20

<210> SEQ ID NO 64
<211> LENGTH: 20
<212> TYPE: DNA
<213> ORGANISM: Artificial Sequence
<220> FEATURE:
<223> OTHER INFORMATION: primer sequence

<400> SEQUENCE: 64
gctgttcagt taaccacggc                                          20

<210> SEQ ID NO 65
<211> LENGTH: 20
<212> TYPE: DNA
<213> ORGANISM: Artificial Sequence
<220> FEATURE:
<223> OTHER INFORMATION: primer sequence

<400> SEQUENCE: 65
cagacaccac ccccttttca                                          20

<210> SEQ ID NO 66
<211> LENGTH: 20
<212> TYPE: DNA
<213> ORGANISM: Artificial Sequence
<220> FEATURE:
<223> OTHER INFORMATION: primer sequence
```

<400> SEQUENCE: 66
ggtagctaga ggtgttgggc                                                    20

<210> SEQ ID NO 67
<211> LENGTH: 20
<212> TYPE: DNA
<213> ORGANISM: Artificial Sequence
<220> FEATURE:
<223> OTHER INFORMATION: primer sequence

<400> SEQUENCE: 67
aagctttcag cgaggcatta                                                    20

<210> SEQ ID NO 68
<211> LENGTH: 21
<212> TYPE: DNA
<213> ORGANISM: Artificial Sequence
<220> FEATURE:
<223> OTHER INFORMATION: primer sequence

<400> SEQUENCE: 68
ctgacatatg gatcagggcg t                                                  21

<210> SEQ ID NO 69
<211> LENGTH: 20
<212> TYPE: DNA
<213> ORGANISM: Artificial Sequence
<220> FEATURE:
<223> OTHER INFORMATION: primer sequence

<400> SEQUENCE: 69
ccactgaaaa gcccttccct                                                    20

<210> SEQ ID NO 70
<211> LENGTH: 20
<212> TYPE: DNA
<213> ORGANISM: Artificial Sequence
<220> FEATURE:
<223> OTHER INFORMATION: primer sequence

<400> SEQUENCE: 70
tgagtcccat tctcggaggt                                                    20

<210> SEQ ID NO 71
<211> LENGTH: 21
<212> TYPE: DNA
<213> ORGANISM: Artificial Sequence
<220> FEATURE:
<223> OTHER INFORMATION: primer sequence

<400> SEQUENCE: 71
ctcagaagag agatgccgag g                                                  21

<210> SEQ ID NO 72
<211> LENGTH: 22
<212> TYPE: DNA
<213> ORGANISM: Artificial Sequence
<220> FEATURE:
<223> OTHER INFORMATION: primer sequence

<400> SEQUENCE: 72
aaacagtgct aaacagtgac gc                                                 22

<210> SEQ ID NO 73
<211> LENGTH: 20

-continued

```
<212> TYPE: DNA
<213> ORGANISM: Artificial Sequence
<220> FEATURE:
<223> OTHER INFORMATION: primer sequence

<400> SEQUENCE: 73
tcgttgaaac ggagtgctga                                            20

<210> SEQ ID NO 74
<211> LENGTH: 25
<212> TYPE: DNA
<213> ORGANISM: Artificial Sequence
<220> FEATURE:
<223> OTHER INFORMATION: primer sequence

<400> SEQUENCE: 74
cattcataag gtacaatcaa cgaca                                      25

<210> SEQ ID NO 75
<211> LENGTH: 21
<212> TYPE: DNA
<213> ORGANISM: Artificial Sequence
<220> FEATURE:
<223> OTHER INFORMATION: primer sequence

<400> SEQUENCE: 75
agttccggat gtctgaaggg a                                          21

<210> SEQ ID NO 76
<211> LENGTH: 20
<212> TYPE: DNA
<213> ORGANISM: Artificial Sequence
<220> FEATURE:
<223> OTHER INFORMATION: primer sequence

<400> SEQUENCE: 76
ttggccagct agaaagcaga                                            20

<210> SEQ ID NO 77
<211> LENGTH: 21
<212> TYPE: DNA
<213> ORGANISM: Artificial Sequence
<220> FEATURE:
<223> OTHER INFORMATION: primer sequence

<400> SEQUENCE: 77
gttagccaag gttgtacccc a                                          21

<210> SEQ ID NO 78
<211> LENGTH: 20
<212> TYPE: DNA
<213> ORGANISM: Artificial Sequence
<220> FEATURE:
<223> OTHER INFORMATION: primer sequence

<400> SEQUENCE: 78
catttggtgg tgtcagcctc                                            20

<210> SEQ ID NO 79
<211> LENGTH: 20
<212> TYPE: DNA
<213> ORGANISM: Artificial Sequence
<220> FEATURE:
<223> OTHER INFORMATION: primer sequence

<400> SEQUENCE: 79
```

-continued cattccacac aacgcattcc                                                      20

<210> SEQ ID NO 80
<211> LENGTH: 21
<212> TYPE: DNA
<213> ORGANISM: Artificial Sequence
<220> FEATURE:
<223> OTHER INFORMATION: primer sequence

<400> SEQUENCE: 80
acctcttgtg tctctaaggg c                                                    21

<210> SEQ ID NO 81
<211> LENGTH: 22
<212> TYPE: DNA
<213> ORGANISM: Artificial Sequence
<220> FEATURE:
<223> OTHER INFORMATION: primer sequence

<400> SEQUENCE: 81
ccttccttta acagagccca ct                                                   22

<210> SEQ ID NO 82
<211> LENGTH: 19
<212> TYPE: DNA
<213> ORGANISM: Artificial Sequence
<220> FEATURE:
<223> OTHER INFORMATION: primer sequence

<400> SEQUENCE: 82
ggggtgagct gtccatgtg                                                       19

<210> SEQ ID NO 83
<211> LENGTH: 21
<212> TYPE: DNA
<213> ORGANISM: Artificial Sequence
<220> FEATURE:
<223> OTHER INFORMATION: primer sequence

<400> SEQUENCE: 83
aaggaagcct ccccttgttt c                                                    21

<210> SEQ ID NO 84
<211> LENGTH: 20
<212> TYPE: DNA
<213> ORGANISM: Artificial Sequence
<220> FEATURE:
<223> OTHER INFORMATION: primer sequence

<400> SEQUENCE: 84
aatgctgacc gccaagaaga                                                      20

<210> SEQ ID NO 85
<211> LENGTH: 20
<212> TYPE: DNA
<213> ORGANISM: Artificial Sequence
<220> FEATURE:
<223> OTHER INFORMATION: primer sequence

<400> SEQUENCE: 85
ccatcccgtg accagatagc                                                      20

<210> SEQ ID NO 86
<211> LENGTH: 19
<212> TYPE: DNA
<213> ORGANISM: Artificial Sequence -continued

```
<220> FEATURE:
<223> OTHER INFORMATION: primer sequence

<400> SEQUENCE: 86
gctggctagc atggtgcat                                                  19

<210> SEQ ID NO 87
<211> LENGTH: 21
<212> TYPE: DNA
<213> ORGANISM: Artificial Sequence
<220> FEATURE:
<223> OTHER INFORMATION: primer sequence

<400> SEQUENCE: 87
attgttcagc aacctgggga a                                               21

<210> SEQ ID NO 88
<211> LENGTH: 21
<212> TYPE: DNA
<213> ORGANISM: Artificial Sequence
<220> FEATURE:
<223> OTHER INFORMATION: primer sequence

<400> SEQUENCE: 88
aaggagaact ccctagcacc a                                               21

<210> SEQ ID NO 89
<211> LENGTH: 21
<212> TYPE: DNA
<213> ORGANISM: Artificial Sequence
<220> FEATURE:
<223> OTHER INFORMATION: primer sequence

<400> SEQUENCE: 89
catgaccagt gaccagtgtt g                                               21

<210> SEQ ID NO 90
<211> LENGTH: 21
<212> TYPE: DNA
<213> ORGANISM: Artificial Sequence
<220> FEATURE:
<223> OTHER INFORMATION: primer sequence

<400> SEQUENCE: 90
tcagtcatgt aacctccccc a                                               21

<210> SEQ ID NO 91
<211> LENGTH: 21
<212> TYPE: DNA
<213> ORGANISM: Artificial Sequence
<220> FEATURE:
<223> OTHER INFORMATION: primer sequence

<400> SEQUENCE: 91
aagactttgt gaaggctggg g                                               21

<210> SEQ ID NO 92
<211> LENGTH: 20
<212> TYPE: DNA
<213> ORGANISM: Artificial Sequence
<220> FEATURE:
<223> OTHER INFORMATION: primer sequence

<400> SEQUENCE: 92
aagcgcatac aacaagcaca                                                 20
```

```
<210> SEQ ID NO 93
<211> LENGTH: 20
<212> TYPE: DNA
<213> ORGANISM: Artificial Sequence
<220> FEATURE:
<223> OTHER INFORMATION: primer sequence

<400> SEQUENCE: 93
gaatcagtgt cgcgtctagc                                                  20

<210> SEQ ID NO 94
<211> LENGTH: 26
<212> TYPE: DNA
<213> ORGANISM: Artificial Sequence
<220> FEATURE:
<223> OTHER INFORMATION: target site sequence

<400> SEQUENCE: 94
cctcctgcag atcttcacca aaccgg                                           26

<210> SEQ ID NO 95
<211> LENGTH: 26
<212> TYPE: DNA
<213> ORGANISM: Artificial Sequence
<220> FEATURE:
<223> OTHER INFORMATION: target site sequence

<400> SEQUENCE: 95
agtcatccag cgccacaacc accagg                                           26

<210> SEQ ID NO 96
<211> LENGTH: 26
<212> TYPE: DNA
<213> ORGANISM: Artificial Sequence
<220> FEATURE:
<223> OTHER INFORMATION: target site sequence

<400> SEQUENCE: 96
aaccaccagg tactgcttgt ccccgg                                           26

<210> SEQ ID NO 97
<211> LENGTH: 40
<212> TYPE: DNA
<213> ORGANISM: Artificial Sequence
<220> FEATURE:
<223> OTHER INFORMATION: target site sequence

<400> SEQUENCE: 97
accatcagcg ggccggtgag tatctggctg cactgagggc                            40

<210> SEQ ID NO 98
<211> LENGTH: 40
<212> TYPE: DNA
<213> ORGANISM: Artificial Sequence
<220> FEATURE:
<223> OTHER INFORMATION: target site sequence

<400> SEQUENCE: 98
accatcagcg ggccggtgaa tatctggctg cactgagggc                            40

<210> SEQ ID NO 99
<211> LENGTH: 40
<212> TYPE: DNA
<213> ORGANISM: Artificial Sequence
<220> FEATURE:
<223> OTHER INFORMATION: target site sequence
```

-continued

<400> SEQUENCE: 99
accatcagcg ggccggtaaa tatctggctg cactgagggc                                40

<210> SEQ ID NO 100
<211> LENGTH: 40
<212> TYPE: DNA
<213> ORGANISM: Artificial Sequence
<220> FEATURE:
<223> OTHER INFORMATION: target site sequence

<400> SEQUENCE: 100
accatcagcg ggccggtaag tgtctggctg cactgagggc                                40

<210> SEQ ID NO 101
<211> LENGTH: 40
<212> TYPE: DNA
<213> ORGANISM: Artificial Sequence
<220> FEATURE:
<223> OTHER INFORMATION: target site sequence

<400> SEQUENCE: 101
accatcagcg ggccggtgag tgtctggctg cactgagggc                                40

<210> SEQ ID NO 102
<211> LENGTH: 40
<212> TYPE: DNA
<213> ORGANISM: Artificial Sequence
<220> FEATURE:
<223> OTHER INFORMATION: target site sequence

<400> SEQUENCE: 102
accatcagcg ggccggtagg tgtctggctg cactgagggc                                40

<210> SEQ ID NO 103
<211> LENGTH: 40
<212> TYPE: DNA
<213> ORGANISM: Artificial Sequence
<220> FEATURE:
<223> OTHER INFORMATION: target site sequence

<400> SEQUENCE: 103
accatcagcg ggccggtggg tgtctggctg cactgagggc                                40

<210> SEQ ID NO 104
<211> LENGTH: 40
<212> TYPE: DNA
<213> ORGANISM: Artificial Sequence
<220> FEATURE:
<223> OTHER INFORMATION: target site sequence

<400> SEQUENCE: 104
accatcagcg ggccggtaag tatctggctg cactgagggc                                40

<210> SEQ ID NO 105
<211> LENGTH: 20
<212> TYPE: DNA
<213> ORGANISM: Artificial Sequence
<220> FEATURE:
<223> OTHER INFORMATION: primer sequence

<400> SEQUENCE: 105
agctggcctt tcctagagtc                                                      20

<210> SEQ ID NO 106

```
<211> LENGTH: 20
<212> TYPE: DNA
<213> ORGANISM: Artificial Sequence
<220> FEATURE:
<223> OTHER INFORMATION: primer sequence

<400> SEQUENCE: 106
cctggaagtc aaagtgggct                                                  20

<210> SEQ ID NO 107
<211> LENGTH: 20
<212> TYPE: DNA
<213> ORGANISM: Artificial Sequence
<220> FEATURE:
<223> OTHER INFORMATION: primer sequence

<400> SEQUENCE: 107
ggctgccgga tgacaatgat                                                  20

<210> SEQ ID NO 108
<211> LENGTH: 20
<212> TYPE: DNA
<213> ORGANISM: Artificial Sequence
<220> FEATURE:
<223> OTHER INFORMATION: primer sequence

<400> SEQUENCE: 108
gggtccatgc tacagcagtt                                                  20

<210> SEQ ID NO 109
<211> LENGTH: 22
<212> TYPE: DNA
<213> ORGANISM: Artificial Sequence
<220> FEATURE:
<223> OTHER INFORMATION: primer sequence

<400> SEQUENCE: 109
cttatgcccc tgcattcctg at                                               22

<210> SEQ ID NO 110
<211> LENGTH: 19
<212> TYPE: DNA
<213> ORGANISM: Artificial Sequence
<220> FEATURE:
<223> OTHER INFORMATION: primer sequence

<400> SEQUENCE: 110
cacatctcga cgaaaccgc                                                   19

<210> SEQ ID NO 111
<211> LENGTH: 20
<212> TYPE: DNA
<213> ORGANISM: Artificial Sequence
<220> FEATURE:
<223> OTHER INFORMATION: primer sequence

<400> SEQUENCE: 111
gctcagggtc tttcgcctaa                                                  20

<210> SEQ ID NO 112
<211> LENGTH: 20
<212> TYPE: DNA
<213> ORGANISM: Artificial Sequence
<220> FEATURE:
<223> OTHER INFORMATION: primer sequence

<400> SEQUENCE: 112
```
acacccagca caagagttga                                                          20

<210> SEQ ID NO 113
<211> LENGTH: 20
<212> TYPE: DNA
<213> ORGANISM: Artificial Sequence
<220> FEATURE:
<223> OTHER INFORMATION: primer sequence

<400> SEQUENCE: 113
atgaaccaaa ccctcagcct                                                          20

<210> SEQ ID NO 114
<211> LENGTH: 25
<212> TYPE: DNA
<213> ORGANISM: Artificial Sequence
<220> FEATURE:
<223> OTHER INFORMATION: primer sequence

<400> SEQUENCE: 114
agtctgattc aaataggaga atgtc                                                    25

<210> SEQ ID NO 115
<211> LENGTH: 20
<212> TYPE: DNA
<213> ORGANISM: Artificial Sequence
<220> FEATURE:
<223> OTHER INFORMATION: primer sequence

<400> SEQUENCE: 115
tgggtaagat ttcgcaggca                                                          20

<210> SEQ ID NO 116
<211> LENGTH: 20
<212> TYPE: DNA
<213> ORGANISM: Artificial Sequence
<220> FEATURE:
<223> OTHER INFORMATION: primer sequence

<400> SEQUENCE: 116
ctgggcttga cacagattgg                                                          20

<210> SEQ ID NO 117
<211> LENGTH: 21
<212> TYPE: DNA
<213> ORGANISM: Artificial Sequence
<220> FEATURE:
<223> OTHER INFORMATION: primer sequence

<400> SEQUENCE: 117
tctgaacctt cctgatgctc c                                                        21

<210> SEQ ID NO 118
<211> LENGTH: 20
<212> TYPE: DNA
<213> ORGANISM: Artificial Sequence
<220> FEATURE:
<223> OTHER INFORMATION: primer sequence

<400> SEQUENCE: 118
ggcgtcctgg gatggttatt                                                          20

<210> SEQ ID NO 119
<211> LENGTH: 20
<212> TYPE: DNA

<213> ORGANISM: Artificial Sequence
<220> FEATURE:
<223> OTHER INFORMATION: primer sequence

<400> SEQUENCE: 119
ccttcccacc acagggtttt                                                20

<210> SEQ ID NO 120
<211> LENGTH: 21
<212> TYPE: DNA
<213> ORGANISM: Artificial Sequence
<220> FEATURE:
<223> OTHER INFORMATION: primer sequence

<400> SEQUENCE: 120
tggccttgtg ctgtgaaact a                                              21

<210> SEQ ID NO 121
<211> LENGTH: 24
<212> TYPE: DNA
<213> ORGANISM: Artificial Sequence
<220> FEATURE:
<223> OTHER INFORMATION: primer sequence

<400> SEQUENCE: 121
ttcccatgga aattctagga gacc                                           24

<210> SEQ ID NO 122
<211> LENGTH: 20
<212> TYPE: DNA
<213> ORGANISM: Artificial Sequence
<220> FEATURE:
<223> OTHER INFORMATION: primer sequence

<400> SEQUENCE: 122
ggaagtgggc agcactcaaa                                                20

<210> SEQ ID NO 123
<211> LENGTH: 21
<212> TYPE: DNA
<213> ORGANISM: Artificial Sequence
<220> FEATURE:
<223> OTHER INFORMATION: primer sequence

<400> SEQUENCE: 123
ggagaccttt ctgcccagtt g                                              21

<210> SEQ ID NO 124
<211> LENGTH: 22
<212> TYPE: DNA
<213> ORGANISM: Artificial Sequence
<220> FEATURE:
<223> OTHER INFORMATION: primer sequence

<400> SEQUENCE: 124
agaacagatt gcaagccatg aa                                             22

-continued

```
<210> SEQ ID NO 125
<211> LENGTH: 20
<212> TYPE: DNA
<213> ORGANISM: Artificial Sequence
<220> FEATURE:
<223> OTHER INFORMATION: primer sequence

<400> SEQUENCE: 125
cttcctctgt ctggtgccat                                                    20
```

IN UTERO CRISPR-MEDIATED THERAPEUTIC EDITING OF GENES

CROSS REFERENCE TO RELATED APPLICATIONS

This application is a § 371 of International Application No. PCT/US2019/030083 filed Apr. 30, 2019 which claims priority to U.S. Provisional Application 62/664,904 filed Apr. 30, 2018, the entire disclosure of each being incorporated herein by reference as though set forth in full.

GOVERNMENT INTEREST STATEMENT

This invention was made with government support under Grant numbers T32-HL007843, R01-HL118744 and R01-HL126875 awarded by the United States National Institute of Health, and Grant number UL1-TR001878 from the National Center for Advancing Translational Sciences of the NIH. The government has certain rights in the invention.

FIELD OF THE INVENTION

The invention relates to genome editing by delivering CRISPR-mediated base editor 3 (BE3) or base editor 4 (BE4) in utero to introduce a mutation, such as a nonsense codon or a missense mutation, into a gene known to cause a genetic disease. Diseases to be treated include, without limitation, enzyme deficiencies, inherited metabolic diseases and disorders of the lung.

BACKGROUND OF THE INVENTION

Advances in genome editing technology, including clustered regularly interspaced short palindromic repeats [CRISPR]-CRISPR-associated 9 (CRISPR-Cas9), present an unprecedented opportunity for targeting therapeutic genes for clinical benefit. In vivo CRISPR-Cas9-mediated homology directed repair (HDR) to correct a disease-causing mutation or non-homologous end joining (NHEJ) to disrupt a target gene or delete an unwanted segment of DNA have shown promise following postnatal application in mouse models. However, some diseases present with high prenatal or perinatal morbidity/mortality or may benefit from life-long correction of the mutation. Furthermore, inaccessible and/or non-proliferative target cells and immune responses to the viral vector and/or bacterial Cas9 transgene product present potential obstacles to achieving persistent high levels of edited cells following postnatal genome editing. In utero genome editing has the potential to overcome these limitations and treat otherwise lethal diseases.

The developing fetus has many properties that make it ideal for therapeutic genome editing. The fetus is immunologically immature and tolerant. Multiple studies of in utero gene therapy demonstrate that immune tolerance to the transgene product and lack of an immune response to the delivering viral vector are observed following prenatal viral vector delivery. This is in contrast to the development of an antibody and T cell mediated immune response to the viral vector and transgene product following postnatal gene therapy. The small size of the fetus allows high levels of viral vector carrying genome editing technology to be given per fetal weight thus maximizing the therapeutic dose. Additionally, cells of multiple organs are highly proliferative and accessible for efficient viral vector transduction during fetal development.

Finally, in utero genome editing offers the potential to target a therapeutic gene prior to disease onset or, in cases in which the target gene provides a decreased risk of disease acquisition, provide the therapeutic benefit of genome editing throughout the lifetime of the individual.

In utero genome editing has the potential to prenatally treat genetic diseases which result in significant morbidity and mortality before or shortly after birth while taking advantage of normal developmental ontogeny to enhance editing efficiency.

Accordingly, there exists a need for genome editing methods that are more effective than post-natal genomic editing: to treat a disease or disorder caused by a genetic mutation in utero to prevent morbidity and mortality before or shortly after birth while concurrently not triggering an immune response to an administered viral vector and transgene product.

SUMMARY OF THE INVENTION

The invention provides a method for in utero genome editing, the method comprising administering to a subject an adenoviral vector, wherein the subject is a fetus, the adenoviral vector comprising CRISPR-mediated base editor and a guide RNA (gRNA), the gRNA targeting a mutation in a therapeutic gene; and introducing a modified codon in the therapeutic gene by base editing the therapeutic gene, wherein the base editing is performed by the adenoviral vector.

The invention also provides a method for treating a genetic disease in a fetal subject, the method comprising: identifying in vitro a target codon for base editing; generating the adenoviral vector by cloning BE3-encoding gene, a synthetic polyadenylation sequence from pCMV-BE3, CAG reporter from pCas9_GFP, and U6 promoter-driven gRNA cassette with a protospacer sequence into a dual-expression vector; administering to the fetal subject an adenoviral vector, the adenoviral vector comprising CRISPR-mediated base editor and a guide RNA (gRNA), and the gRNA targeting a mutation in a therapeutic gene; and introducing a modified codon in the therapeutic gene by base editing the therapeutic gene, wherein the base editing is performed by the adenoviral vector. In an alternative approach, the base editor and guide RNA can be delivered in an adenovirus associated virus, such as AAV8 or AAV9. In yet another embodiment, the CRISPR-mediated editing components can be delivered on a lipid based nanoparticle.

In various embodiments, the base editor may be CRISPR-mediated base editor 3 (BE3). Alternatively, the base editor may be CRISPR-mediated base editor 4 (BE4).

Other features and advantages of the present invention will become apparent from the following detailed description, and examples. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

FIGS. 1A-1I: In utero base editing of the Pcsk9 gene. (FIG. 1A) Vitelline vein injection of E16 fetus; DOL1 liver, Ad.GFP injection (fluorescence stereomicroscopy, GFP filter). Scale bar=1 mm. (FIGS. 1B-1I) E16 Balb/c fetuses were injected with Ad.BE3.Pcsk9 or Ad.BE3.Null (ctrl).

Genomic DNA from organs of injected fetuses (FIGS. B-D; F-I) or of dams of injected fetuses (FIG. 1E) were assessed for Pcsk9 on-target (FIGS. 1B-H) and off-target (FIG. 1I) editing by Surveyor assays (FIG. 1B, D-F), Sanger sequencing (FIG. 1C), and NGS (FIGS. 1G-1I). Maternal organ analysis (FIG. 1E) occurred 1 week after fetal injection, 3 separate liver samples per mother, ctrl Li=liver DNA from injected fetus. (FIG. 1B, N=3 BE3.Pcsk9, 1 ctrl; c, representative of 4 mice replicates; d, representative of 3 mice replicates; e, representative of 2 mice replicates; f, 2 weeks: N=3 BE3.Pcsk9, 1 ctrl, 1 month: N=6 BE3.Pcsk9, 1 ctrl, 3 months: N=18 BE3.Pcsk9, 2 ctrl) (FIG. 1G) NGS, liver DNA in control mice (N=5) and at DOL1 (N=4), 2 weeks (N=3), 1 month (N=6), and 3 months of age (N=18) following in utero Ad.BE3.Pcsk9 injection; measure of centre=mean. (FIG. 1H) Frequencies of base-edited and ndel-bearing alleles, liver DNA, 3-month-old prenatal recipient of Ad.BE3.Pcsk9. Underlined bases indicate the target codon. (FIG. 1I; SEQ ID NOS: 1-10 in descending order are shown). Base editing and indel rates for the on-target and top 9 predicted off-target sites, NGS, liver DNA at 2 weeks of age from 2 prenatal Ad.BE3.Pcsk9 recipients (results separated by dashes) and a control mouse. Underlined bases indicate the base editing window based on distance from the PAM. In cases in which no base editing rates are shown, there were no C bases within the window. DOL, day of life; BE3, base editor 3; PCSK9, proprotein convertase subtilisin/kexin type 9; ctrl, control; exp; Li, liver; Lu, lung; H, heart; B, brain; K, kidney; S, spleen; arrows, Surveyor cleavage products.

FIGS. 2A-2P: Functional effects of in utero Pcsk9 base editing and comparison to postnatal editing. (FIGS. 2A-2L) E16 Balb/c fetuses were injected with Ad.BE3.Pcsk9 or Ad.BE3.Null (ctrl). (FIGS. 2A-D) Plasma PCSK9 protein levels at DOL1 (ctrl, N=10; BE3.Pcsk9, N=4), 2 weeks (ctrl, N=3; BE3.Pcsk9, N=3), 1 month (ctrl, N=31; BE3.Pcsk9, N=24), and 3 months (ctrl, N=23; BE3.Pcsk9, N=18). (FIGS. 2E, 2F) Plasma cholesterol levels at 1 (ctrl, N=31; BE3.Pcsk9, N=24) and 3 months (ctrl, N=23; BE3.Pcsk9, N=18). (FIGS. 2G, 2H) Plasma ALT levels at 1 (ctrl, N=30; BE3.Pcsk9, N=22) and 3 months (ctrl, N=23; BE3.Pcsk9, N=18). (FIGS. 2I, 2L) Liver histology (hematoxylin and eosin staining) from non-injected and Ad.BE3.Pcsk9 injected fetuses. Representative of 3 mice replicates per group per time point. Scale bar=100 μm (FIG. 2M) Ad.BE3.Pcsk9 was injected into 5-week-old B6 mice. Surveyor assays, liver genomic DNA at 1 month (N=3), 2 months (N=3), and 3 months (N=2) post-injection. (FIGS. 2O, 2P) Serum from mice injected at E16 or 5 weeks of age with Ad.BE3.Psck9 was assessed at 1 and 3 months post injection for antibodies to adenovirus (FIG. 2O) and SpCas9 (FIG. 2P) (anti-Ad: prenatal 1 month-N=11, 3 months-N=6; postnatal 1 month-N=5, 3 months-N=5; anti-SpCas9: prenatal 1 month-N=24, 3 months-N=18; postnatal 1 month-N=5, 3 months-N=6); Control non-injected, age-matched Balb/c mice (N=8). DOL, day of life; BE3, base editor 3; PCSK9, proprotein convertase subtilisin/kexin type 9; ALT, alanine aminotransferase; arrows, Surveyor cleavage products; * P=0.01; #P=0.001; $ P=0.00008; & P=0.006; % P=0.03; ** P=0.0007; ##P=0.04; $ $ P=0.02; && P=0.002. Statistical analysis performed with two-tailed Mann-Whitney U test (FIGS. 2A-D, 2G, 2H), two-tailed Student's t test (e, t=7.8, df=53; f, t=3.2; df=39) and Kruskal-Wallis test (n-p). Measure of centre=mean (FIGS. 2A-H, 2N-2P).

FIGS. 3A-3F: In utero base editing of Hpd in the Fah−/− mouse model. (FIG. 3A) Experimental scheme. (FIG. 3B) Surveyor assays to assess Hpd base editing, liver genomic DNA at DOL1, 1 month, and 3 months of age (Ad.BE3.Hpd DOL1, N=5; 1 month, N=9; 3 months, N=9) or Ad.BE3.Null (ctrl, N=1). (FIG. 3C) The percentage of base-edited Hpd on-target alleles was assessed by NGS of liver genomic DNA in fetal recipients of Ad.BE3.Null (ctrl, N=3 at DOL1 to 2 weeks of age) and Ad.BE3.Hpd at DOL1 (N=5), 1 month (N=9), and 3 months of age (N=9). Measure of centre=mean. (FIG. 3D) Frequencies of base-edited and indel-bearing alleles were assessed at 1 month of age via NGS of liver genomic DNA of prenatal Ad.BE3.Hpd recipients (N=9). Underlined bases indicate the target codon. (FIG. 3E) Genomic DNA isolated from other organs at 1 month of age (two independent mice as shown) and sperm at 3 months of age (2 independent mice as shown) was assessed by Surveyor assays for Hpd editing following prenatal Ad.BE3.Hpd injection.—ctrl=liver DNA from Ad.BE3.Null-injected fetus. (FIG. 3F; SEQ ID NOS: 11-21 in descending order are shown) NGS analysis of the Hpd on-target site and the top 10 predicted off-target sites in liver genomic DNA harvested at 1 month of age from 2 Ad.BE3.Hpd recipients and 1 Ad.BE3.Null (ctrl) recipient. BE3, base editor; HPD, hydroxyphenylpyruvate dioxygenase; NTBC, 2-(2-nitro-4-trifluoro-methylbenzyl)-1,3 cyclohexanedione, FAH, fumarylacetoacetate hydrolase; IHC, immunohistochemistry; DOL, day of life; K, kidney; H, heart; Lu, lung; B, brain; O, ovary; T, testis; L, liver; arrows, Surveyor cleavage products. Statistical analysis performed with Kruskal-Wallis test.

(FIGS. 4A, 4B) Fah−/− mice injected prenatally with Ad.BE3.Hpd (N=26) or Ad.BE3.Null (N=27) and taken off NTBC at DOL1 and non-injected Fah−/− mice maintained on NTBC (N=33) were serially weighed and followed for survival. Weight ratio represented as mean±standard error of mean. Survival statistical analysis performed with log-rank test; * P=8×10−11 for BE3.Hpd vs. BE3.Null. (FIGS. 4C-4E) Plasma ALT, total bilirubin, and AST levels were assessed at 1 month of age (or just prior to death in Ad.BE3.Null-injected mice) in Fah−/− mice injected prenatally with Ad.BE3.Hpd (N=9) or Ad.BE3.Null (N=8) and taken off NTBC at DOL1 and non-injected Fah−/− mice maintained on NTBC (N=8). (FIG. 4F, FIG. 4G) Livers of Fah−/− mice prenatally injected with Ad.BE3.Hpd and taken off NTBC at DOL1 (N=9) and non-injected Balb/c mice (N=8) were assessed for HPD staining at 1 month of age. ~100,000 to 300,000 hepatocytes were assessed per sample and the percentages of HPD-negative cells determined. Scale bar=1 mm (g, left panels) and 100 μm (g, right panels). Measure of centre=mean (a, c-f). BE3, base editor; HPD, hydroxyphenylpyruvate dioxygenase; NTBC, 2-(2-nitro-4-trifluoro-methylbenzyol)-1,3 cyclohexanedione; FAH, fumarylacetoacetate hydrolase; ALT, alanine aminotransferase; AST, aspartate aminotransferase. Statistical analysis performed with Kruskal-Wallis test (c-e) and two-tailed Mann-Whitney U test (f).

FIGS. 5A-5EE: In utero CRISPR-mediated NHEJ in the R26mTmG/+ mouse model. FIG. 5A) Schematic representation of the R26mTmG/+ genome and gRNAs targeting the loxP sites 5' and 3' to the mT gene. CRISPR mediated excision of the mT gene and NHEJ results in a 545-bp PCR product. The non-edited PCR product is 2951-bp. FIG. 5B)

E16 R26mTmG/+ fetuses were injected with AAV9.SpCas9.mTmG, AAV9.Cre, Ad.SpCas9.mTmG, or Ad.Cre, and genomic DNA was harvested from liver, heart, lung, and brain at DOL1 for PCR analysis of mTmG editing. Representative of 4 replicate mice per experimental and control groups. FIG. 5C) DOL1 liver genomic DNA of AAV9.SpCas9.mTmG, AAV9.Cre, Ad.SpCas9.mTmG, or Ad.Cre injected fetuses was analyzed by Sanger sequencing and demonstrates the expected sequence and indels following excision of the mT gene and NHEJ. Representative of 2 replicate mice per experimental and control groups. The (FIGS. 5D-I) heart, (FIGS. 5J-O) liver, (FIGS. 5P-U) lung, and (FIGS. 5V-AA) brain of non-injected R26mTmG/+ fetuses (FIGS. 5D,E,J,K,P,Q,V,W) and R26mTmG/+ fetuses injected with AAV9.SpCas9.mTmG (FIGS. 5F,G,L,M,R,S, X,Y) or Ad.SpCas9.mTmG (FIGS. 5H,I,N,O,T,U,Z,AA) were analyzed at DOL1 by fluorescent stereomicroscope (FIGS. 5D-AA) for GFP expression and by immunofluorescence (FIGS. 5BB-EE) for GFP and TdTomato expression (GFP, green; TdTomato, red; DAPI, blue). Representative of 4 replicate mice per experimental and control groups (FIGS. 5D-EE). Scale bars =1 mm (FIGS. 5D-AA) and 100 μm (FIGS. 5BB-EE). DOL, day of life; Li, liver; H, heart; Lu, lung; B, brain; NHEJ, nonhomologous end-joining.

FIGS. 6A-6Z: Organ targeting following in utero intravenous Ad.GFP injection. E16 Balb/c fetuses were injected via the vitelline vein with Ad.GFP. (FIG. 6A, H&E; FIG. 6B), GFP immunofluorescence; FIG. 6C, GFP immunoperoxidase; 10×) Histologic analysis of DOL1 livers demonstrated GFP expression. FIG. 6D, H&E; FIG. 6E, GFP immunofluorescence; FIG. 6F, GFP immunoperoxidase; 10×) Livers of 3-month-old mice continue to demonstrate GFP expression but at lower levels than DOL1 mice. (FIGS. 6G-6Z) In addition to the liver, other organs were assessed for GFP expression at DOL1. (FIGS. 6G-6K) Brain, (FIGS. 6L-6P) heart, (FIGS. 6Q-6U) lung, and (FIGS. 6V-6W) kidney; (FIGS. 6G, 6L, 6Q), 6V) brightfield, (FIGS. 6H, 6M, 6R, 6W GFP FSM, (FIGS. 6I, 6N, 6S, 6X) H&E, 20×, (FIGS. 6J, 6O, 6T, 6Y) GFP immunofluorescence, 20×, (FIGS. 6K, 6P, 6U, 6Z) GFP immunoperoxidase, 20×. FSM, fluorescent stereomicroscope; H&E, hematoxylin and eosin.

FIGS. 7A-7M: In vitro Hpd gRNA screening and in utero base editing of Hpd in wild-type mice. FIG. 7A) Tyrosine catabolic pathway highlighting the HPD enzyme, the target for base editing. FIGS. 7B and 7C) The Hpd sequence was screened for glutamine and tryptophan residues within the BE3 PAM base-editing window and thus amenable to conversion to stop codons via a C→T change (sense strand) or G→A change (antisense strand). Eight targets were identified. (FIG. 7C SEQ ID NOS: 38-45 are shown in descending order) Blue bases fall within the BE3 window. Bolded underlined bases indicate the target codon. FIG. 7D Ontarget Hpd base editing was assessed by Surveyor assays; positive activity indicated by a "+" in FIG. 7C. FIG. 7E) Experimental scheme for in utero Hpd editing in wild-type mice. FIG. 7F Surveyor assays for Hpd on-target editing, liver genomic DNA, N=7 BE3.Hpd recipients, N=1 ctrl. FIG. 7G) Sanger sequencing of liver genomic DNA from a mouse injected at E16 with Ad.BE3.Hpd. Representative of 3 replicate mice. FIG. 7H Fraction of on-target Hpd base-edited alleles, NGS of liver genomic DNA, N=7 BE3.Hpd recipients, N=1 ctrl, measure of centre=mean. FIG. 7I) Surveyor assay, genomic DNA from other organs of prenatal Ad.BE3.Hpd recipients. N=3 BE3.Hpd recipients. Negative ctrl=non-injected Balb/c 2-week-old liver genomic DNA. FIG. 7J) qRT-PCR to assess BE3 expression in indicated organs of prenatal Ad.BE3.Hpd recipients at DOL1 and non-injected, age-matched controls; N=2 noninjected Balb/c, N=2 BE3.Hpd recipients; measure of centre=mean. FIG. 7K) Liver (40×), heart (40×), lung (20×), and brain (20×) of mice prenatally injected with Ad.BE3.Hpd and non-injected controls were stained for SpCas9 to assess for BE3 expression. Representative of 3 replicate mice per group. FIG. 7L, FIG. 7M) Livers from mice prenatally injected with Ad.BE3.Hpd (N=6) and non-injected (N=1) mice harvested at 2 weeks of age and stained for HPD. Percentages of HPD-negative cells were determined in ~100,000-300,000 hepatocytes per sample, measure of centre=mean. Scale bars=100 μm FIG. 7K, 7L). BE3, base editor; FAH, fumarylacetoacetate hydrolase; HPD, hydroxyphenylpyruvate dioxygenase; IHC, immunohistochemistry; DOL, day of life; arrows, Surveyor cleavage products.

FIG. 8A) Plasma of mice injected prenatally with Ad.BE3.Hpd (N=8) or Ad.BE3.Null (N=8), or noninjected mice maintained on NTBC (N=8) was assessed for ALT, AST, and total bilirubin levels at 3 months of age. FIG. 8B) DOL1 livers from prenatal Ad.BE3.Hpd recipients and noninjected control mice were assessed by immunohistochemistry for HPD staining. Representative livers are shown. FIG. 8C) H&E staining of livers (20×) at 1 month of age from noninjected Balb/c mice, FAH−/− mice prenatally injected with Ad.BE3.Hpd and taken off NTBC at DOL1, noninjected FAH−/− mice maintained on NTBC, and FAH−/− mice prenatally injected with Ad.BE3.Null and taken off NTBC at DOL1. Samples from FAH−/− mice prenatally injected with Ad.BE3.Null were harvested at DOL17 secondary to the inability of these mice to survive to 1 month of age. BE3, base editor; HPD, hydroxyphenylpyruvate dioxygenase; NTBC, 2-(2-nitro-4-trifluoro-methylbenzyol)-1,3 cyclohexanedione; ALT, alanine aminotransferase; AST, aspartate aminotransferase; FAH, fumarylacetoacetate hydrolase; DOL, day of life. Statistical analysis performed with Kruskal-Wallis test.

FIG. 10A) E16 vitelline vein injection. FIG. 10B) Adenovirus (Ad) and (c,d) AAV8 carrying GFP transgene were injected into E16 fetuses and livers were assessed for GFP expression by fluorescent stereomicroscope (FIG. 10B, 10C) and immunohistochemistry (FIG. 10D) at birth.

FIG. 11A) Scheme of split BE3-intein fusion construct. FIG. 11B) Surveyor assay demonstrating functionality of split construct comparable to the full length BE3.

FIGS. 12A-12G. In utero gene editing via LNPs. (FIGS. 12A-12F) E16 Balb/c fetuses were injected i.v. with LNPs containing GFP mRNA (12B, 12D, 12F). Livers were assessed 5 days after injection for GFP expression by stereomicroscope (FIG. 12A-D) and IHC (FIG. 12E, 12F). Controls=age-matched uninjected fetuses (12A, 12C, 12E). (12G) Surveyor assay; Liver DNA from fetus injected with LNPs containing SpCas9 mRNA and a Pcsk9 targeting gRNA.

FIG. 14. In vitro correction of the human FAH mutation. Fah sequence around the site of the Quebec founder G→A mutation, which is indicated with underlines. In a pilot experiment, BE3 was used to introduce the Quebec mutation (and an additional G→A edit, both shown in bold) in HEK 293 cells; the guide RNA protospacer is shown with a box, the PAM in pink, and the cytosine editing window in blue. With these 293.BE3 cells, ABE7.1 was used to correct the Quebec mutation (A→G); the guide RNA protospacer is shown with a box, the PAM in pink, and the adenine editing window in blue. The most common edited alleles with correction are shown, along with their frequencies; a total of 9% of the 293.BE3 alleles had a corrected Quebec mutation. (SEQ ID NOS: 97-104 are shown in descending order)

DETAILED DESCRIPTION OF THE INVENTION

Figure 1C:
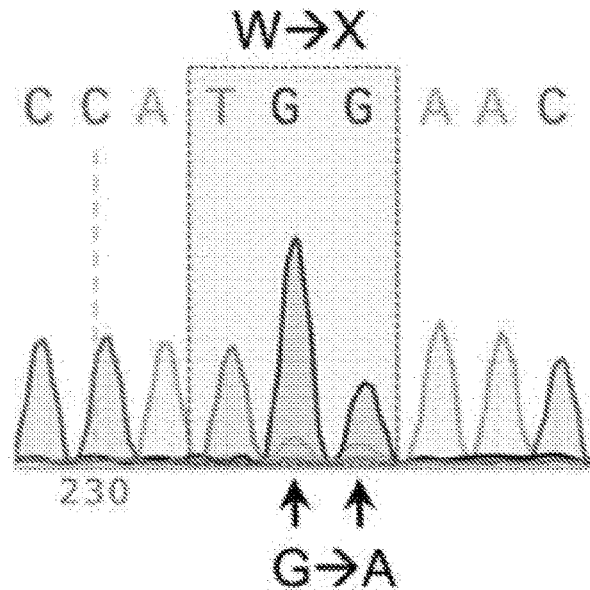

In utero genome editing can be employed to advantage to prenatally treat genetic diseases which result in significant morbidity and mortality before or shortly after birth while taking advantage of normal developmental ontogeny to enhance editing efficiency. Here we describe the delivery of the CRISPR-mediated base editor 3 in utero to introduce a nonsense codon in the Pcsk9 or Hpd gene in wild-type mice and the murine model of tyrosinemia respectively. We demonstrate long-term persistence of edited cells in both models with reduction of plasma PCSK9 and cholesterol levels following Pcsk9 silencing and rescue of the lethal phenotype and normal liver function following Hpd silencing.

The results presented herein demonstrate the ability to efficiently perform genome editing before birth and implicate a new paradigm for the treatment of select congenital genetic disorders.

The present subject matter may be understood more readily by reference to the following detailed description which forms a part of this disclosure. It is to be understood that this invention is not limited to the specific products, methods, conditions or parameters described and/or shown herein, and that the terminology used herein is for the purpose of describing particular embodiments by way of example only and is not intended to be limiting of the claimed invention.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

As employed above and throughout the disclosure, the following terms and abbreviations, unless otherwise indicated, shall be understood to have the following meanings.

In the present disclosure the singular forms "a," "an," and "the" include the plural reference, and reference to a particular numerical value includes at least that particular value, unless the context clearly indicates otherwise. Thus, for example, a reference to "a compound" is a reference to one or more of such compounds and equivalents thereof known to those skilled in the art, and so forth. The term "plurality", as used herein, means more than one. When a range of values is expressed, another embodiment includes from the one particular and/or to the other particular value. Similarly, when values are expressed as approximations, by use of the antecedent "about," it is understood that the particular value forms another embodiment. All ranges are inclusive and combinable.

As used herein, the terms "component," "composition," "composition of compounds," "compound," "drug," "pharmacologically active agent," "active agent," "therapeutic," "therapy," "treatment," or "medicament" are used interchangeably herein to refer to a compound or compounds or composition of matter which, when administered to a subject (human or animal) induces a desired pharmacological and/or physiologic effect by local and/or systemic action.

As used herein, the terms "treatment" or "therapy" (as well as different forms thereof) include preventative (e.g., prophylactic), curative or palliative treatment. As used herein, the term "treating" includes alleviating or reducing at least one adverse or negative effect or symptom of a condition, disease or disorder.

The terms "subject," "individual," and "patient" are used interchangeably herein, and refer to an animal, for example a human, to whom treatment, including prophylactic treatment, with the pharmaceutical composition according to the present invention, is provided. The term "subject" as used herein refers to human and non-human animals. The terms "non-human animals" and "non-human mammals" are used interchangeably herein and include all vertebrates, e.g., mammals, such as non-human primates, (particularly higher primates), sheep, dog, rodent, (e.g. mouse or rat), guinea pig, goat, pig, cat, rabbits, cows, horses and non-mammals such as reptiles, amphibians, chickens, and turkeys.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non nucleotide components. A polynucleotide may be further modified after polymerization, such as by conjugation with a labeling component.

As used herein the term "wild type" is a term of the art understood by skilled persons and means the typical form of an organism, strain, gene or characteristic as it occurs in nature as distinguished from mutant or variant forms. As used herein the term "variant" should be taken to mean the exhibition of qualities that have a pattern that deviates from the wild type or a comprises non naturally occurring components.

The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature.

"Complementarity" refers to the ability of a nucleic acid to form hydrogen bond(s) with another nucleic acid sequence by either traditional Watson-Crick or other nontraditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%. 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

The term "effective amount" or "therapeutically effective amount" refers to the amount of an agent that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. The term also applies to a dose that will provide an image for detection by any one of the imaging methods described herein. The specific dose may vary depending on one or more of: the particular agent chosen, the dosing regimen to be followed, whether it is administered in combination with other compounds, timing of administration, the tissue to be imaged, and the physical delivery system in which it is carried.

The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

Several aspects of the invention relate to vector systems comprising one or more vectors, or vectors as such. Vectors can be designed for expression of CRISPR transcripts (e.g. nucleic acid transcripts, proteins, or enzymes) in prokaryotic or eukaryotic cells. For example, CRISPR transcripts can be expressed in bacterial cells such as *Escherichia coli*, insect cells (using baculovirus expression vectors), yeast cells, or mammalian cells. Suitable host cells are discussed further in Goeddel, GENE EXPRESSION TECHNOLOGY: METHODS IN ENZYMOLOGY 185, Academic Press. San Diego, Calif. (1990). Alternatively, the recombinant expression vector can be transcribed and translated in vitro, for example using T7 promoter regulatory sequences and T7 polymerase.

In some embodiments, a vector is capable of driving expression of one or more sequences in mammalian cells using a mammalian expression vector. Examples of mammalian expression vectors include pCDM8 (Seed, 1987. Nature 329: 840) and pMT2PC (Kaufman, et al., 1987. EMBO J. 6: 187-195). When used in mammalian cells, the expression vector's control functions are typically provided by one or more regulatory elements. For example, commonly used promoters are derived from polyoma, adenovirus 2, cytomegalovirus, simian virus 40, and others disclosed herein and known in the art. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In some embodiments, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. Genes Dev. 1: 268-277), lymphoid-specific promoters (Calame and Eaton, 1988. Adv. Immunol. 43: 235-275), in particular promoters of T cell receptors (Winoto and Baltimore, 1989. EMBO J. 8: 729-733) and immunoglobulins (Baneiji, et al., 1983. Cell 33: 729-740; Queen and Baltimore, 1983. Cell 33: 741-748), neuron-specific promoters (e.g., the neurofilament promoter; Byrne and Ruddle, 1989. Proc. Natl. Acad. Sci. USA 86: 5473-5477), pancreas-specific promoters (Edlund, et al., 1985. Science 230: 912-916), and mammary gland-specific promoters (e.g., milk whey promoter, U.S. Pat. No. 4,873,316 and European Application Publication No. 264,166). Developmentally-regulated promoters are also encompassed, e.g., the murine hox promoters (Kessel and Gruss, 1990. Science 249: 374-379) and the α-fetoprotein promoter (Campes and Tilghman, 1989. Genes Dev. 3: 537-546).

In general, "CRISPR system" refers collectively to transcripts and other elements involved in the expression of or directing the activity of CRISPR-associated ("Cas") genes, including sequences encoding a Cas gene, a tracr (transactivating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or other sequences and transcripts from a CRISPR locus. In some embodiments, one or more elements of a CRISPR system is derived from a type I, type II, or type III CRISPR system. In some embodiments, one or more elements of a CRISPR system is derived from a particular organism comprising an endogenous CRISPR system, such as *Streptococcus pyogenes*. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. Full complementarity is not necessarily required, provided there is sufficient complementarity to cause hybridization and promote formation of a CRISPR complex. A target sequence may comprise any polynucleotide, such as DNA or RNA polynucleotides. In some embodiments, a target sequence is located in the nucleus or cytoplasm of a cell. In some embodiments, the target sequence may be within an organelle of a eukaryotic cell, for example, mitochondrion or chloroplast. A sequence or template that may be used for recombination into the targeted locus comprising the target sequences is referred to as an "editing template" or "editing polynucleotide" or "editing sequence". In aspects of the invention, an exogenous template polynucleotide may be referred to as an editing template. In an aspect of the invention the recombination is homologous recombination.

In some embodiments, one or more vectors driving expression of one or more elements of a CRISPR system are introduced into a host cell such that expression of the elements of the CRISPR system direct formation of a CRISPR complex at one or more target sites. For example, a Cas enzyme, a guide sequence linked to a tracr-mate sequence, and a tracr sequence could each be operably linked to separate regulatory elements on separate vectors. Alternatively, two or more of the elements expressed from the same or different regulatory elements, may be combined in a single vector, with one or more additional vectors providing any components of the CRISPR system not included in the first vector. CRISPR system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding a CRISPR enzyme and one or more of the guide sequence, tracr mate sequence (optionally operably linked to the guide sequence), and a tracr sequence embedded within one or more intron sequences (e.g. each in a different intron, two or more in at least one intron, or all in a single intron). In some embodiments, the CRISPR enzyme, guide sequence, tracr mate sequence, and tracr sequence are operably linked to and expressed from the same promoter.

In some embodiments, a vector comprises one or more insertion sites, such as a restriction endonuclease recognition sequence (also referred to as a "cloning site"). In some embodiments, one or more insertion sites (e.g. about or more than about 1, 2, 3, 4, 5, 6, 7, 8, 9, 10, or more insertion sites) are located upstream and/or downstream of one or more sequence elements of one or more vectors. In some embodiments, a vector comprises an insertion site upstream of a tracr mate sequence, and optionally downstream of a regulatory element operably linked to the tracr mate sequence, such that following insertion of a guide sequence into the insertion site and upon expression the guide sequence directs sequence-specific binding of a CRISPR complex to a target sequence in a eukaryotic cell. In some embodiments, a vector comprises two or more insertion sites, each insertion site being located between two tracr mate sequences so as to allow insertion of a guide sequence at each site. In such an arrangement, the two or more guide sequences may comprise two or more copies of a single guide sequence, two or more different guide sequences, or combinations of these. When multiple different guide sequences are used, a single expression construct may be used to target CRISPR activity to multiple different, corresponding target sequences within a cell. For example, a single vector may comprise about or more than about 1, 2, 3, 4, 5, 6, 7, 8, 9, 10, 15, 20, or more guide sequences. In some embodiments, about or more than about 1, 2, 3, 4, 5, 6, 7, 8, 9, 10, or more such guide-sequence-containing vectors may be provided, and optionally delivered to a cell.

In some embodiments, a vector comprises a regulatory element operably linked to an enzyme-coding sequence encoding a CRISPR enzyme, such as a Cas protein. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2. Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. These enzymes are known; for example, the amino acid sequence of *S. pyogenes* Cas9 protein may be found in the SwissProt database under accession number Q99ZW2. In some embodiments, the unmodified CRISPR enzyme has DNA cleavage activity, such as Cas9. In some embodiments the CRISPR enzyme is Cas9, and may be Cas9 from *S. pyogenes* or *S. pneumoniae*. In some embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence.

In some embodiments, a vector encodes a CRISPR enzyme that is mutated to with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand). Other examples of mutations that render Cas9 a nickase include, without limitation, H840A, N854A, and N863A. In aspects of the invention, nickases may be used for genome editing via homologous recombination.

In some embodiments, an enzyme coding sequence encoding a CRISPR enzyme is codon optimized for expression in particular cells, such as eukaryotic cells. The eukaryotic cells may be those of or derived from a particular organism, such as a mammal, including but not limited to human, mouse, rat, rabbit, dog, or non-human primate. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database", and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, Pa.), are also available. In some embodiments, one or more codons (e.g. 1, 2, 3, 4, 5, 10, 15, 20, 25, 50, or more, or all codons) in a sequence encoding a CRISPR enzyme correspond to the most frequently used codon for a particular amino acid.

In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net).

In general, a tracr mate sequence includes any sequence that has sufficient complementarity with a tracr sequence to promote one or more of: (1) excision of a guide sequence flanked by tracr mate sequences in a cell containing the corresponding tracr sequence; and (2) formation of a CRISPR complex at a target sequence, wherein the CRISPR complex comprises the tracr mate sequence hybridized to the tracr sequence. In general, degree of complementarity is with reference to the optimal alignment of the tracr mate sequence and tracr sequence, along the length of the shorter of the two sequences. Optimal alignment may be determined by any suitable alignment algorithm, and may further account for secondary structures, such as self-complementarity within either the tracr sequence or tracr mate sequence.

In some embodiments, the CRISPR enzyme is part of a fusion protein comprising one or more heterologous protein domains (e.g. about or more than about 1, 2, 3, 4, 5, 6, 7, 8, 9, 10, or more domains in addition to the CRISPR enzyme). A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-5-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). A CRISPR enzyme may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4 DNA binding domain fusions, and herpes simplex virus (HSV) BP16 protein fusions. Additional domains that may form part of a fusion protein comprising a CRISPR enzyme are described in US20110059502, incorporated herein by reference. In some embodiments, a tagged CRISPR enzyme is used to identify the location of a target sequence.

In an aspect of the invention, a reporter gene which includes but is not limited to glutathione-5-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP), may be introduced into a cell to encode a gene product which serves as a marker by which to measure the alteration or modification of expression of the gene product. In a further embodiment of the invention, the DNA molecule encoding the gene product may be introduced into the cell via a vector. In a preferred embodiment of the invention the gene product is luciferase. In a further embodiment of the invention the expression of the gene product is decreased.

In some aspects, the invention provides methods comprising delivering one or more polynucleotides, such as or one or more vectors as described herein, one or more transcripts thereof, and/or one or proteins transcribed therefrom, to a host cell. In some aspects, the invention further provides cells produced by such methods, and organisms (such as animals, plants, or fungi) comprising or produced from such cells. In some embodiments, a CRISPR enzyme in combination with (and optionally complexed with) a guide sequence is delivered to a cell. Conventional viral and non-viral based gene transfer methods can be used to introduce nucleic acids in mammalian cells or target tissues. Such methods can be used to administer nucleic acids encoding components of a CRISPR system to cells in culture, or in a host organism. Non-viral vector delivery systems include DNA plasmids, RNA (e.g. a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell. For a review of gene therapy procedures, see Anderson, Science 256:808-813 (1992); Nabel & Felgner, TIBTECH 11:211-217 (1993); Mitani & Caskey, TIBTECH 11:162-166 (1993); Dillon, TIBTECH 11:167-175 (1993); Miller, Nature 357:455-460 (1992); Van Brunt, Biotechnology 6(10):1149-1154 (1988); Vigne, Restorative Neurology and Neuroscience 8:35-36 (1995); Kremer & Perricaudet, British Medical Bulletin 51(1):31-44 (1995); Haddada et al., in Current Topics in Microbiology and Immunology Doerfler and Bihm (eds) (1995); and Yu et al., Gene Therapy 1:13-26 (1994).

Methods of non-viral delivery of nucleic acids include lipofection, nucleofection, microinjection, biolistics, virosomes, liposomes, immunoliposomes, polycation or lipid:

nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Feigner, WO 91/17424; WO 91/16024. Delivery can be to cells (e.g. in vitro or ex vivo administration) or target tissues (e.g. in vivo administration).

The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485, 054, 4,501,728, 4,774,085, 4,837,028, and 4,946,787).

The use of RNA or DNA viral based systems for the delivery of nucleic acids take advantage of highly evolved processes for targeting a virus to specific cells in the body and trafficking the viral payload to the nucleus. Viral vectors can be administered directly to patients (in vivo) or they can be used to treat cells in vitro, and the modified cells may optionally be administered to patients (ex vivo). Conventional viral based systems could include retroviral, lentivirus, adenoviral, adeno-associated and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al., J. Virol. 66:2731-2739 (1992); Johann et al., J. Virol. 66:1635-1640 (1992); Sommnerfelt et al., Virol. 176:58-59 (1990); Wilson et al., J. Virol. 63:2374-2378 (1989); Miller et al., J. Virol. 65:2220-2224 (1991); PCT/US94/05700). In applications where transient expression is preferred, adenoviral based systems may be used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors may also be used to transduce cells with target nucleic acids, e.g., in the in vitro production of nucleic acids and peptides, and for in vivo and ex vivo gene therapy procedures (see, e.g., West et al., Virology 160:38-47 (1987); U.S. Pat. No. 4,797,368; WO 93/24641; Kotin, Human Gene Therapy 5:793-801 (1994); Muzyczka, J. Clin. Invest. 94:1351 (1994). Construction of recombinant AAV vectors are described in a number of publications, including U.S. Pat. No. 5,173,414; Tratschin et al., Mol. Cell. Biol. 5:3251-3260 (1985); Tratschin, et al., Mol. Cell. Biol. 4:2072-2081 (1984); Hermonat & Muzyczka, PNAS 81:6466-6470 (1984); and Samulski et al., J. Virol. 63:03822-3828 (1989).

Packaging cells are typically used to form virus particles that are capable of infecting a host cell. Such cells include 293 cells, which package adenovirus, and ψ2 cells or PA317 cells, which package retrovirus. Viral vectors used in gene therapy are usually generated by producing a cell line that packages a nucleic acid vector into a viral particle. The vectors typically contain the minimal viral sequences required for packaging and subsequent integration into a host, other viral sequences being replaced by an expression cassette for the polynucleotide(s) to be expressed. The missing viral functions are typically supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences. The cell line may also be infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In some embodiments, a host cell is transiently or non-transiently transfected with one or more vectors described herein. In some embodiments, a cell is transfected as it naturally occurs in a subject. In some embodiments, a cell that is transfected is taken from a subject. In some embodiments, the cell is derived from cells taken from a subject, such as a cell line.

In one aspect, the invention provides for methods of modifying a target polynucleotide in a eukaryotic cell, which may be in vivo, ex vivo or in vitro. In some embodiments, the method comprises sampling a cell or population of cells from a human or non-human animal, and modifying the cell or cells. Culturing may occur at any stage ex vivo. The cell or cells may be re-introduced into the human or non-human animal.

In one aspect, the invention provides for methods of modifying a target polynucleotide in a eukaryotic cell. In some embodiments, the method comprises allowing a CRISPR complex to bind to the target polynucleotide to effect cleavage of said target polynucleotide thereby modifying the target polynucleotide, wherein the CRISPR complex comprises a CRISPR enzyme complexed with a guide sequence hybridized to a target sequence within said target polynucleotide, wherein said guide sequence is linked to a tracr mate sequence which in turn hybridizes to a tracr sequence.

In one aspect, the invention provides kits containing any one or more of the elements disclosed in the above methods and compositions. In some embodiments, the kit comprises a vector system or components for an alternative delivery system such as those described above and instructions for using the kit. In some embodiments, the vector or delivery system comprises (a) a first regulatory element operably linked to a tracr mate sequence and one or more insertion sites for inserting a guide sequence upstream of the tracr mate sequence, wherein when expressed, the guide sequence directs sequence-specific binding of a CRISPR complex to a target sequence in a eukaryotic cell, wherein the CRISPR complex comprises a CRISPR enzyme complexed with (1) the guide sequence that is hybridized to the target sequence, and (2) the tracr mate sequence that is hybridized to the tracr sequence; and/or (b) a second regulatory element operably linked to an enzyme-coding sequence encoding said CRISPR enzyme comprising a nuclear localization sequence. Elements may be provided individually or in combinations, and may be provided in any suitable container, such as a vial, a bottle, or a tube. In some embodiments, the kit includes instructions in one or more languages, for example in more than one language.

In some embodiments, a kit comprises one or more reagents for use in a process utilizing one or more of the elements described herein. Reagents may be provided in any suitable container. For example, a kit may provide one or more reaction or storage buffers. Reagents may be provided in a form that is usable in a particular assay, or in a form that requires addition of one or more other components before use (e.g. in concentrate or lyophilized form). A buffer can be any buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In some embodiments, the buffer has a pH from about 7 to about 10. In some embodiments, the kit comprises one or more oligonucleotides corresponding to a guide sequence for insertion into a vector so as to operably link the guide sequence and a regulatory element. In some embodiments, the kit comprises a homologous recombination template polynucleotide.

In one aspect, the invention provides methods for using one or more elements of a CRISPR system. The CRISPR complex of the invention provides an effective means for modifying a target polynucleotide. The CRISPR complex of the invention has a wide variety of utility including modifying (e.g., deleting, inserting, translocating, inactivating, activating) a target polynucleotide in a multiplicity of cell types in methods of gene therapy. An exemplary CRISPR complex comprises a CRISPR enzyme complexed with a guide sequence hybridized to a target sequence within a target polynucleotide. The guide sequence is linked to a tracr mate sequence, which in turn hybridizes to a tracr sequence.

As used herein, the term a "metabolic gene" is defined as an inherited single gene anomaly, i.e., a single gene coding for an enzyme is defective, and that defect causes an enzyme deficiency. The enzyme deficiency produces an inherited metabolic disease or disorder, of which a subtype is an inborn error of metabolism. Most single gene anomalies are autosomal recessive, i.e., two copies of the defective gene must be present for the disease or trait to develop. Non-limiting examples of metabolic include glucose metabolism disorders, lipid metabolism disorders, malabsorption syndromes, metabolic brain diseases, calcium metabolism disorders, DNA repair-deficiency disorders, hyperlactemia, iron metabolism disorders, metabolic syndrome X, inborn error of metabolism, phosphorus metabolism disorders, and acid-base imbalance. Inherited metabolic diseases previously were classified as disorders of carbohydrate metabolism, amino acid metabolism, organic acid metabolism, or lysosomal storage diseases, however new inherited disorders of metabolism have been discovered and the categories have multiplied. Certain major classes of congenital metabolic diseases include disorders of carbohydrate metabolism, e.g., glycogen storage disease, glucose-6-phosphate dehydrogenase (G6PD) deficiency (resulting from a mutation in the G6PD gene); disorders of amino acid metabolism, e.g., phenylketonuria, maple syrup urine disease, glutaric acidemia type 1; urea cycle disorder (Urea Cycle Defects), e.g., carbamoyl phosphate synthetase I deficiency; disorders of organic acid metabolism (organic acidurias), e.g., alcaptonuria, 2-hydroxyglutaric acidurias; disorders of fatty acid oxidation and mitochondrial metabolism; e.g., medium-chain acyl-coenzyme A dehydrogenase deficiency (often called "MCADD") (caused by mutations in the ACADM gene, which results in medium-chain fatty acids not being metabolized properly and leads to lethargy and hypoglycemia); disorders of porphyrin metabolism, e.g., acute intermittent porphyria; disorders of purine or pyrimidine metabolism, e.g., Lesch-Nyhan syndrome (caused by mutations in the hypoxanthine phosphoribosyltransferase 1 (HPRT1) gene and is inherited in an X-linked recessive manner; disorders of steroid metabolism, e.g., lipoid congenital adrenal hyperplasia, congenital adrenal hyperplasia; disorders of mitochondrial function, e.g., Kearns-Sayre syndrome; disorders of peroxisomal function, e.g., Zellweger syndrome (caused by mutations in genes encoding peroxins, e.g., PEX1, PEX2, PEX3, PEX5, PEX6, PEX10, PEX12, PEX13, PEX14, PEX16, PEX19, or PEX26 genes); lysosomal storage disorders, e.g., Gaucher's disease (of which there are three subtypes, all of which are autosomal recessive) and Niemann-Pick disease (has an autosomal recessive inheritance pattern; Niemann-Pick types A and B are caused by a mutation in the Sphingomyelin phosphodiesterase 1 (SMPD1) gene; mutations in NPC1 gene or NPC2 gene cause Niemann-Pick disease, type C (NPC), which affects a protein used to transport lipids; Niemann-Pick type D shares a specific mutation in the NPC1 gene, patients having type D shared a common Nova Scotian ancestry).

The invention provides a method for in utero genome editing, the method comprising: administering to a subject an adenoviral vector, wherein the subject is a fetus, the adenoviral vector comprising CRISPR-mediated base editor 3 (BE3) and a guide RNA (gRNA), the gRNA targeting a mutation in a therapeutic gene; and introducing a modified codon in the therapeutic gene by base editing the therapeutic gene, wherein the base editing is performed by the adenoviral vector. Base editing addresses the disadvantage of the need to create double strand breaks (DSBs) to instigate NHEJ or HDR. The base editor can comprise a catalytically impaired *Streptococcus pyogenes* Cas9 (SpCas9) protein, unable to make DSBs, fused to either a cytosine deaminase domain from a nucleic acid-editing protein (CBE) or a modified tRNA adenosine deaminase (ABE). The SpCas9 and gRNA tether the base editor at the genome target site, and the cytosine deaminase converts a nearby cytosine into uracil and, ultimately, thymine (resulting in either C→T or G→A changes in the coding sequence of a gene, depending on which strand is targeted). The cytosine deaminase can introduce nonsense mutations in a site-specific fashion. Alternatively, the adenine deaminase converts a nearby adenine into inosine and, ultimately, guanine and can correct a disease-causing G→A mutation. Unlike HDR, base editing does not require proliferating cells to efficiently introduce mutations.

In an embodiment, the method further comprises before step (a): identifying in vitro a target codon for base editing into a nonsense codon; and generating the adenoviral vector by cloning BE3-encoding gene, a synthetic polyadenylation sequence from pCMV-BE3, CAG reporter from pCas9_GFP, and U6 promoter-driven gRNA cassette with a protospacer sequence into a dual-expression vector.

In various embodiments, the herein provided genome editing is performed in utero when the fetus is inside a uterus of its carrier and the uterus is inside the body of a living carrier. In embodiments, the carrier may be a mammal. In certain embodiments, the mammal may be an animal. In additional embodiments, the mammal may be human. The living carrier may be the mother of the fetus or a surrogate.

In further embodiments, the herein provided genome editing is performed in utero when the fetus is inside a uterus, and the uterus is outside the body of a carrier, e.g., not within the body of any living carrier, for example the uterus is in vitro or in an alternate embodiment, the uterus is ex vivo.

In certain embodiments, the target codon is screened for a glutamine residue and a tryptophan residue, wherein the glutamine and tryptophan residues are within a base editing window of a protospacer adjacent motif (PAM) of the BE3, wherein the window is flanked by four proximal and four distal bases, wherein the proximal and distal bases match reference sequences.

In alternate embodiments, the CRISPR-mediated base editor is base editor 4 (BE4) rather than BE3.

In some embodiments, the method further comprises assessing C bases within the window for a change to another base. In embodiments, the gRNA is selected if the BE3 PAM sequence (NGG) is 13-17 nucleotides distal to the target cytosine base(s). In particular embodiments, the change is via a C to T on a sense strand, and the modified codon is changed to a nonsense codon. In additional embodiments, the change is via a G to A on an antisense strand, and the modified codon is changed to a nonsense codon. In further embodiments, the change is via a C to T on a sense strand, and the change is a missense variant. In additional embodiments, the change is via a G to A on an antisense strand, and the change is a missense variant. The base editing may occur prior to disease onset, wherein the disease is a phenotype resulting from a mutation in the therapeutic gene. In certain embodiments, the base editing decreases a risk of developing a disease.

In other embodiments, the therapeutic gene is a proprotein convertase subtilisin/kexin type 9 (PCSK9) gene. In such embodiments, the protospacer has nucleic acid sequence 5'-CAGGTTCCATGGGATGCTCT-3'. In particular embodiments, the introduction of a modified codon, wherein the modified codon is a nonsense codon, in the PCSK9 gene reduces plasma cholesterol levels in the subject postnatally. The reduced plasma cholesterol levels comprise a long-term reduction, wherein the long-term reduction is effected by sustained cells comprising the introduced modified codon. The reduced plasma cholesterol levels reduce a risk of coronary heart disease.

In some embodiments, the therapeutic gene is a 4-hydroxyphenylpyruvate dioxygenase (Hpd) gene. In these embodiments, the protospacer has nucleic acid sequence 5'-CATTCAACGTCACAACCACC-3' (SEQ ID NO: 36). In various embodiments, the introduction of a modified codon, wherein the modified codon is a nonsense codon, in the Hpd gene effects a permanent gene knockout of the Hpd gene. In embodiments, the permanent Hpd gene knockout restores normal liver function in the subject prior to birth. In additional embodiments, the permanent Hpd gene knockout treats hereditary tyrosinemia type I (HT1) disorder in the subject prior to birth.

The invention also provides a method for treating a genetic disease in a fetal subject, the method comprising: identifying in vitro a target codon for base editing; generating the adenoviral vector by cloning BE3-encoding gene, a synthetic polyadenylation sequence from pCMV-BE3, CAG reporter from pCas9_GFP, and U6 promoter-driven gRNA cassette with a protospacer sequence into a dual-expression vector; administering to the fetal subject an adenoviral vector, the adenoviral vector comprising CRISPR-mediated base editor 3 (BE3) and a guide RNA (gRNA), and the gRNA targeting a mutation in a therapeutic gene; and introducing a modified codon in the therapeutic gene by base editing the therapeutic gene, wherein the base editing is performed by the adenoviral vector.

In alternate embodiments, the CRISPR-mediated base editor is base editor 4 (BE4) instead of BE3. In certain embodiments, the target codon is screened for a glutamine residue and a tryptophan residue, wherein the glutamine and tryptophan residues are within a base editing window of a protospacer adjacent motif (PAM) of the BE3, wherein the window is flanked by four proximal and four distal bases, wherein the proximal and distal bases match reference sequences.

In some embodiments, the method further comprises assessing C bases within the window for a change to another base. In further embodiments, the gRNA is selected if the BE3 PAM sequence (NGG) is 13-17 nucleotides distal to the target cytosine base(s). In various embodiments, the change is via a C to T on a sense strand, and the modified codon is changed to a nonsense codon. In other embodiments, the change is via a G to A on an antisense strand, and the modified codon is changed to a nonsense codon. In further embodiments, the change is via a C to T on a sense strand, and the change is a missense variant. In additional embodiments, the change is via a G to A on an antisense strand, and the change is a missense variant. In certain embodiments, the base editing occurs prior to disease onset, wherein the disease is a phenotype resulting from the mutation in the therapeutic gene. The base editing may decrease a risk of developing a disease.

In some embodiments, the herein provided method for treating a genetic disease in a fetal subject via genome editing is performed in utero wherein the fetus is inside a uterus of its carrier and the uterus is inside the body of a living carrier. In other embodiments, the carrier may be a mammal. In certain embodiments, the mammal may be an animal. In additional embodiments, the mammal may be human. The living carrier may be the mother of the fetus or a surrogate.

In further embodiments, the herein provided method for treating a genetic disease in a fetal subject via genome editing is performed in utero wherein the fetus is inside a uterus, and the uterus is outside the body of a carrier, e.g., not within the body of any living carrier, for example the uterus is in vitro or in an alternate embodiment, the uterus is ex vivo.

In some embodiments, the therapeutic gene is a beta thalassemia (HBB) gene. In these embodiments, the introduction of a modified codon in the HBB gene, effects production of beta-globin in the subject prior to birth.

In other embodiments, the therapeutic gene is a Huntington (HTT) gene. In certain embodiments, the introduction of a modified codon in the HTT gene effects production of huntingtin in the subject prior to birth.

In various embodiments, the therapeutic gene is a 3-beta (β)-hydroxysteroid dehydrogenase (HSD3B2) gene. In embodiments, the introduction of a modified codon in the HSD3B2 gene effects production of 3β-HSD in the subject prior to birth.

In additional embodiments, the therapeutic gene is a gap junction protein beta 2 (GJB2) gene. In embodiments, the introduction of a modified codon in the GJB2 gene effects production of gap junction beta 2 in the subject prior to birth.

In further embodiments, the therapeutic gene is a C-C motif chemokine receptor 5 (CCR5) gene. In embodiments, the introduction of a modified codon in the CCR5 gene effects defective alleles which confer HIV infection resistance in the subject prior to birth.

In various embodiments, the therapeutic gene is a fibrillin 1 (FBN1) gene. In embodiments, the introduction of a modified codon in the FBN1 gene effects production of fibrillin-1 in the subject prior to birth.

In still further embodiments, the therapeutic gene is a fragile X mental retardation 1 (FMR1) gene. In embodiments, the introduction of a modified codon in the FMR1 gene effects production of FMRP in the subject prior to birth.

In some embodiments, the therapeutic gene is base edited in an embryo, wherein prior to implantation of the embryo in a subject, wherein the embryo is in vitro fertilized.

Examples

The inventors sought to establish the feasibility of prenatal genome editing through the application of CRISPR-Cas9 genome editing or base editing. The inventors initially established the ability to use CRISPR-Cas9 for standard genome editing in the fetal liver in mice. We then used in utero base editing with the base editor 3 (BE3), which can make site-specific C→T or G→A edits in the sense and anti-sense DNA strand respectively, to introduce nonsense mutations in the target genes in two clinically relevant mouse models—the first, a preventive health model for coronary heart disease; the second, the congenital metabolic disorder hereditary tyrosinemia type I (HT1).

Coronary heart disease is the leading cause of death worldwide. Loss-of-function mutations in proprotein convertase subtilisin/kexin type 9 (PCSK9) reduce plasma cholesterol levels and risk of coronary heart disease without serious adverse consequences. Previous studies have demonstrated the feasibility of CRISPR-Cas9 mediated NHEJ to disrupt PCSK9 orthologs in mouse and human hepatocytes in vivo postnatally. More recently, we have demonstrated the ability to use postnatal in vivo base editing to efficiently introduce a nonsense mutation into the Pcsk9 gene, with subsequent reduction in plasma PCSK9 protein and cholesterol levels at short-term time points. In the current study, we evaluated if in utero base editing of murine Pcsk9 is associated with long-term improvement in plasma PCSK9 and cholesterol levels.

The inventors then extended the proof-of-principle studies to the more clinically relevant disease model of tyrosinemia. HT1 is an autosomal recessive disease with a worldwide incidence of 1:100,000, but with prevalence rates as high as 1:16,000 and 1:1,850 in Quebec and the Saguenay-Lac Saint-Jean regions of Canada respectively. It is caused by a deficiency in fumarylacetoacetate hydrolase (FAH), which results in the accumulation of the toxic metabolites fumarylacetoacetate, succinylacetone, and maleylacetoacetate in the liver and kidney. Affected fetuses can be diagnosed with HT1 by mutation analysis in the first trimester of pregnancy. The acute form of the disease presents prior to 2 months of age and is characterized by severe liver failure, abnormal blood coagulation, and hypoglycemia resulting in death within the first months of life. Current management of HT1, aside from liver transplant, is limited to lifelong administration of the drug 2-(2-nitro-4-trifluoro-methylbenzyol)-1,3 cyclohexanedione (NTBC) which inhibits hydroxyphenylpyruvate dioxygenase (HPD), an enzyme upstream of FAH in the tyrosine catabolic pathway, thereby preventing the accumulation of toxic metabolites. As an alternative to NTBC, the inventors hypothesized that in utero base editing to introduce a nonsense mutation in the Hpd gene would result in permanent gene knockout prior to birth, thus serving as a one-time treatment for tyrosinemia. As such, we evaluated in utero base editing as a therapeutic approach to rescue the lethal phenotype in the murine model of HT1. In the examples below, we demonstrate the feasibility and advantages of in utero genome editing and compare it to postnatal genome editing. Specifically, long-term reduction in plasma PCSK9 protein and total cholesterol levels were achieved following prenatal silencing of the Pcsk9 gene and normal liver function with rescue of the lethal HT1 phenotype was achieved following prenatal Hpd silencing.

Methods

Screening and Selection of Guide RNAs gRNAs targeting the mouse Pcsk9 and Hpd genes were screened in vitro in Neuro-2a cells (N2a) for base editing activity via Surveyor assay or Sanger sequencing as previously described. Specifically, the protospacer and protospacer adjacent motif (PAM) (CAGGTTCCATGG-GATGCTCT_GGG; SEQ ID NO: 1) previously demonstrated to target the mouse Pcsk9 gene at W159 were used in the current study. Screening and selection of the gRNAs targeting the mouse Hpd gene involved a similar protocol. pCMV-BE3 was a gift from David Liu (Addgene plasmid #73021). The mouse Hpd sequence was visually inspected and codons that could be potentially base edited into nonsense codons were identified. gRNAs were selected if the BE3 PAM sequence (NGG) was 13-17 nucleotides distal to the target cytosine base(s). If base editing resulted in a nonsense codon in an appreciable number of alleles (as indicated by the height of the alternative base peak on Sanger sequencing) the gRNA was designated "+". The protospacer and PAM sequences screened, and corresponding target codon are listed in Table 1. For the R26mTmG/+ mouse model, gRNAs targeting the loxP sites flanking the mT gene were selected based on their predicted high on-target efficiency and low off-target effects as determined by the online tool crispr.mit.edu. The protospacer and PAM used to target the loxP sites in the current studies was ACATTATACGAAGTTATATTAA_GGG (SEQ ID NO:37).

TABLE 1

| Hpd sites screened for editing via Surveyor assay in vitro in N2a cells. (SEQ ID NOS: 38-45 are shown in descending order. | | |
|---|---|---|
| target | protospacer | PAM |
| W25 | CAACCCAGAAGGTCACCGAG | TGG |
| Q31 | TGCCAAGCAGGTAGAGAGGC | TGG |
| Q108 | TTGTGCAGGTGAGAAACATT | CGG |
| Q125 | GGAGCAAGACAAATTTGGGA | AGG |
| Q194 | AAATGCAGTCTGCCTCAGAA | TGG |
| Q205 | ACCTGCAGTTCCACCGGTTC | TGG |
| Q309 | GATCCAGGTGAAAGAGAGCA | TGG |
| Q352 | CATTCAACGTCACAACCACC | AGG |

Generation of Adenovirus Vectors

The BE3-encoding gene and synthetic polyadenylation sequence from pCMV-BE3, the CAG reporter from pCas9_GFP (Addgene plasmid #44719), and the U6 promoter-driven gRNA cassette from pGuide (Addgene plasmid #64711) with the protospacer sequence 5'-CAGGTTC-CATGGGATGCTCT-3' (SEQ ID NO: 46) (for Pcsk9 studies), the protospacer sequence 5'-CATTCAACGT-CACAACCACC-3' (SEQ ID NO: 47) (for the Hpd studies), or the protospacer sequence 5'-GGTGCTAGCCTTGCGTTCCG-3' (SEQ ID NO: 48) (control studies: irrelevant protospacer not matching any sequence in the mouse genome) were cloned into pDUAL-Basic expression vector. For R26mTmG/+ experiments, which used SpCas9 and not the BE3, the mTmG protospacer (5'-ACATTATACGAAGTTATATTAA-3'; SEQ ID NO:49) was cloned into plasmid pX330-U6-Chimeric_BB-CBhhSp-Cas9 (a gift from Feng Zhang; Addgene plasmid #42230). Vector Biolabs (Malvern, PA) used these constructs to generate recombinant adenovirus type 5 particles. Premade adenovirus type 5 particles containing the GFP transgene or Cre recombinase under a CMV promoter were purchased from Vector Biolabs. Ad viral vectors are referred to as Ad.BE3.Pcsk9, Ad.BE3.Hpd, Ad.BE3.Null, Ad.SpCas9.mTmG, Ad.GFP, and Ad.Cre and the titers are indicated in Table 2.

TABLE 2

| Viral Vector Titers. | |
| --- | --- |
| Viral vector | PFU titer (IFU/mL) |
| Ad.BE3.Pcsk9 | $3.9 \times 10^{10}$ |
| Ad.BE3.Hpd | $4.8 \times 10^{10}$ |
| Ad.BE3.Null | $5.7 \times 10^{10}$ |
| Ad.SpCas9.mTmG | $1.2 \times 10^{11}$ |
| Ad.GFP | $1.0 \times 10^{10}$ |
| Ad.Cre | $1.0 \times 10^{10}$ |

Animals

Balb/c, C57B1/6 (called B6), B6.129(Cg)-Gt (ROSA)$^{26Sortm4(ACTB-tdTomato,-EGFP)Luo}$/J (called R26mTmG/+; stock #007676), and Fah$^{1R}$Tyr$^c$/RJ (called FAH; stock #018129) mice were purchased from Jackson Laboratories (Bar Harbor, ME). FAH mice were provided as heterozygotes and subsequently bred to homozygosity (Fah$^{-/-}$) in our animal facility and maintained on nitisinone (NTBC, CAS #104206-65-7, Yecuris) in their drinking water at a concentration of 16.5 mg/L. NTBC was removed from experimental animals and continued on control animals as indicated. Animals were housed in the Laboratory Animal Facility of the Abramson Research Center and the Colket Translational Research Building at The Children's Hospital of Philadelphia (CHOP). The experimental protocols were approved by the Institutional Animal Care and Use Committee at CHOP and followed guidelines set forth in the National Institutes of Health's *Guide for the Care and Use of Laboratory Animals*.

Genotyping

FAH mice were genotyped to confirm the Fah$^{-/-}$ genotype. At weaning or the time of sacrifice, 2 mm tail snips were placed in 100 μL of 1× Lysis buffer (50× Lysis buffer: 1.25M NaOH, 10 mM EDTA) and incubated at 95° C. for 1 hour. 100 μL of Neutralization buffer (50× Neutralization buffer: 2M tris-HCl) was then added and samples were vortexed. Extracted DNA was amplified using primers Fah-F (TCTCCCCCGCACTTAGTTTCC; SEQ ID NO: 50) and Fah-R (GGACTCAGATGCTGGGCTGATG; SEQ ID NO: 51) and PCR products were digested with the BsrBI restriction enzyme (#R0102, New England BioLabs) according to the manufacturer's instructions. Digested samples were run on ethidium-bromide stained 1.2% agarose gels for analysis. The mutated Fah allele loses the BsrBI cut site. The genotype was also confirmed with Sanger sequencing.

In Utero and Postnatal Mouse Injections

Intravenous in utero injections were performed as previously described Fetuses of time-dated Balb/c, Fah$^{-/-}$, and R26$^{mTmG/mTmG}$×B6 (to generate R26$^{mTmG/+}$ fetuses) mice were injected at gestational day (E) 16. Under isoflurane anesthesia and after providing local anesthetic (0.25% bupivacaine subcutaneously), a midline laparotomy was made and the uterine horn exposed. The vitelline vein, which runs along the uterine wall and enters the portal circulation resulting in first-pass effect to the liver and systemic delivery via the ductus *venosus*, was identified under a dissecting microscope and 10 μL of virus ($1 \times 10^8$-$1 \times 10^9$ viral particles) was injected per fetus using a 100 μm beveled glass micropipette. A successful injection was confirmed by temporary clearance of the blood from the vein and absence of extravasation of the injectate. The uterus was then returned to the abdominal cavity and the laparotomy incision was closed in a single layer with 4-0 Vicryl suture. Viral injections into adult mice (Balb/c and B6 mice for Pcsk9 studies) were performed via the retroorbital vein under isoflurane anesthesia. A total volume of 200 μL was injected such that ~$4 \times 10^9$ viral particles were injected per mouse.

Screening Balb/c and R26$^{mTmG/+}$ Animal Studies

E16 Balb/c fetuses were injected via the vitelline vein with $1 \times 10^8$ Ad.GFP particles. Livers of injected mice were assessed on DOL1 and 3 months of age by fluorescent stereomicroscopy and immunohistochemistry for GFP expression. Similarly, the brain, heart, lungs, and kidney of injected mice were assessed for GFP expression on DOL1.

E16 R26$^{mTmG/+}$ fetuses were injected via the vitelline vein with $1 \times 10^9$ Ad.SpCas9.mTmG or $1 \times 10^8$ Ad.Cre particles. Injected mice were sacrificed on DOL1 (5 days post injection) and the liver, heart, lung, and brain were isolated. A portion of each organ was used to extract genomic DNA using the DNeasy blood and tissue kit (QIAGEN) as per the manufacturer's instructions and the remainder of the organ was used to assess GFP and TdTomato expression by immunohistochemistry. Genomic DNA was assessed for editing by Sanger sequencing and by PCR analysis using primers (Table 3) flanking the protospacer sequences within the loxP sites such that successful editing resulted in amplification of a 545-base pair band while unsuccessful editing yielded a 2951-base pair band.

TABLE 3

Primers used for Surveyor assays, mTmG PCR, and
Sanger sequencing (SEQ ID NOS: 52-70 are shown
in descending order)

| target | primer | | experiment |
|---|---|---|---|
| Hpd W25 & Q31 | forward reverse | TGAGTCCCATTCTCGGAGGT CCACTGAAAAGCCCTTCCCT | Hpd in vitro screening |
| Hpd Q108 | forward reverse | CTGACATATGGATCAGGGCGT AAGCTTTCAGCGAGGCATTA | Hpd in vitro screening |
| Hpd Q125 | forward reverse | GGTAGCTAGAGGTGTTGGGC CAGACACCACCCCCTTTTCA | Hpd in vitro screening |
| Hpd Q194 | forward reverse | GCTGTTCAGTTAACCACGGC GCCACCAAACCTGATGACCT | Hpd in vitro screening |
| Hpd Q205 | forward reverse | GAGGATCCTGTGTAACGGGTG CCCTGCGGCTAATAAACCAGA | Hpd in vitro screening |
| Hpd Q309 | forward reverse | AATGTCACTCCGGCTTCTGT GCATACTTGAAGGCTGTGCC | Hpd in vitro screening |
| Hpd Q352 | forward reverse | CTTTGGTGGTGCAGTAGCCT CATGTGTGGATGGGGGCTTA | Hpd in vitro screening & in vivo studies |
| Pcsk9 W159 | forward reverse | TTCAGGGGCTGGAGTTACGG AGAGAGCACAGAGAGGTCAGT | Pcsk9 in vivo studies |
| mTmG | forward reverse | AAATCTGTGCGGAGCCGAAATC CCTGTCCGTTCGCTTTGGAAG | mTmG PCR & Sanger sequence analysis |

Pcsk9 Animal Studies

Prenatal experiments: E16 Balb/c fetuses were injected with $4\times10^8$ Ad.BE3.Pcsk9 or $6\times10^8$ Ad.BE3.Null particles via the vitelline vein. Injected mice were subsequently sacrificed at DOL1, 2 weeks, 1 month, and 3 months of age. Plasma was collected at the time of sacrifice from all mice and at 1 month for mice sacrificed at 3 months of age. Prior to sacrifice and/or plasma isolation mice were fasted for 4 hours. At the time of sacrifice genomic DNA was isolated from a portion of the liver, heart, lung, brain, kidney, and spleen for analysis of genome editing by Sanger sequencing, Surveyor assay, and next-generation sequencing (NGS, see on-target and off-target mutagenesis analyses below). The remainder of the liver was fixed in 10% buffered formalin for hematoxylin and eosin staining for histologic analysis. Plasma was collected for analysis of PCSK9 protein, total cholesterol and alanine transaminase (ALT) levels. Whole blood was obtained by retro-orbital bleed and spun at 10,000 rpm×2 minutes. Plasma PCSK9 protein and total cholesterol levels were measured using the Mouse Proprotein Convertase9/PCSK9 Quantikine ELISA Kit (R&D Systems) and the Infinity Cholesterol Reagent (Thermo Fisher Scientific), respectively, according to the manufacturer's instructions. Blood ALT levels were measured using the infinity ALT (GPT) Liquid Stable Reagent (Thermo Fisher Scientific) according to the manufacturer's instructions.

Genomic DNA from maternal organs of dams whose fetuses underwent prenatal Ad.BE3.Pcsk9 injection were assessed by Surveyor assays and NGS for on-target Pcsk9 editing 1 week after injection. Specifically, DNA from heart, lung, brain, kidney, ovary, and three distinct liver samples was assessed per mother.

Postnatal experiments: 5-week-old Balb/c or B6 mice were injected with $4\times10^9$ Ad.BE3.Pcsk9 particles via the retro-orbital vein. Liver was harvested at 5 days and 3 months post injection and genomic DNA was extracted for analysis of editing by Surveyor assay and NGS. In the subset of mice sacrificed at 3 months post injection, serum was isolated at 1 and 3 months post injection for analysis of anti-SpCas9 and anti-Ad antibody levels (see below).

FAH$^{-/-}$ Animal Studies

An initial in vivo screening study of the Ad.BE3.Hpd viral vector was performed in time-dated Balb/c fetuses. E16 Balb/c fetuses were injected with $5\times10^8$ Ad.BE3.Hpd particles and injected fetuses were sacrificed at 2 weeks of age. Livers were harvested for immunohistochemical analysis of HPD staining and genomic DNA was isolated from the liver, heart, brain, and lung for analysis of genome editing by Sanger sequencing, Surveyor assay, and next-generation sequencing. For experiments in Fah$^{-/-}$ mice, Fah$^{-/-}$ mice maintained on NTBC were time-dated and E16 fetuses were injected with $5\times10^8$ Ad.BE3.Hpd or $6\times10^8$ Ad.BE3.Null particles. An additional control group consisting of noninjected Fah$^{-/-}$ mice maintained on NTBC was also created. Injected pups were fostered on DOL1 with Balb/c dams that were not maintained on NTBC, thus removing NTBC from the breast milk received by injected pups. All mice were weighed every other day beginning on DOL7 and survival was monitored daily. Liver genomic DNA was assessed for genome editing by Surveyor assay and next-generation sequencing at DOL1, 1 month, and 3 months of age in recipients of Ad.BE3.Hpd and at ~DOL20 in recipients of Ad.BE3.Null (the time of clinical deterioration).

In addition, genomic DNA isolated at 1 month of age from the kidney, heart, lung, brain, and gonads of Ad.BE3.Hpd injected mice was assessed for genome editing by Surveyor assay. Prior to sacrifice at 1 month of age for Ad.BE3.Hpd injected Fah$^{-/-}$ mice and control Fah$^{-/-}$ mice on NTBC and just prior to death in the Ad.BE3.Null injected Fah$^{-/-}$ mice, liver function was assessed by serum biochemical analysis. Specifically, blood was collected by retroorbital bleed, maintained on ice, and immediately centrifuged at 14,000 rpm for 15 minutes at 4° C. Total bilirubin, aspartate transaminase (AST), and ALT were measured in fresh serum samples using the Vitros 350 Chemistry Analyzer.

Histology

At the time of tissue collection, mice were euthanized by decapitation (DOL1 mice) or $CO_2$ inhalation (all other mice). Organs were harvested and fixed in 10% buffered formalin. After serial dehydration in ascending concentrations of ethanol and xylene, organs were paraffin embedded and sectioned. Haematoxylin and eosin staining was performed for morphologic analysis. Immunohistochemistry was performed to determine GFP and TdTomato expression using the following antibodies for immunofluorescence images: GFP (goat, Abcam, ab5450, 1:100) and RFP (rabbit, Rockland, 600-401-379, 1:250). For GFP analysis by immunoperoxidase staining, slides were initially incubated with anti-GFP (rabbit, Thermo Fisher, A11122, 1:400) overnight at 4° C., washed and then incubated at room temperature for 30 minutes with the HRP polymer in the SuperPicture Polymer Detection Kit (Invitrogen, #878963) and subsequently developed with the DAB Peroxidase (HRP) Substrate Kit (Vector Labs, #SK-4100). For HPD analysis, HPD (rabbit, St. John's Laboratory, STJ28588, 1:1000) staining was performed on a Bond Max automated staining system (Leica Biosystems). The Bond Refine polymer staining kit (Leica Biosystems) was used. The standard protocol was followed with the exception that primary antibody incubation was extended to 1 hour at room temperature and the post primary step was excluded. Antigen retrieval was performed with Epitope Retrieval Solution 2 BOND (Leica Biosystems) for 20 minutes. Stained slides were digitally scanned at 20× magnification on an Aperio CS-O slide scanner (Leica Biosystems).

Liver HPD Quantification

Liver HPD expression was quantified by immunohistochemistry in prenatal recipients of Ad.BE3.Hpd and noninjected age-matched Balb/c control mice. Following HPD staining and digital slide scanning, whole slide image analysis using Aperio ImageScope (Leica) was used to count the total number of cells and the number of HPD-negative cells in each section as determined through thresholding and area measurement. Between 100,000 and 300,000 cells were counted for each mouse liver sample.

Image Analysis

For all histologic analyses except the quantification of HPD expression, images were taken on a Nikon Eclipse 80i fluorescence microscope. Fluorescent stereomicroscope (MZ16FA; Leica, Heerburg, Switzerland) was also used to visualize GFP expression following Ad.GFP and Ad.SpCas9.mTmG injection.

Anti-SpCas9 and Anti-Ad Serum Antibody Analysis

The levels of anti-SpCas9 antibodies and presence of anti-Ad antibodies in the serum of mice injected with Ad.BE3.Pcsk9 prenatally were compared to those injected with Ad.BE3.Pcsk9 postnatally and naïve, noninjected 1—and 3-month-old Balb/c controls. Serum was isolated at 1 and 3 months after injection and antibody levels were determined by ELISA as previously described. Briefly, 96 well Nunc MaxiSorp Plates (Thermo Fisher Scientific) were coated with SpCas9 protein (PNA Bio #CP01) at 0.5 µg/well or heat inactivated (30 minutes @ 90° C.) Ad viral particles ($5\times10^9$ particles/well) in 1× coating buffer diluted from Coating Solution Concentrate Kit (KPL) and placed at 4° C. overnight. Plates were washed with 1× Wash buffer and blocked with 1% BSA Blocking Solution (KPL) at room temperature for 1 hour. For the anti-SpCas9 studies, serum was diluted 1000-fold with 1% BSA Dilutent Solution (KPL) and added to wells for 1 hour at room temperature with shaking. The mouse monoclonal anti-SpCas9 antibody (Epigentek; clone 7A9, #A-9000-100) was serially diluted in 1% BSA Dilutent Solution and used as a standard to quantify anti-SpCas9 IgG1 levels. For the anti-Ad studies, serum was assessed at three different dilutions secondary to the lack of a standard mouse anti-Ad antibody for quantification. Thus, serum was diluted 1:100, 1:400, and 1:1600 with 1% BSA Dilutent Solution and added to wells for 1 hour at room temperature with shaking. After the 1-hour incubation, wells were washed and 100 µL of HRP-labeled mouse IgGk binding protein (Santa Cruz Biotechnology #sc-516102) was added to each well for an additional 1 hour at room temperature. Wells were subsequently washed ×4 and incubated with 100 µL of ABTS ELISA HRP Substrate (KPL). The SpectraMax M5 plate reader (Molecular Devices) with SoftMax Pro 6.3 software was used to measure Optical density at 410 nm.

On-Target and Off-Target Sequence Analysis

On-target editing of the Hpd and Pcsk9 genes was assessed by the Surveyor nuclease assay (CEL-I nuclease assay) as previously described. Briefly, genomic DNA from the indicated organs (liver, heart, lung, brain, spleen, kidney, or gonads) was isolated using the DNeasy Blood and Tissue Kit (QIAGEN) as per the manufacturer's instructions. PCR amplicons (see Table 3 for the primers used for Surveyor assays) were purified using the QIAquick PCR Purification Kit (QIAGEN), analyzed using the Surveyor Mutation Detection Kit (Integrated DNA Technologies) according to the manufacturer's instructions, and run on ethidium bromide-stained 2.5% agarose gels. PCR amplicons of on- and off-target predicted sites for Pcsk9 and Hpd were also subjected to next-generation DNA sequencing at the Massachusetts General Hospital CCIB DNA Core (CRISPR Sequencing Service; see the world wide web at dna-core.mgh.harvard.edu/new-cgibin/site/pages/crispr_se-quencing_main.jsp). Off-target sites were predicted using CRISPOR (on the web at crispor.tefor.net) and the top sites as ranked by the mitOfftargetScore were also subjected to next-generation DNA sequencing. Please refer to Tables 4 and 5 for the predicted Pcsk9 and Hpd off-target sites and the PCR primers used for on-target and off-target NGS analysis.

The number of paired-end reads typically exceeded 50,000 per target site per sample. On—and off-target indel mutagenesis rates and base editing rated were determined as previously described. We used custom scripts to map the processed sequencing reads, using the expected PCR amplicon sequence as the reference and discarding the reads that were not successfully mapped. To determine the base editing proportions, since the expected window for base editing spans from positions 4 to 8 in the protospacer, we used a window corresponding to positions 3 to 9 in the protospacer for each mapped read. In accordance with previously published analyses we discarded a read if the 4 bases proximal to the window (positions −1 to 2) and 4 bases distal to the window (positions 10 to 13) did not perfectly match the reference. In each of the remaining reads (denominator), we assessed each of the cytosine bases within the window in the reference for a change to another base; any read with at least one such change was tallied as a base-edited read (numerator).

TABLE 4

Off-target sites for Pcsk9 (SEQ ID NOS: 1-10) and
Hpd (SEQ ID NOS: 11-21)

| Protospacer and PAM | | Location | MIT off-target score |
|---|---|---|---|
| Pcsk9 | | | |
| CAGGTTCCATGGGATGCTCT | GGG | Exon:Pcsk9 | |
| CGCGGTCTATGGGATGCTCT | GGG | Intergenic:Snx8-Eif3b | 1.35 |
| CAGTTTCCATGGGGTGCTCT | TGG | Intron:Spata5 | 1.29 |
| TGTTTTCCATGGGATGCTCT | TGG | Intron:Ephb1 | 1.29 |
| CAAGCTCTAAGGGATGCTCT | GGG | Intron:Cnnm1 | 1.24 |
| CAGGATGGAGGGGATGCTCT | TGG | Exon:Cd5 | 0.82 |
| CCGCTTCCCGGGGATGCTCT | TGG | Exon:Mansc4 | 0.77 |
| CAGGTTTTATGGTATGCTCT | AGG | Intron:Shisa9 | 0.67 |
| GAAGTTTCATTGGATGCTCT | GGG | Exon:Gpr165 | 0.53 |
| CTGGTTCCATGGGAGGCTCA | AGG | Exon:Mtg1-Sprn | 0.40 |
| Hpd | | | |
| CATTCAACGTCACAACCACC | AGG | Exon:Hpd | |
| CATTCAACCTCACAACCACA | AGG | Intergenic:CbIn2_Gm5096 | 2.37 |
| CGGTTAAGGTCACAACCACC | TGG | Intergenic:8930078G14Rik=Fam155a | 1.35 |
| GGAGCAACGTCACAACCACC | AGG | Intron:Shank2 | 1.29 |
| TATTCAAAACCACAACCACC | TGG | Intron:Lrrc4c | 0.81 |
| ATTTCAAAGTCACAACCACA | GGG | Intergenic:5730420D 15Rik-Mrp142 | 0.7 |
| AATTCAAGGTCACAACCCCC | AGG | Intergenic:Gm2574-Gm24728 | 0.66 |
| CATAAAATGTCACAACCACA | TGG | Intron:Epha5 | 0.66 |
| CCTTCACCGTCACAAACACC | TGG | Exon:Lpin1 | 0.37 |
| CATACAACATCACAACCATC | AGG | Exon:Agb15 | 0.61 |
| CTTTCATCAGCACAACCACC | TGG | Exon:A4galt | 0.52 |

TABLE 5

Primer sequences for next generation sequencing for
Pcsk9 and Hpd on- and off-target sites. (SEQ ID NOS:
71-91 are shown in descending order)

| target | forward primer | reverse primer |
|---|---|---|
| Pcsk9 | | |
| Pcsk9 | AAGACTTTGTGAAGGCTGGGG | CTTCCTCTGTCTGGTGCCAT |
| Spatas | TCAGTCATGTAACCTCCCCCA | AGAACAGATTGCAAGCCATGAA |
| Ephb1 | CATGACCAGTGACCAGTGTTG | GGAGACCTTTCTGCCCAGTTG |
| Cd5 | AAGGAGAACTCCCTAGCACCA | GGAAGTGGGCAGCACTCAAA |
| Gpr165 | ATTGTTCAGCAACCTGGGGAA | TTCCCATGGAAATTCTAGGAGACC |
| Mansc4 | GCTGGCTAGCATGGTGCAT | TGGCCTTGTGCTGTGAAACTA |

TABLE 5-continued

Primer sequences for next generation sequencing for
Pcsk9 and Hpd on- and off-target sites. (SEQ ID NOS:
71-91 are shown in descending order)

| target | forward primer | reverse primer |
|---|---|---|
| Shisa9 | CCATCCCGTGACCAGATAGC | CCTTCCCACCACAGGGTTTT |
| Mtg1/Spm | AATGCTGACCGCCAAGAAGA | GGCGTCCTGGGATGGTTATT |
| Snx8-Elf3b | AAGGAAGCCTCCCCTTGTTTC | TCTGAACCTTCCTGATGCTCC |
| Cnnm1 | GGGGTGAGCTGTCCATGTG | CTGGGCTTGACACAGATTGG |
| Hpd | | |
| Hpd | CCTTCCTTTAACAGAGCCCACT | TGGGTAAGATTTCGCAGGCA |
| Cbln2 | ACCTCTTGTGTCTCTAAGGGC | AGTCTGATTCAAATAGGAGAATGTC |
| B9300 | CATTCCACACAACGCATTCC | ATGAACCAAACCCTCAGCCT |
| Shank2 | CATTTGGTGGTGTCAGCCTC | ACACCCAGCACAAGAGTTGA |
| Lrrc4c | GTTAGCCAAGGTTGTACCCCA | GCTCAGGGTCTTTCGCCTAA |
| 5730 | TTGGCCAGCTAGAAAGCAGA | CACATTCTCGACGAAACCGC |
| Gm2574 | AGTTCCGGATGTCTGAAGGGA | CTTATGCCCCTGCATTCCTGAT |
| Epha5 | CATTCATAAGGTACAATCAACGACA | GGGTCCATGCTACAGCAGTT |
| Lpin1 | TCGTTGAAACGGAGTGCTGA | GGCTGCCGGATGACAATGAT |
| Agb15 | AAACAGTGCTAAACAGTGACGC | CCTGGAAGTCAAAGTGGGCT |
| A4galt | CTCAGAAGAGAGATGCCGAGG | AGCTGGCCTTTCCTAGAGTC |

Quantitative Reverse Transcriptase-Polymerase Chain Reaction (qRT-PCR)

Organ samples stored in RNAlater TissueProtect Tubes (#76154, QIAGEN) were used for RNA preparation with the RNeasy Mini Kit (#74104, QIAGEN), according to the manufacturers' instructions. Reverse transcription was performed after removal of contaminating genomic DNA, using SuperScript™ IV VILO™ Master Mix with ezDNase™ Enzyme (#11766050, Thermo Fisher Scientific).

Gene expression was measured using the following TaqMan Gene Expression Assay along with TaqMan Gene Expression Master Mix (Thermo Fisher Scientific): Mouse GAPD (GAPDH) Endogenous Control (VIC/MGB probe, primer limited) (#4352339E), for Gapdh as the reference gene. For the BE3 gene, the primers F: 5'—AAGCGCATA-CAACAAGCACA-3'(SEQ ID NO: 92) and R: 5'-GAATCAGTGTCGCGTCTAGC-3'(SEQ ID NO: 93) were used with SYBR Green (Thermo Fisher Scientific). Each 10 µL qRT-PCR reaction contained 3 µL cDNA (diluted 1:5 with water) and was performed in technical triplicate. Reactions were carried out on the QuantStudio 7 Flex System (Thermo Fisher Scientific). Relative expression levels were quantified by the $2^{-\Delta\Delta Ct}$ method.

Statistics

A two-tailed Student's t test was used for experiments involving the comparison of two groups in which data was normally distributed as determined by the D'Agostino and Pearson omnibus test of normality. The Mann-Whitney U test was used for experiments involving the comparison of two groups in which data was not normally distributed. The Kruskal-Wallis rank sum test for multiple independent samples using the Dunn method with adjustment of the P-value according to the false discovery rate procedure of Benjamini-Hochberg was used for experiments involving the comparison of more than 2 experimental groups. Survival statistics were assessed with the Logrank test. Unless otherwise indicated, data are represented as the mean±SEM or the mean with individual values.

RESULTS

Establishing in Utero Genome Editing

Figures 6G, 6H, 6I, 6J, 6K, 6L, 6M, 6N, 6O, 6P, 6Q, 6R, 6S, 6T, 6U, 6V, 6W, 6X, 6Y, 6Z:
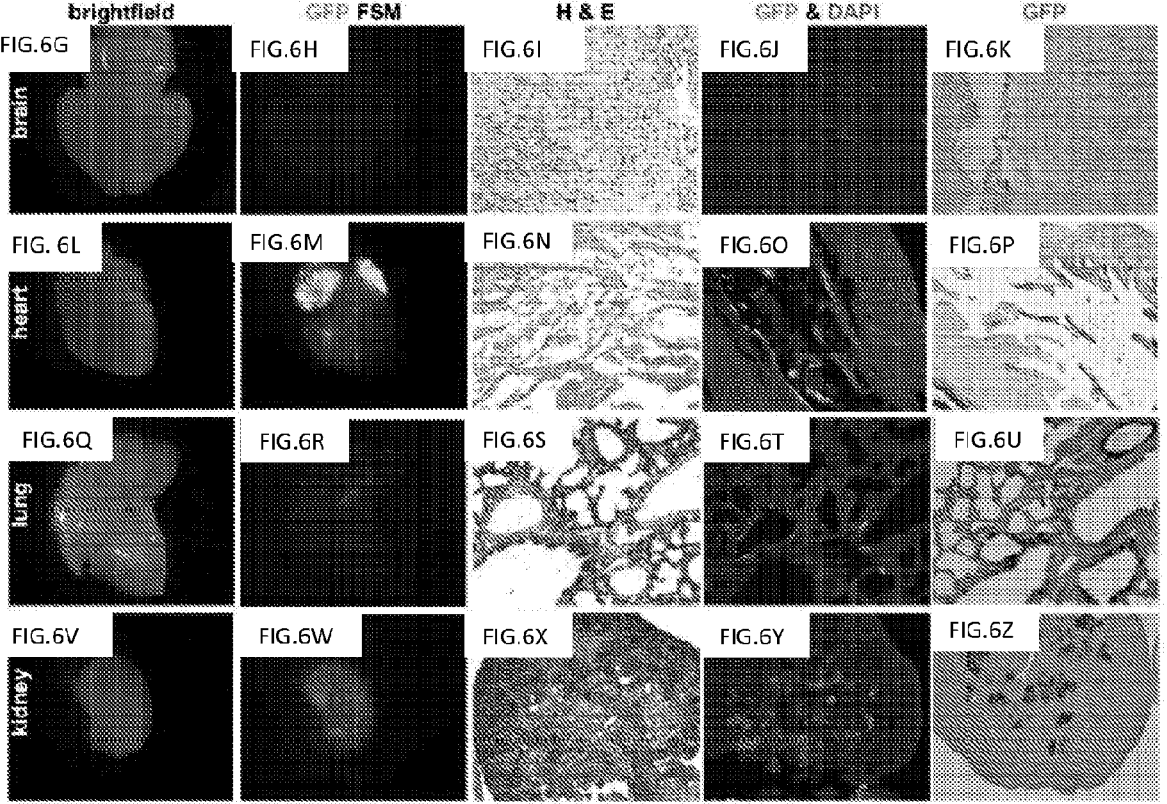

Viral vectors have been used to deliver CRISPR-Cas9 editing technology in vivo. The large sizes of *Streptococcus pyogenes* Cas9 (SpCas9; ~4.2 kb) and especially of BE3 (~5.1 kb) complicates their delivery via adeno-associated viral (AAV) vectors (packaging capacity ~4.7 kb). Thus, we utilized adenoviral (Ad) vectors to deliver SpCas9 or BE3 for in utero genome editing/base editing experiments. We initially evaluated our ability to target different organs following in utero delivery of a vector carrying the GFP transgene (Ad.GFP). Gestational day (E) 16 fetuses were injected with Ad.GFP via the vitelline vein, which provides first-pass effect to the liver (FIG. 1A). Robust transduction of hepatocytes was noted at day of life (DOL) 1 (FIGS. 6A-6Z). Hepatocytes expressing GFP were present, although at decreasing levels, at 3 months of age (FIGS. 6A-6Z). No significant inflammation in the liver was noted, although evidence of extramedullary hematopoiesis was evident in the liver on DOL1 consistent with the liver being a hematopoietic organ at this age. Analysis of other organs at DOL1 demonstrated significant GFP florescence in the heart, lung, and kidney, while minimal GFP fluorescence was appreciated in the brain (FIGS. 6G-6Z).

Figure 5A:
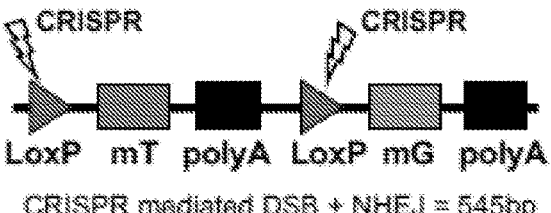

The inventors next sought to confirm our ability to perform prenatal CRISPR-Cas9-mediated genome editing in an easily tractable model. Gt(ROSA)26Sortm4(ACTB-td-Tomato,-EGFP)Luo mice (referred to as R26$^{mTmG/+}$) have a two-color fluorescent Cre-reporter allele (mT-tdTomato: red; mG-EGFP: green) in which the mT cassette is flanked by loxP sites (FIG. 5A). These mice constitutively express red fluorescence in all cells, including hepatocytes, until deletion of the mT cassette, which allows expression of EGFP. Ad vectors containing SpCas9 and a guide RNA (gRNA) targeting the loxP sites were injected via the vitelline vein into E16 R26$^{mTmG/+}$ fetuses, and the liver, heart, lung and brain were assessed for genome editing on DOL1. Specifically, double strand DNA breaks (DSBs) followed by NHEJ-mediated removal of the mT cassette would result in EGFP expression and a detectable PCR band.

Mice injected with Ad.Cre served as positive controls. Using this system, we demonstrated successful IUGE in the heart, brain, and liver, with the most robust editing seen in the liver and heart.

In Utero Genomic Editing of the PCSK9 Gene

Individuals with nonsense variants in the PCSK9 gene are known to have reduced cholesterol levels and risk of coronary heart disease (CHD). Previous studies have demonstrated the feasibility of CRISPR-Cas9 mediated NHEJ to disrupt PCSK9 orthologs in hepatocytes in vivo postnatally. Base editing with the base editor BE3 is a more novel form of CRISPR mediated genome editing in which a catalytically impaired SpCas9 unable to make double strand breaks (DSBs) is fused to the cytosine deaminase domain of the RNA editing enzyme APOBEC1. BE3 is able to make site specific C→T or G→A changes in the genome and because of its inability to make DSBs do so in a safer fashion than CRISPR mediated NHEJ. In the current study, the inventors evaluate prenatal in vivo base editing of Pcsk9 in a proof of concept model of in utero genome editing (IUGE) of a therapeutic gene. The rationale for IUGE is that many congenital genetic abnormalities result in significant morbidity shortly after birth and the potential benefits of targeting a therapeutic gene, including those involved in CHD, may be enhanced if the gene is corrected for the individual's lifetime. Furthermore, the small fetal size, accessible progenitor cells, and fetal immunologic immaturity provide the potential for edited cells to persist for a lifetime.

Methods

BE3 and gRNA targeting a W159X mutation in the Pcsk9 gene were delivered in an adenoviral vector (Ad.BE3.Pcsk9) to gestational day 16 Balb/c fetuses via vitelline vein injection. Adenovirus carrying GFP or an untargeted BE3 were injected as negative controls. DNA from liver, heart, brain, spleen, and lung was harvested at postnatal day 1, 14, 30, and 90 and assessed by Surveyor and deep sequencing for Pcsk9 and off-target editing. Serum was assessed for PCSK9, cholesterol and ALT levels. Statistics were performed with a Mann-Whitney test.

In Utero Pcsk9 Base Editing

Figure 5B:
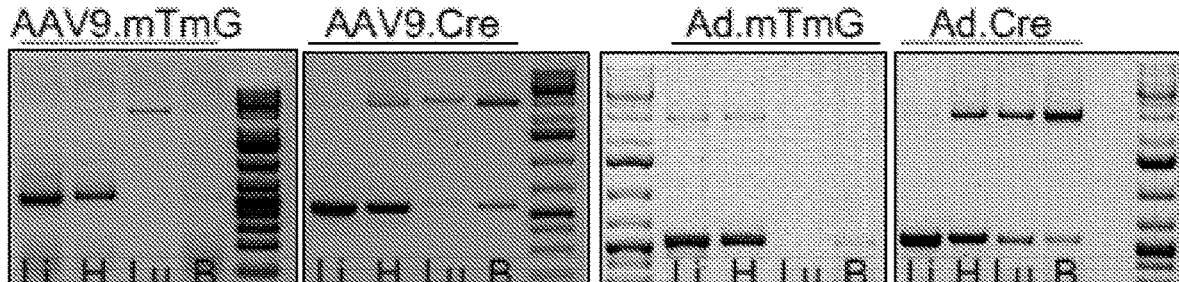
Figure 5C:
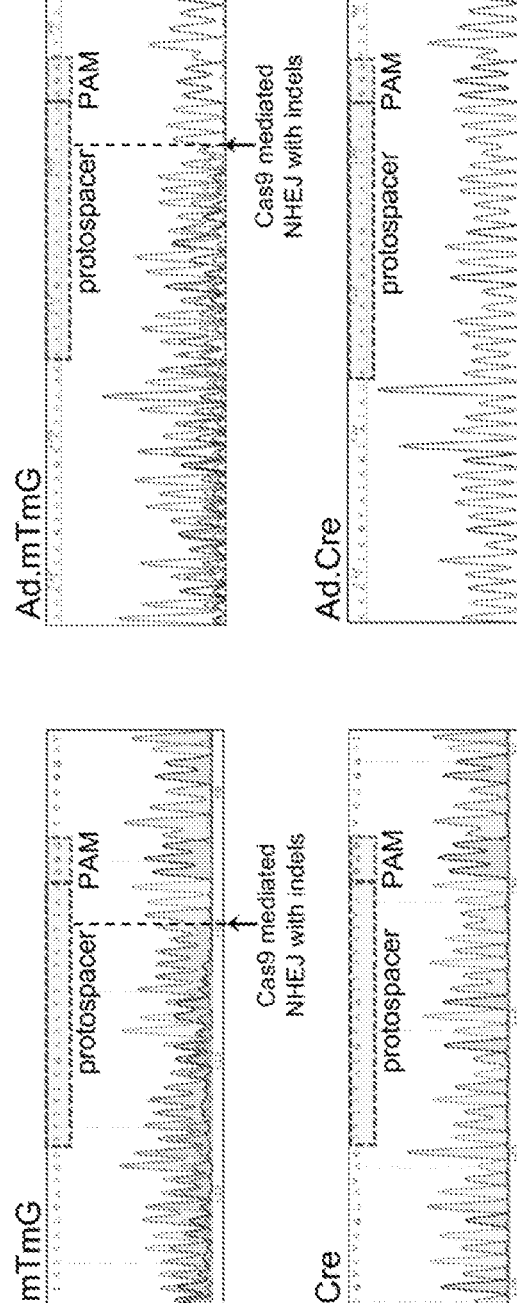

In the present example, we employed BE3 for in utero base editing of hepatocytes. BE3 can make site-specific CT or GA changes in coding sequences without double-strand DNA breaks, making it potentially safer than standard CRISPR-Cas9 genome editing. The large size of SpCas9-based BE3 (~5.1 kb) preempts its delivery via AAV (capacity ~4.7 kb). We thus turned to adenoviral (Ad) vectors for the subsequent series of proof-of-concept experiments. We injected E16 wild-type fetuses with an Ad vector expressing GFP (Ad.GFP) via the vitelline vein and observed robust hepatocyte transduction at DOL1, with decreased levels at 3 months (FIG. 1A, FIG. 7). We then injected Ad vectors encoding either SpCas9 and a loxP-targeting gRNA (Ad.SpCas9.mTmG) or Cre recombinase (Ad.Cre) into E16 R26$^{mTmG/+}$ fetuses and observed editing in various organs on DOL1, with the most robust editing seen in liver and heart (FIG. 5).

Figure 1D:
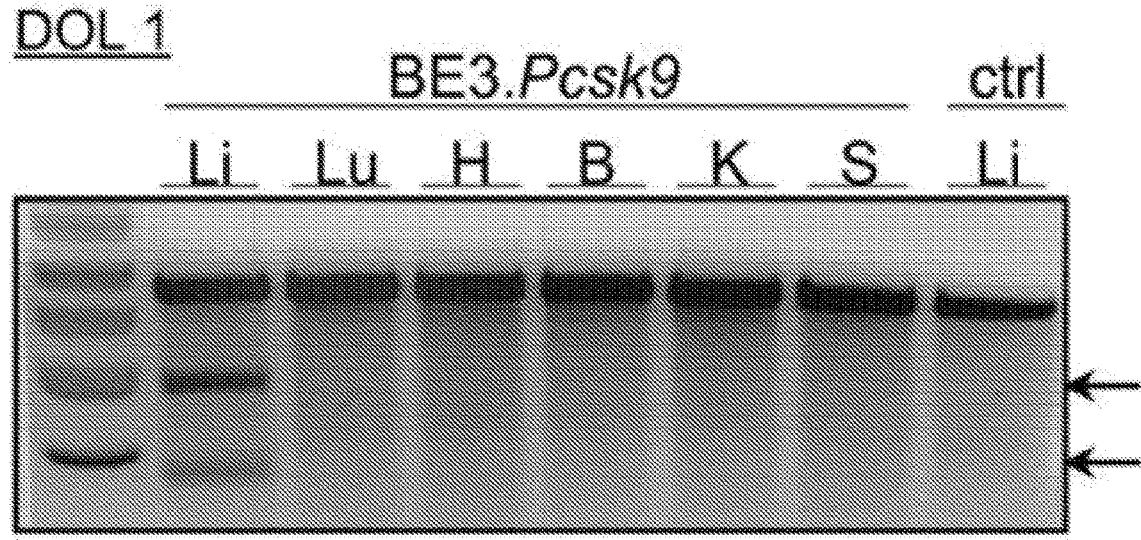

Loss-of-function mutations in PCSK9 reduce cholesterol levels and coronary heart disease risk without serious adverse consequences. Previous studies demonstrated CRISPR-Cas9-mediated nonhomologous end-joining (NHEJ) or base editing to disrupt PCSK9 orthologs in mouse and human hepatocytes in vivo postnatally. We evaluated if in utero base editing of murine Pcsk9 reduces postnatal plasma PCSK9 and cholesterol levels. We used an Ad vector containing BE3 and a gRNA targeting Pcsk9 codon W159 (Ad.BE3.Pcsk9) that in a previous adult mouse study resulted in conversion to stop codons. Following injection of E16 Balb/c fetuses, Ad.BE3.Pcsk9 resulted in base editing in liver apparent on DOL1 without evidence of editing in other organs (FIG. 1B-1D). Analysis of DNA from organs of mothers of injected fetuses showed no significant Pcsk9 editing [FIG. 1E; next-generation sequencing (NGS) on-target Pcsk9 base-edited alleles: 0.06-0.14%, N=2 mothers; negative control: 0.06-0.3%].

Figure 1G:
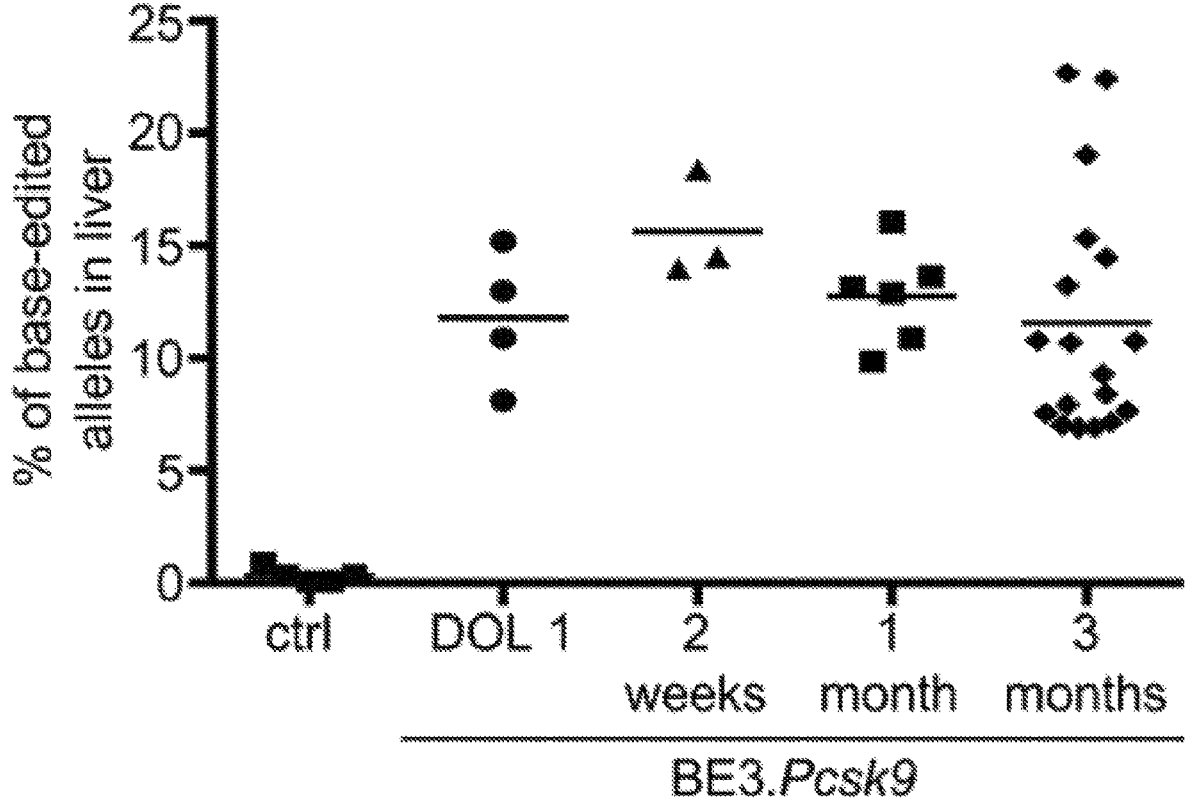

Assessed by Surveyor assays and NGS of the target site, the proportion of Pcsk9 base-edited alleles in livers of in utero Ad.BE3.Pcsk9-injected mice was stable at 10-15% between DOL1 and 3 months (FIGS. 1F, 1G). The indel rate was low (~2%) (FIG. 1H), contrasting with >40% indel rates seen in previous postnatal studies using NHEJ to disrupt Pcsk9. NGS analysis of 9 top predicted off-target sites in liver DNA from two 2-week-old Ad.BE3.Pcsk9-injected mice showed no evidence of editing (FIG. 1I).

Figure 2N:
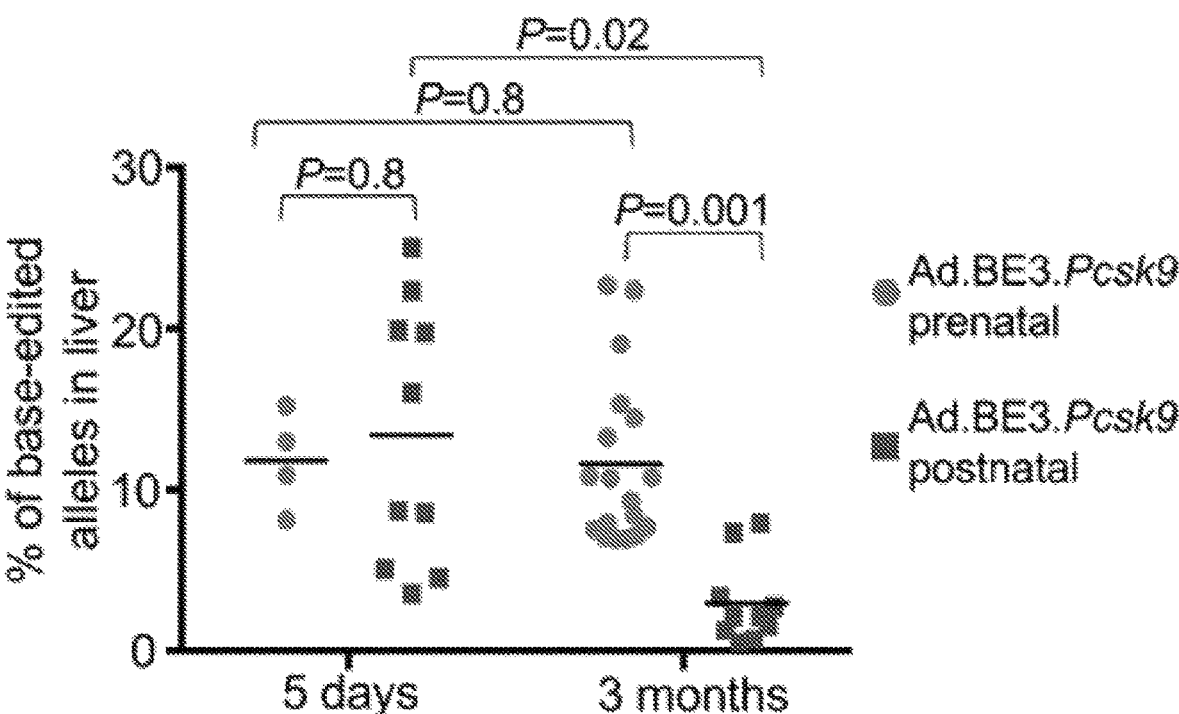
(FIG. 2N) Ad.BE3.Pcsk9 was injected into E16 Balb/c fetuses and 5-week-old Balb/c mice. Percentage base-edited csk9 on-target alleles, NGS, liver genomic DNA at 5 days and 3 months post-injection (prenatal 5 days-N=4, 3 months-N=18; postnatal 5 days-N=10, 3 months-N=10).
Figure 2O:
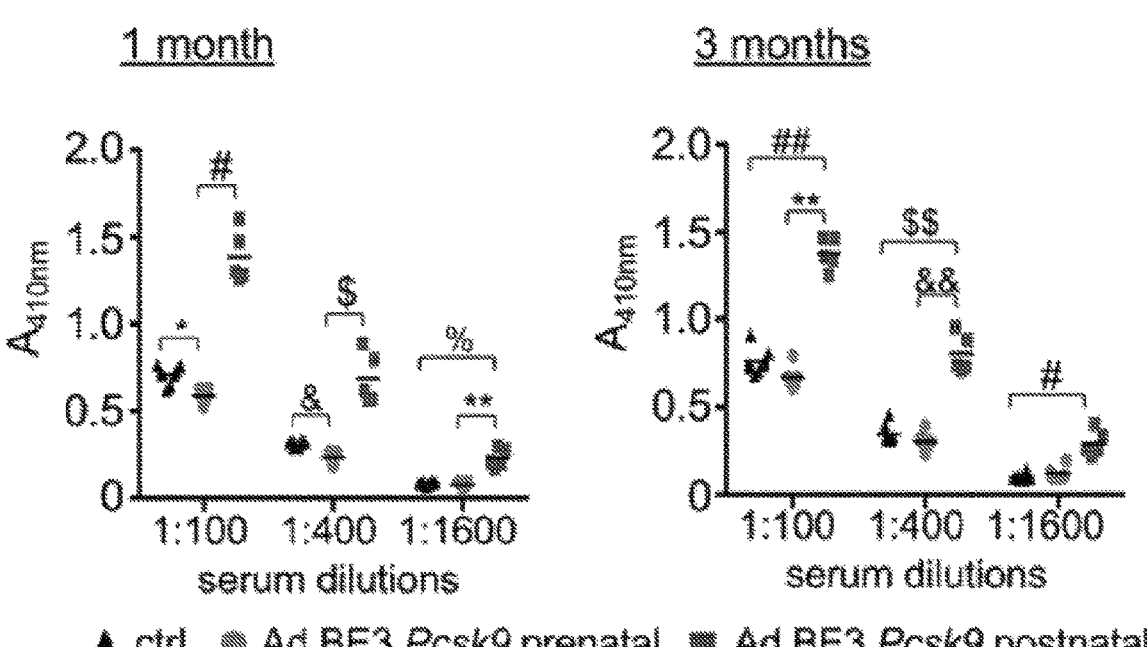
Figure 2P:
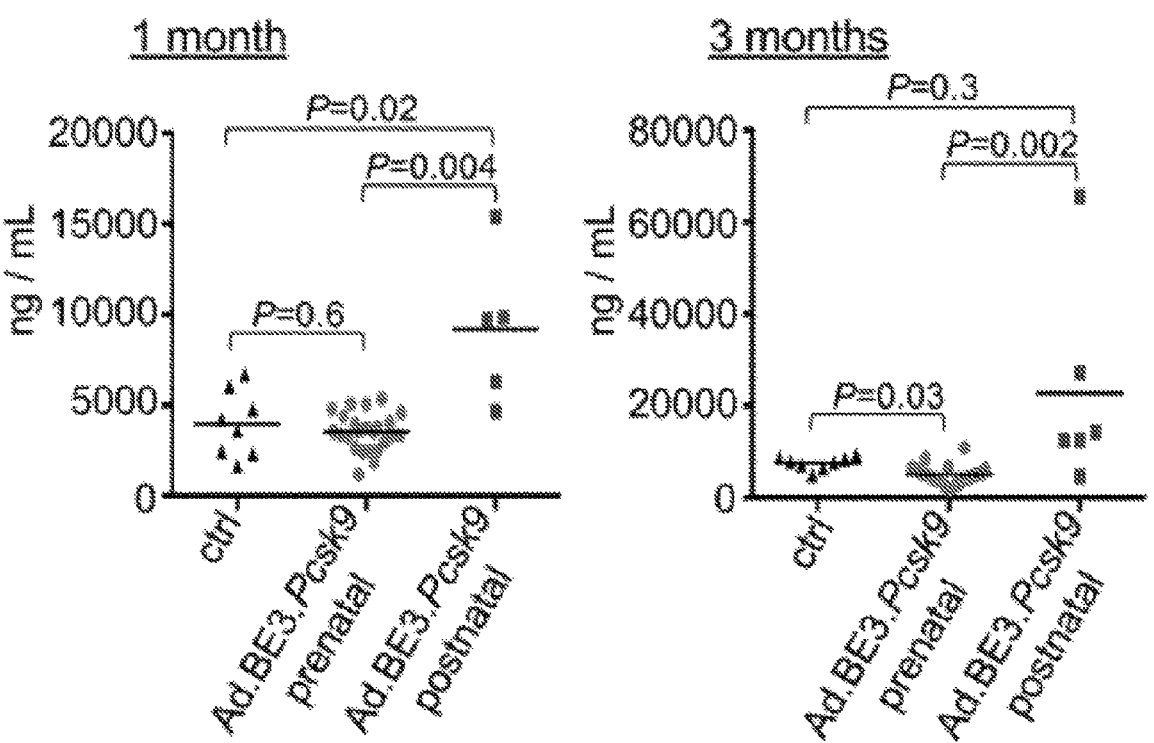

Compared with a control Ad vector, in utero Ad.BE3.Pcsk9 resulted in decreased postnatal levels of PCSK9 protein and total cholesterol at 1 and 3 months, with no differences in alanine aminotransferase levels and grossly normal liver histology (FIGS. 2A-2L). Mice treated postnatally at 5 weeks of age with Ad.BE3.Pcsk9 had substantial editing at early post-injection timepoints (5 days, 1 month) but attenuated editing at later timepoints (2 and 3 months) (FIGS. 2M, 2N). In contrast, prenatal Ad.BE3.Pcsk9 recipients had stable editing over time, with significantly higher editing rates than postnatal recipients at 3 months despite having similar rates at 5 days (FIG. 2N). Previous studies of gene therapy documented immune responses to both the Ad vector and the transgene product following postnatal delivery that were diminished with prenatal delivery 15,16. We assessed if there was a different immune response to the Ad vector and SpCas9-based BE3 transgene product following prenatal versus postnatal Ad.BE3.Pcsk9 delivery, which might explain the difference in editing stability. Serum anti-Ad and anti-SpCas9 antibodies were higher in postnatal compared to prenatal recipients and naïve controls at 1 and 3 months post-injection, and equal or lower in prenatal recipients compared to naïve controls (FIGS. 2O and 2P). These results demonstrate the feasibility of in utero base editing of the therapeutic gene Pcsk9. They highlight the ability to achieve long-term edited cells with an associated desired phenotypic change. This study provides proof of principle for prenatal editing that could ameliorate genetic conditions that have significant neonatal morbidity/mortality.

Figure 7A:
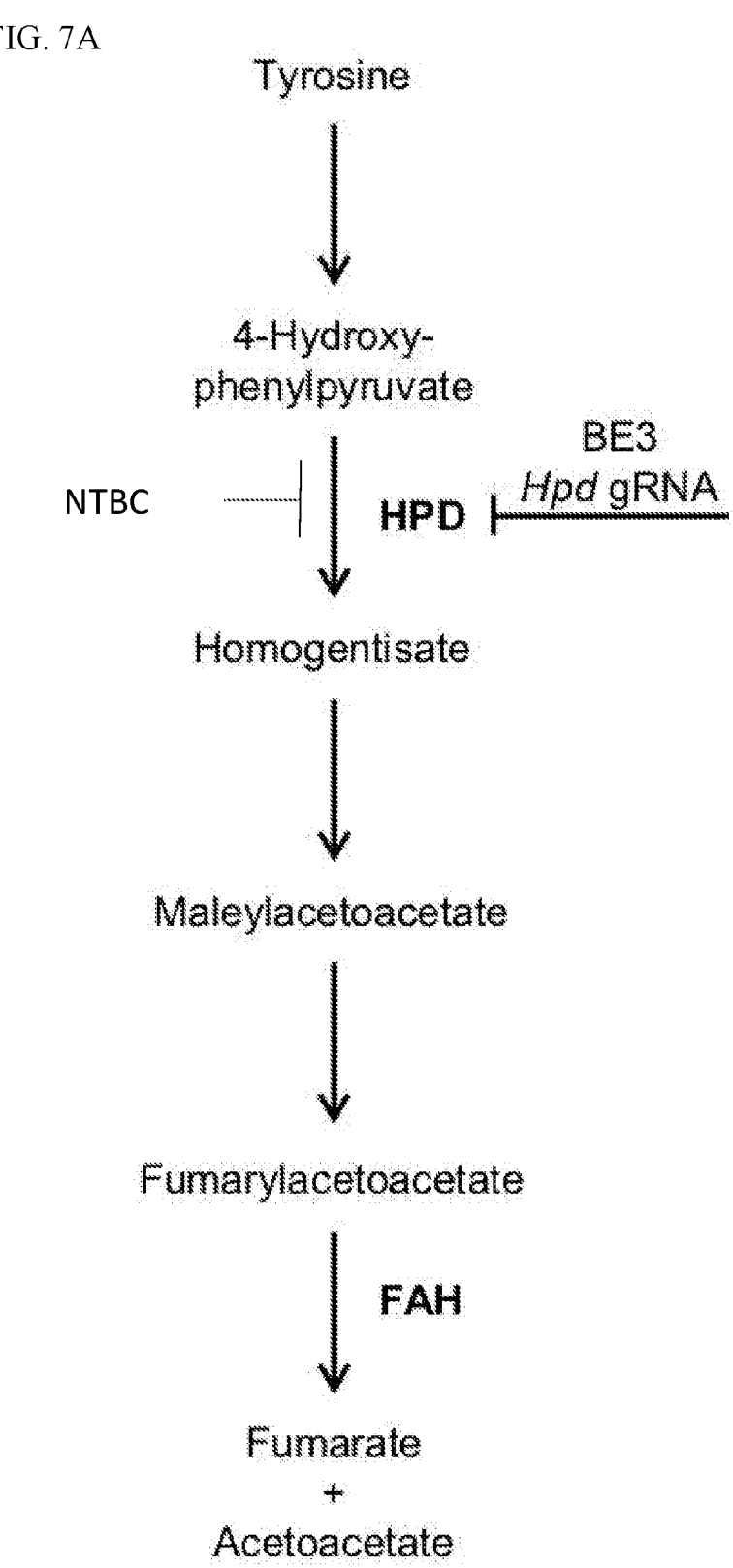

Having demonstrated in utero base editing of Pcsk9, we next sought to target a gene for which the in utero approach would be more relevant. HT1 results from a mutated Fah gene blocking the tyrosine catabolic pathway (FIG. 7A). Inhibiting the upstream HPD enzyme in this pathway with the drug NTBC prevents the accumulation of toxic metabolites and rescues the lethal liver failure (FIG. 7). We sought to introduce a nonsense mutation in the Hpd gene in utero to permanently knock out gene function. We screened 8 gRNAs in vitro and observed the most editing at codon Q352 (FIG. 7C). In utero base editing of Hpd in E16 wild-type fetuses with an Ad vector encoding BE3 and the Q352 gRNA (Ad.BE3.Hpd) resulted in a mean editing rate of ~15% in liver at 2 weeks of age; analysis of other organs showed no editing.

Figure 3B:
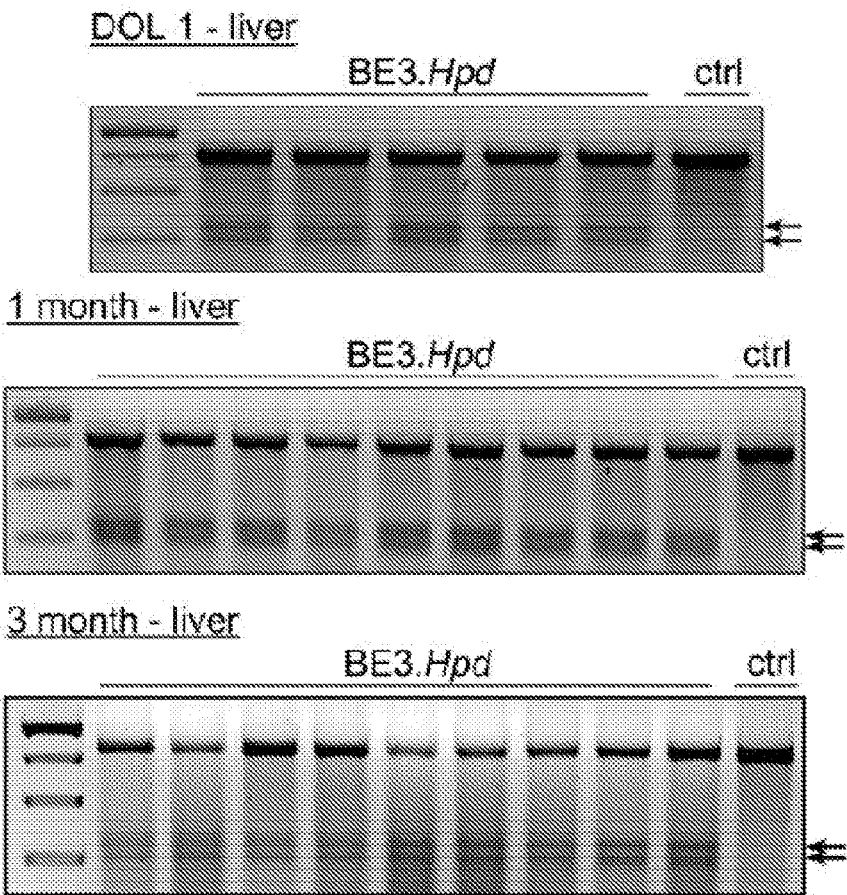

Fah$^{-/-}$ mice, a model of HT1, experience neonatal lethality and can be rescued with NTBC delivered via the mother's breast milk. Previous studies have demonstrated amelioration of HT1 in this model with postnatal gene editing via homology-direct repair or NHEJ18-20. We mated Fah$^{-/-}$ adult mice on NTBC and administered Ad.BE3.Hpd to E16 fetuses, and on DOL1 we placed the recipients with foster mothers not on NTBC (FIG. 3A). Base editing in liver was substantially higher in recipient mice analyzed at 1 month and 3 months than at DOL1 (37% and 40% versus 14%) (FIGS. 3B, 3C), likely due to the survival advantage and subsequent expansion of edited cells. In addition to the desired CT nonsense mutation at the target site, there were much lower rates of alternative missense mutations and indels (FIG. 3D). We observed no evidence of editing in other organs including gonads at 1 month (FIG. 3E); sperm from two 3-month-old recipient mice with liver Hpd editing rates of 46-57% demonstrated no significant editing by Surveyor assays (FIG. 3E) or NGS (0.2-0.8%; controls: 0.03-0.6%). We observed BE3 expression in heart (FIG. 6) and speculate the Hpd locus was inaccessible to BE3 in cardiomyocytes, where Hpd is not expressed. NGS analysis of 10 top-predicted off-target sites in liver DNA from 1-month-old recipient mice showed no evidence of editing (FIG. 3F).

Figures 4A, 4B, 4C, 4D:
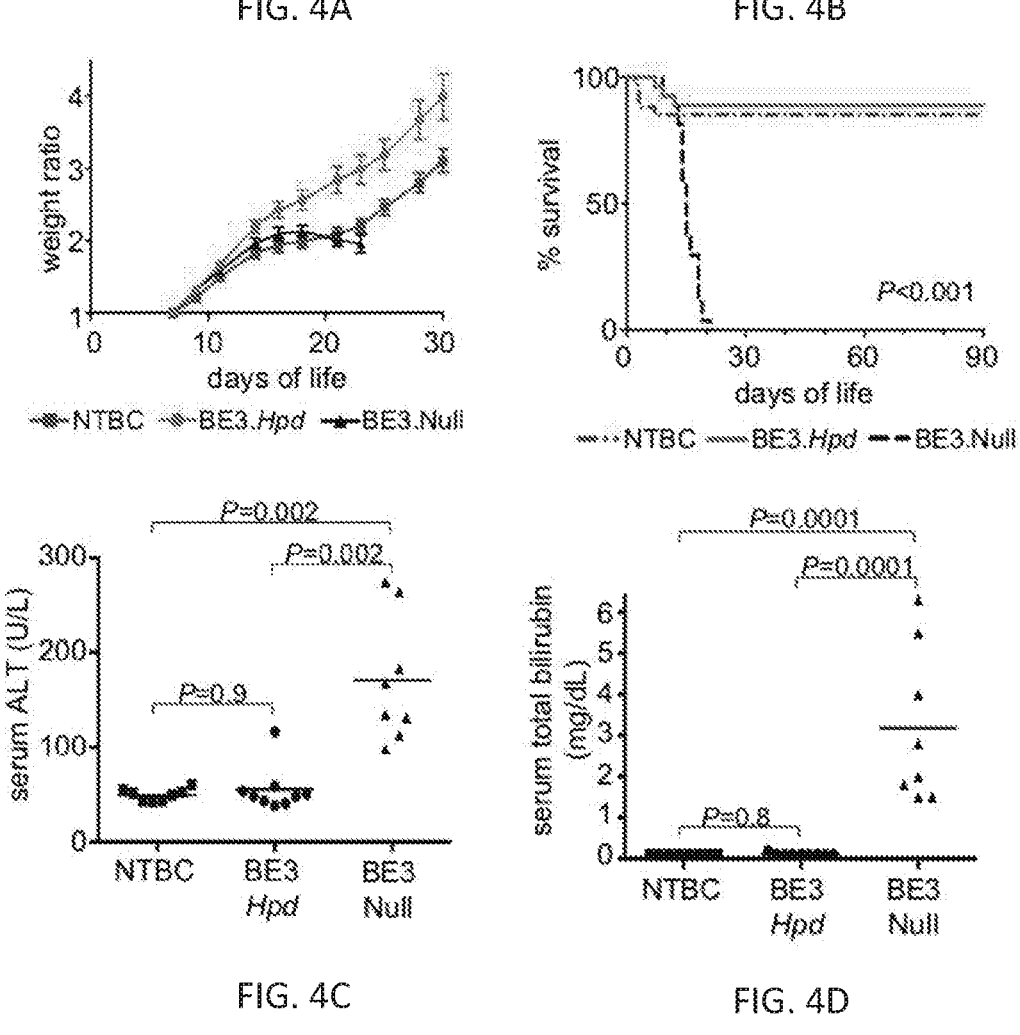
FIGS. 4A-4G: In utero Hpd base editing improves liver function and rescues the lethal phenotype of Fah−/− mice.
Figures 4E, 4F, 4G:
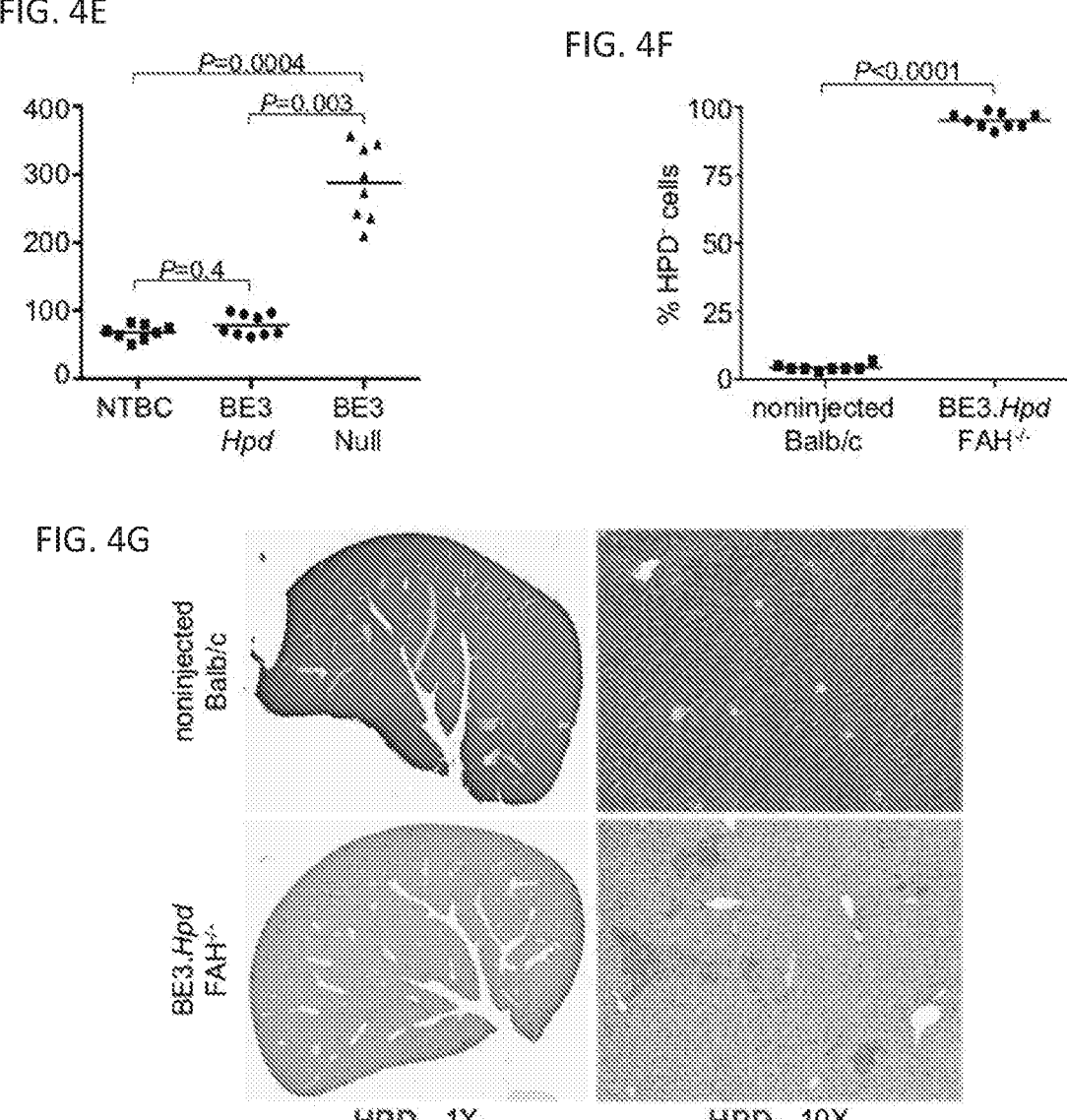
Figure 8A:
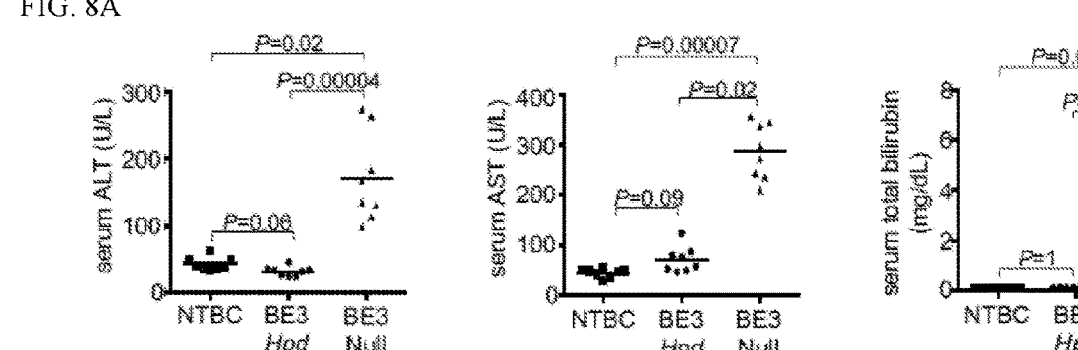
FIGS. 8A-8C: Liver function and histology of FAH−/− mice following prenatal Ad.BE3.Hpd injection.
Figure 8B:
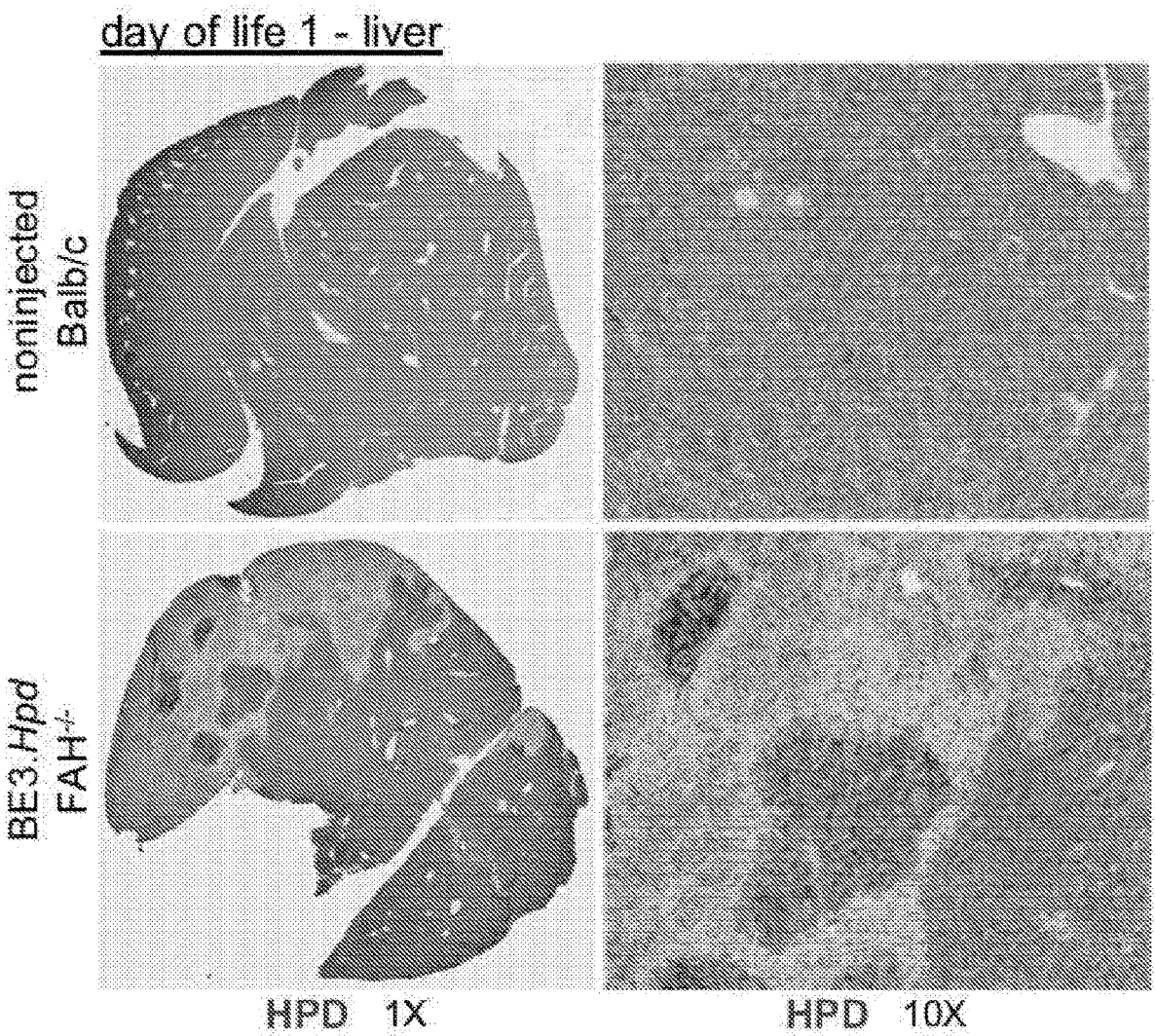
Figure 8C:
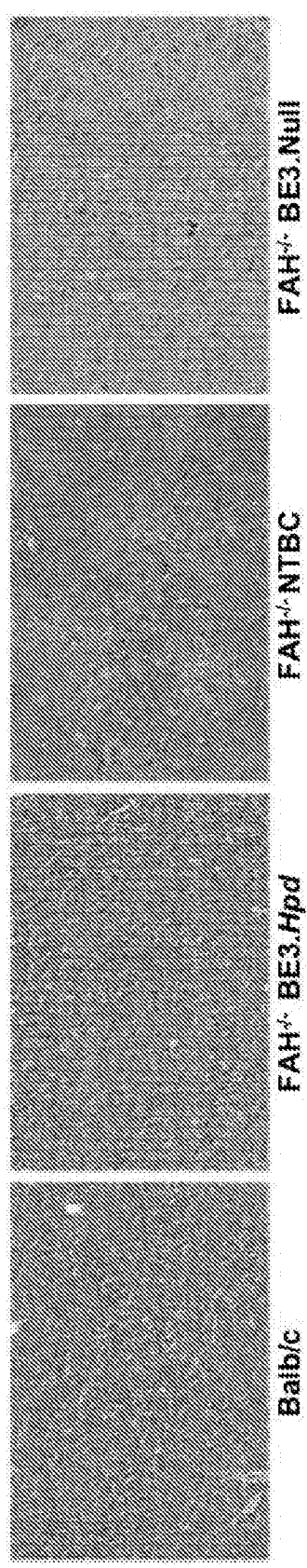

In utero Ad.BE3.Hpd treatment rescued the lethal phenotype in Fah$^{-/-}$ mice following withdrawal of NTBC at birth. In contrast to recipients of the control Ad.BE3.Null vector, all of which lost weight prior to death and did not survive beyond 21 days, Ad.BE3.Hpd recipients demonstrated appropriate weight gain with 89% survival at 3 months (FIGS. 4A, 4B). Notably, weights of Ad.BE3.Hpd-injected mice exceeded those of non-injected Fah$^{-/-}$ mice maintained on NTBC. Additionally, liver function of Ad.BE3.Hpd-injected Fah$^{-/-}$ mice and non-injected, NTBC-treated Fah$^{-/-}$ mice was similar at 1 and 3 months and significantly improved compared to Ad.BE3.Null recipients prior to their death (FIGS. 4C-4E, FIG. 8). Improved survival and liver function in Ad.BE3.Hpd recipients correlated with a substantial reduction in HPD+ cells on immunohistochemistry at DOL1 (FIG. 8) and one month (FIGS. 4F, 4G). Liver histology in 1-month-old Ad.BE3.Hpd recipients revealed no significant inflammation or abnormality; in Ad.BE3.Null-injected mice, variability in nuclear size and apoptotic hepatocytes consistent with liver injury were evident (FIG. 8).

In summary, we established the feasibility of in utero CRISPR-mediated therapeutic editing of metabolic genes. We used Ad vectors for these studies, recognizing that alternative methods such as lipid nanoparticles can also be exploited and optimized to facilitate translation to the clinic to occur. The present work highlights the advantages provided by in utero base editing to target a gene—either by disruption, as done here with Hpd, or potentially by directly correcting disease-causing mutations—for the purpose of treating a congenital genetic disorder that can be diagnosed early in pregnancy. Although HT1 served as a proof-of-concept disease model to investigate in utero base editing, this approach holds greater potential for diseases that have no effective treatment for the majority of patients and result in profound morbidity and mortality shortly after birth.

In Utero Hpd Base Editing to Cure Tyrosinemia

Figure 7D:
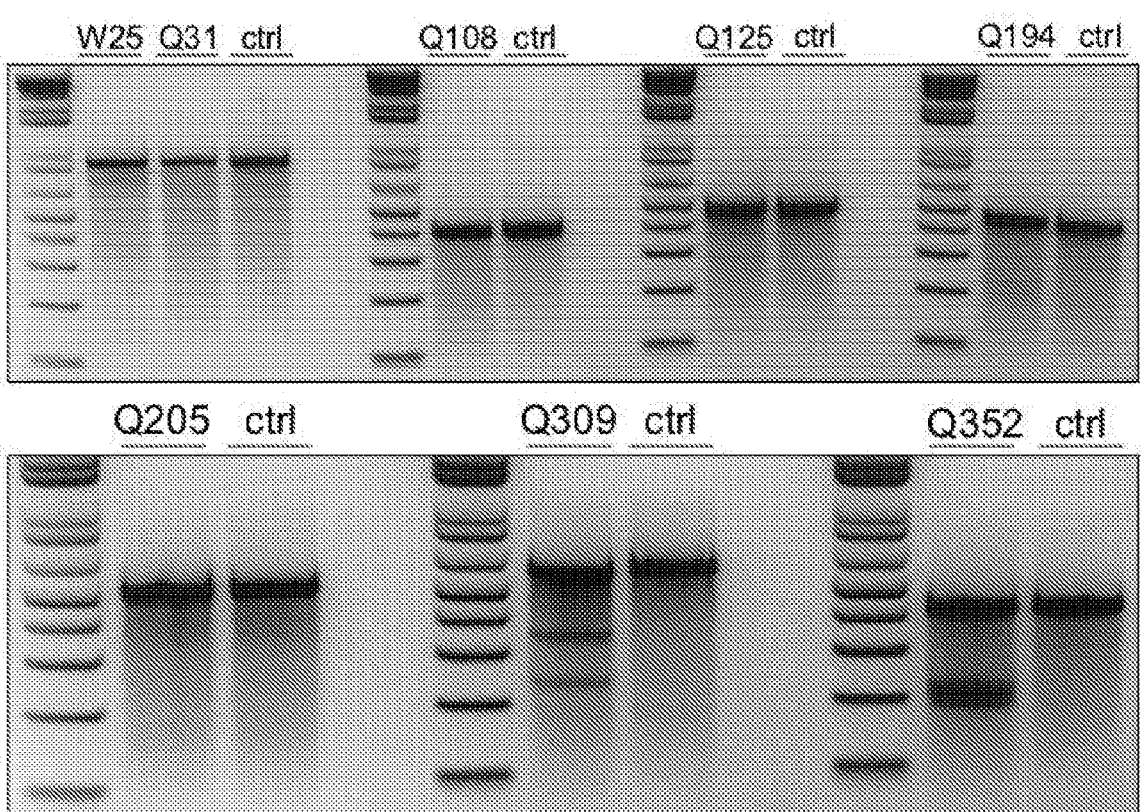
Figures 7E, 7F:
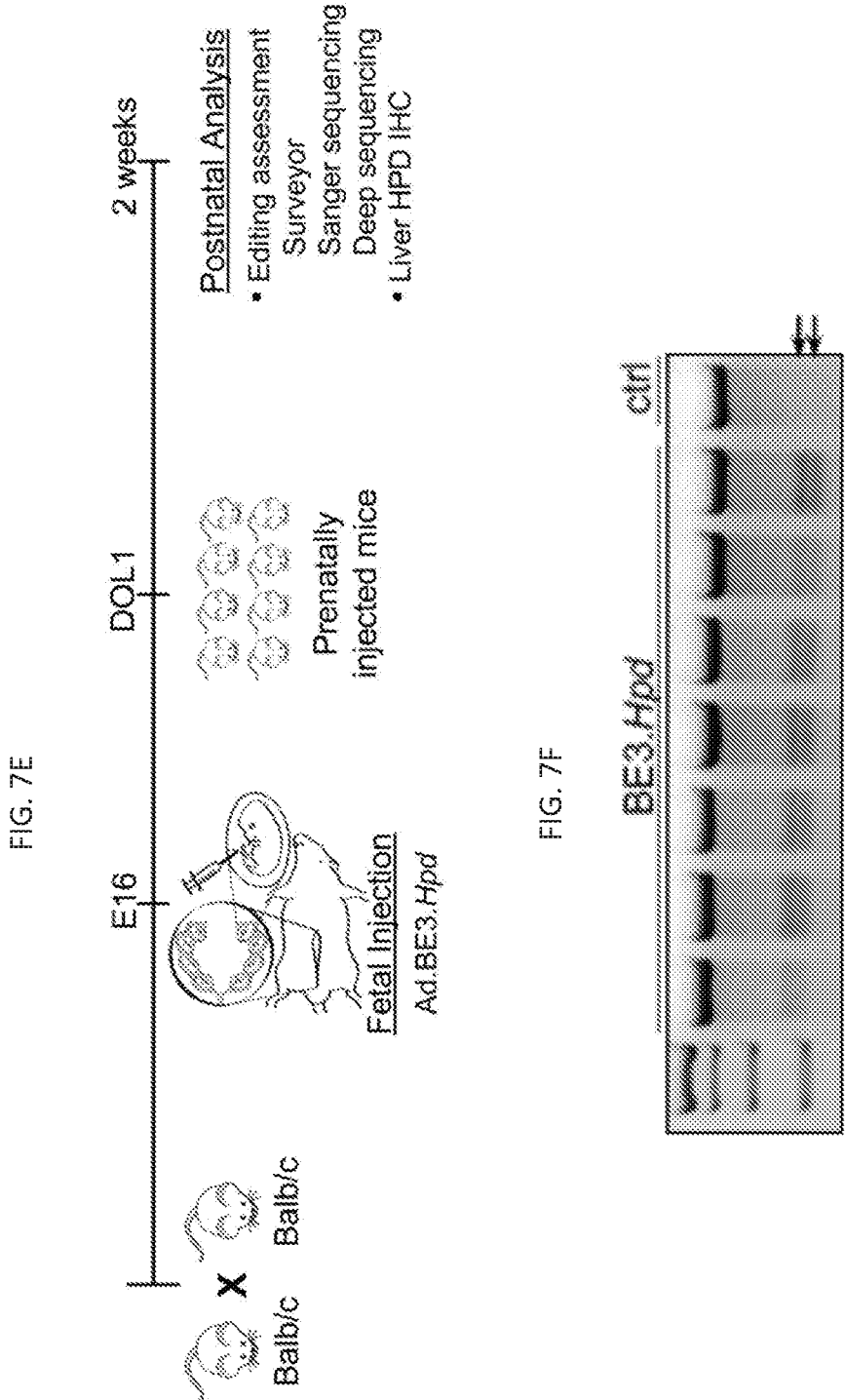
Figure 7G:
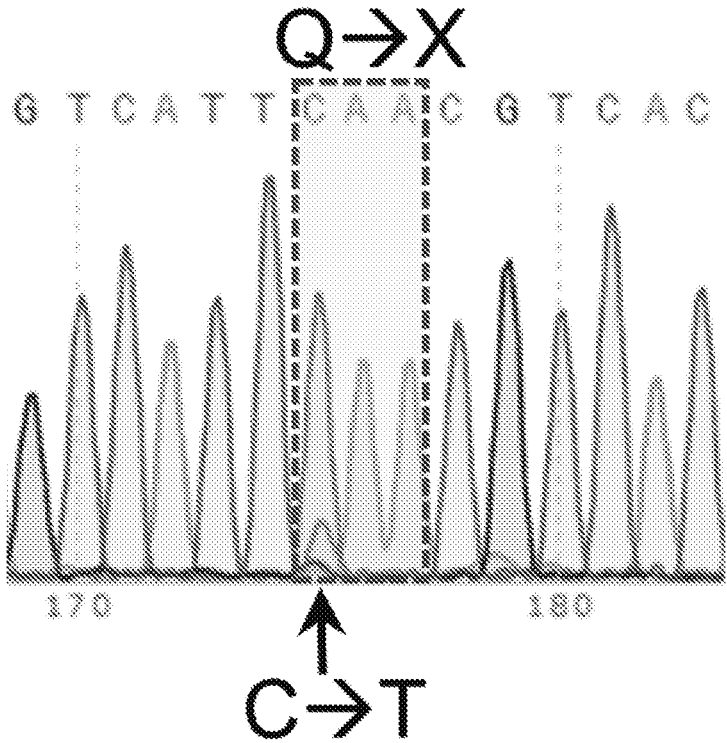
Figure 7H:
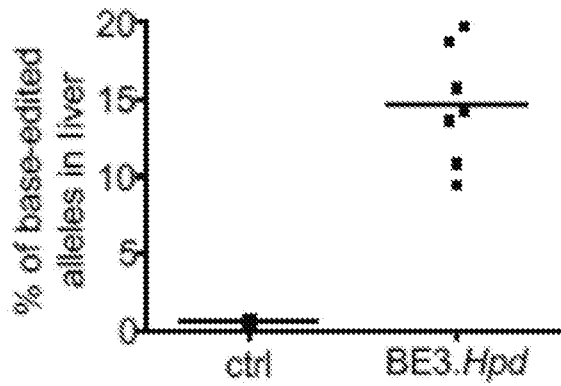
Figures 7I, 7J:
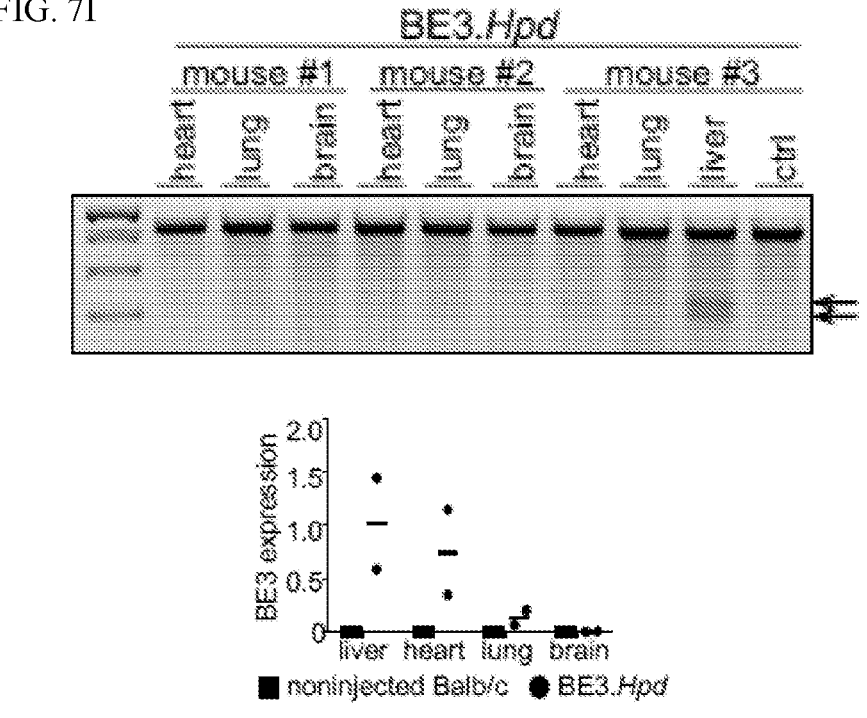
Figure 7K:
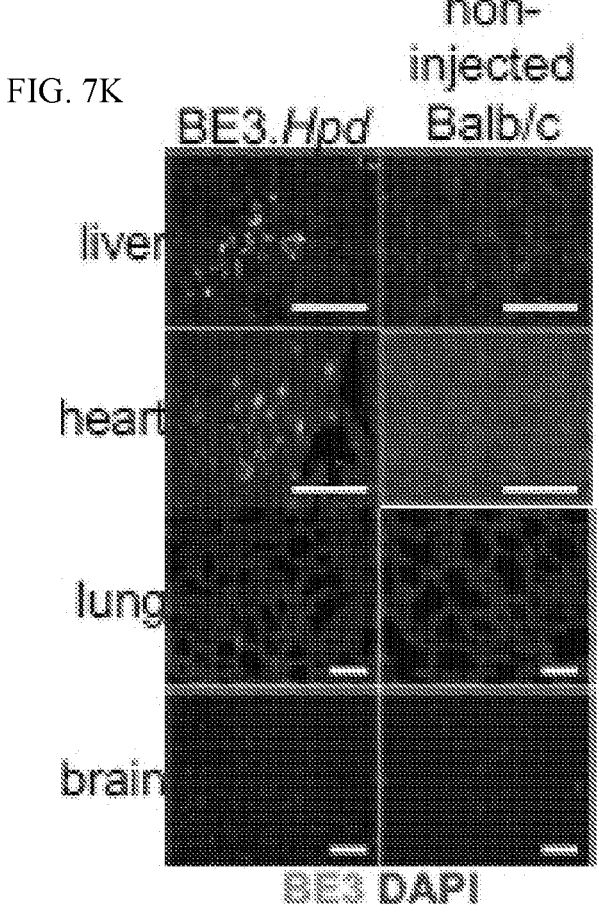
Figure 7L:
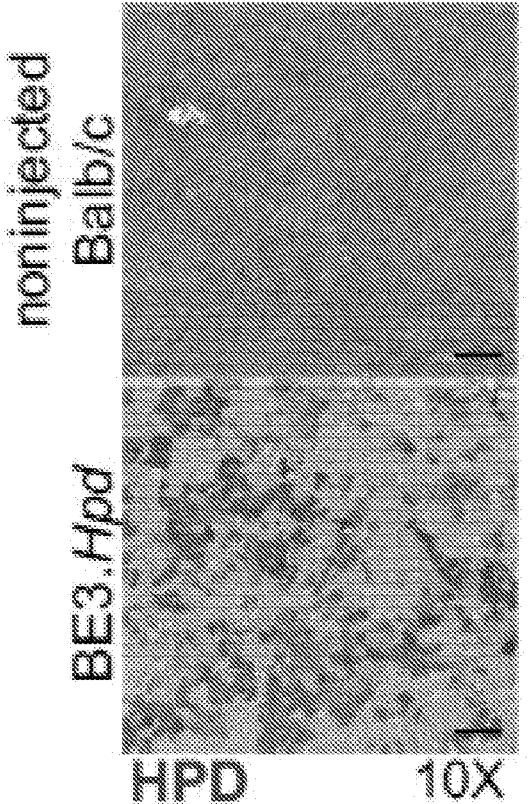
Figure 7M:
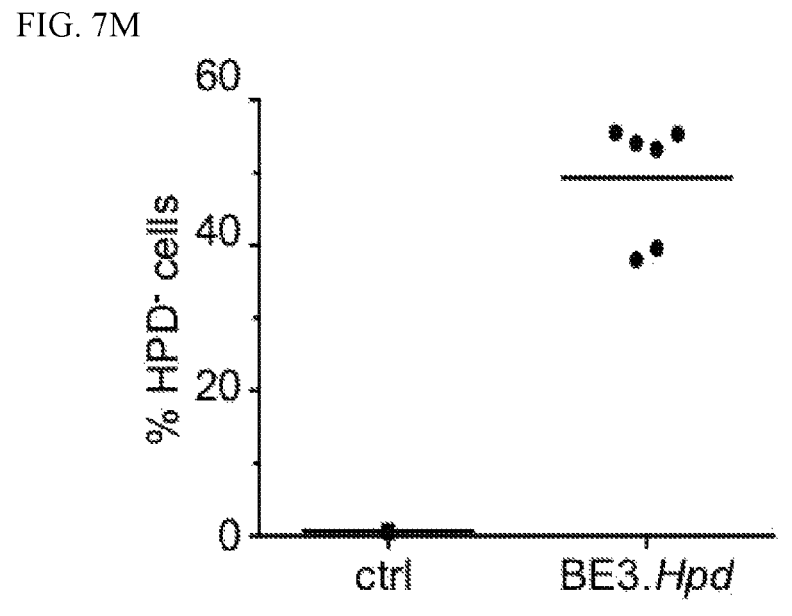

Having demonstrated that in utero base editing resulted in stable rates of Pcsk9 editing, the inventors next sought to target a gene for which the in utero approach would be more clinically relevant. HT1 results from a disruption in the Fah gene in the tyrosine catabolic pathway. Blocking the HPD enzyme in this pathway, as done with the drug NTBC, prevents the accumulation of toxic metabolites and rescues the lethal phenotype (FIG. 8). We sought to evaluate in utero base editing to introduce a nonsense mutation in the Hpd gene as a mechanism to permanently knock out the gene. The inventors initially screened 8 potential sites/guide RNAs (gRNAs) in vitro in Neuro-2a (N2a) cells and found base editing activity by Surveyor assay at the Q309 and Q352 codons, with the greatest activity at Q352 (FIGS. 7C and 7D).

The inventors next tested in vivo prenatal base editing of the Hpd gene by intravenous injection of E16 Balb/c fetuses with an Ad vector containing BE3 and the gRNA targeting the Q352 codon (Ad.BE3.Hpd). Mice were analyzed at 2 weeks of age and demonstrated efficient on target base editing of liver genomic DNA with a mean rate of editing of ~15% by NGS analysis. Analysis of genomic DNA from the heart, lung, and brain of injected mice did not demonstrate any editing activity by Surveyor assay.

Immunohistochemical analysis of the livers from Ad.BE3.Hpd injected mice demonstrated a significant reduction in HPD+ cells compared to noninjected control mice (FIG. 7).

Figure 3E:
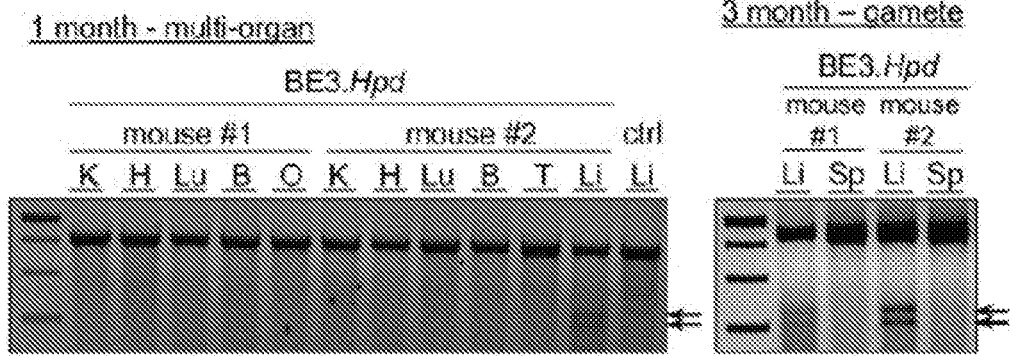

Fah–/– mice, a model of HT1, experience neonatal lethality and can be rescued with the drug NTBC delivered in the breast milk following maternal administration. Having demonstrated that significant Hpd base editing could be achieved following in utero Ad.BE3.Hpd administration in non-diseased mice, the inventors next tested the ability to rescue the lethal phenotype in Fah$^{-/-}$ mice. Fah$^{-/-}$ adult mice maintained on NTBC were mated, and E16 Fah$^{-/-}$ fetuses were intravenously injected with Ad.BE3.Hpd. Injected fetuses were placed with foster moms which were not receiving NTBC on DOL1. Mice were assessed for genome editing and phenotype correction at either DOL1, 1 month of age, or 3 months of age (FIG. 3A). The inventors observed editing in liver genomic DNA of mice prenatally injected with Ad.BE3.Hpd at all time points assessed (FIGS. 3B, 3C. Interestingly, the levels of editing were significantly higher in mice analyzed at 1 month and 3 months of age compared to those assessed at DOL1 (% edited alleles in liver by NGS: 37.2% and 40% vs 13.5%). This increase in editing is likely due to the survival advantage and subsequent expansion of edited cells 26-28. In addition to the expected C→T change at the target site, we observed a low percentage of alternative mutations resulting in additional nonsense and missense mutations (FIG. 3D. In contrast to the high percentage of on-target base edited alleles, the indel burden was significantly lower (~4%). Surveyor assays performed on genomic DNA isolated from other organs at 1 month of age failed to demonstrate any significant activity suggesting that Hpd editing was limited to the liver (FIG. 3E). Finally, NGS analysis of 10 top predicted off-target sites in liver genomic DNA harvested at 1 month of age from 2 mice that received Ad.BE3.Hpd in utero did not demonstrate any editing in excess of that seen in a control mouse (FIG. 3F).

Prenatal base editing to introduce a STOP codon in the Hpd gene rescued the lethal phenotype in Fah$^{-/-}$ mice following withdrawal of NTBC at birth. In contrast to fetal recipients of the control Ad.BE3.Null vector, all of which lost weight prior to death and did not survive beyond 21 days of life, fetal recipients of Ad.BE3.Hpd demonstrated appropriate weight gain with 89% survival at 3 months of age (FIGS. 4A, 4B). Interestingly, the weight gain of Ad.BE3.Hpd injected mice was improved at 1 month of age compared to noninjected Fah$^{-/-}$ mice maintained on NTBC, though weight gain beyond 1 month was not significantly different between the two groups. Additionally, liver function of fetal recipients of Ad.BE3.Hpd and Fah$^{-/-}$ mice maintained on NTBC was similar at 1 month and 3 months of age and significantly improved compared to recipients of Ad.BE3.Null prior to their death. Improved survival and liver function in fetal recipients of Ad.BE3.Hpd correlated with a significant reduction in HPD+ cells noted on immunohistochemistry at DOL1 (FIGS. 4A-4C) and one month of age. Furthermore, histologic analysis of the liver at 1 month of age in recipients of Ad.BE3.Hpd did not reveal any significant inflammation or abnormality in contrast to Ad.BE3.Null injected control mice in which variability in nuclear size and apoptotic hepatocytes consistent with liver injury were evident.

As mentioned above, HT1 results from a mutated FAH gene blocking the tyrosine catabolic pathway (FIG. 7C). inhibiting the upstream HPD enzyme in this pathway with the drug NTBC prevents the accumulation of toxic metabolites and rescues lethal liver failure. CBEs are capable of making site-specific C→T or G→A changes in the coding sequences of genes. Thus, CBEs can introduce precise nonsense mutations to silence target genes. A CBE can introduce nonsense mutations in the human and mouse HPD genes and that prenatal base editing to silence the Hpd gene in vivo will rescue the lethal phenotype in the Fah$^{-/-}$ mouse model. Furthermore, we hypothesize that long-term phenotypic changes in the Fah$^{-/-}$ mouse model will be improved following prenatal Hpd silencing compared to NTBC treatment after birth based on our recently published study in which the lethal phenotype in the HT1 mouse model was rescued following in utero BE3-mediated silencing the Hpd gene using adenovirus as a delivery vehicle (BE3 is a commonly used CBE). In this study the BE3-treated mice demonstrated improved weight gain compared to NTBC-treated mice. Adenovirus was chosen for these initial proof-of-concept studies because the large size of BE3 (~5.1 kb) preempts its delivery in an AAV (packaging capacity ~4.7 kb). Although encouraging, adenoviral vectors have limitations for clinical translation related to adverse host immune responses. These initial studies can be extended via delivery of a CBE and the Hpd-targeting gRNA in AAV8 using an AAV8 split CBE-intein fusion construct as recently demonstrated and by delivery of CBE mRNA (custom-made by TriLink Biotech) in LNPs. Mouse models provide an invaluable resource for assessment of gene-editing approaches in vivo. Among other benefits, mouse models can recapitulate some or all of a human disease phenotype and allow the study of phenotype correction by gene editing. However, mouse models do not allow for accurate assessment of on-target and off-target mutagenesis by CRISPR-Cas9 gene editing against a human gene secondary to the lack of conservation across genomes.

Figure 9:
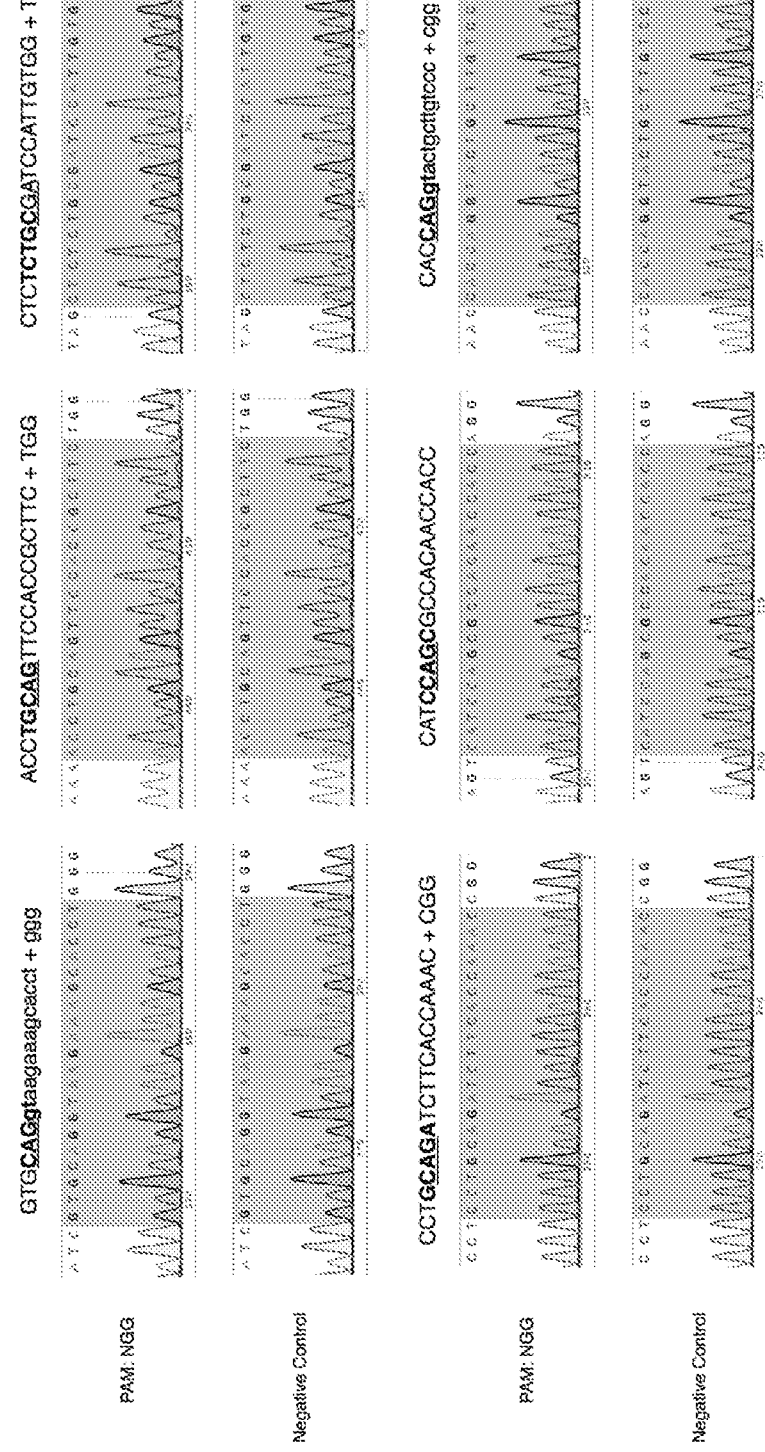
FIG. 9 shows the testing of six human guide RNAs against the human HPD gene in conjunction with base editor 4 (BE4) in HEK 293 cells (human-derived cultured cell line). This is the human version of the tyrosinemia-related gene studied in the mouse, as described infra. PCR amplicons of the target sites were subjected to Sanger sequencing. The listed sequences are the protospacer+ PAM sequences for each guide RNA (capital letters indicate exonic sequence, lower-case letters indicate intronic sequence). The underlined portion of each sequence is the codon to be changed to a stop codon by virtue of a cytosine-to-thymine change (nonsense mutation). The fifth and sixth guide RNAs tested displayed evidence of the desired cytosine-to-thymine changes, whereas the other guide RNAs showed no evidence. Top row: SEQ ID NOS: 30, 31, 32; Third row: SEQ ID NOS: 33, 34, and 35.

To fully assess the safety and efficacy of CRISPR-Cas9 editing, preclinical models in which somatic in vivo gene editing of human genes in normal human cells (i.e., not tumor cells) with human genomes can be performed. We have identified gRNAs for CBEs that result in significant editing and introduction of nonsense mutations in the human HPD gene (FIG. 9)

We can employ chimeric liver-humanized mice bearing human hepatocytes to assess the safety and efficacy of CBE-mediated silencing of the human HPD gene in human hepatocytes in vivo. One of the best-established chimeric liver-humanized mouse models is the Fah–/– Rag2–/– I12rg–/– (FRG KO) model. This model takes advantage of the immunocompromised (Rag2–/–I12rg–/–) and fumarylacetoacetate hydrolase deficient (Fah–/–) background to provide a competitive survival advantage to transplanted human hepatocytes without immune rejection. We have previously used this model to assess in vivo CRISPR mediated gene editing to silence the human PCSK9 gene.

In Utero Viral Vector Targeting of the Liver.

Figures 10A, 10B, 10C, 10D:
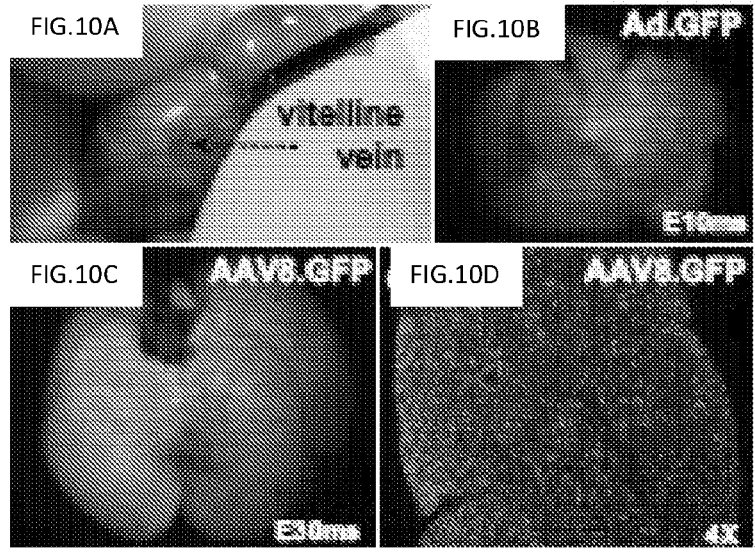
FIGS. 10A-10D. In utero viral vector delivery.

We have a reliable and reproducible mouse model in which vitelline vein injection results in efficient targeting of the fetal liver (FIG. 1A). The vitelline vein runs along the mouse uterine wall and drains directly into the portal circulation, providing first-pass effect to the liver. We have demonstrated robust transduction of hepatocytes via adenovirus and AAV8 injections into E16 (gestational day 16) fetuses via the vitelline vein (FIG. 10B, 10D).

In Utero CRISPR-Mediated NHEJ in the mTmG Model.

mTmG mice have a two-color fluorescent Cre-reporter allele (mT-tdTomato: red; mGEGFP: green) in which the mT cassette is flanked by LoxP sites. Mice constitutively express tdTomato in all cells until deletion of the mT cassette, which allows expression of EGFP.

We have designed SpCas9 gRNAs specific for the LoxP sites (SpCas9.mTmG). Thus, successful editing via NHEJ results in excision of the mT gene (detectable by PCR) and is indicated by expression of green fluorescence (detectable by flow cytometry and immunohistochemistry, IHC). In this tractable model, we have demonstrated efficient hepatocyte editing following in utero i.v. (intravenous) delivery of SpCas9.mTmG in an adenovirus as well as an intein-mediated dual AAV9 system to E16 fetuses (FIG. 5). Hepatocyte editing was followed and noted to be stable up to 6 months of age (the last time point of analysis).

In Utero Base Editing to Silence a Gene.

As described above, we have demonstrated efficient introduction of nonsense mutations in the Pcsk9 and Hpd genes resulting in reduction in cholesterol levels following Pcsk9 targeting in normal mice and rescue of the HT1 phenotype following Hpd targeting in Fah–/– mice. Prenatal base editing resulted in long-term persistence of edited cells in contrast to postnatal editing in which a significant drop in the number of edited cells associated with an anti-viral and SpCas9 immune response was noted.

In Vitro Intein-Mediated Base Editing.

Figure 11A:
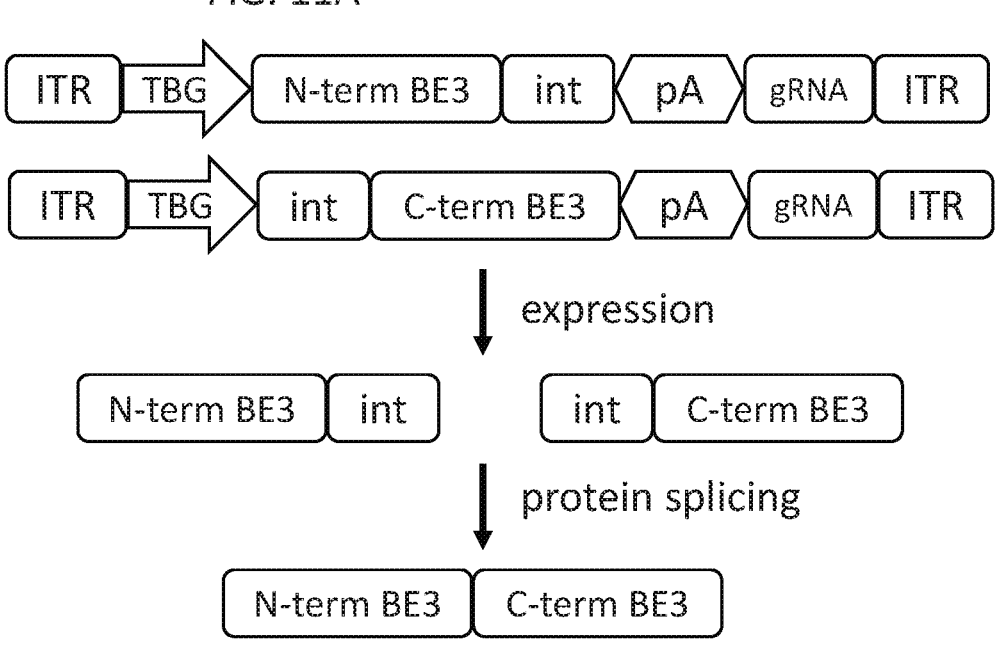
FIGS. 11A-11B. In vitro intein-mediated base editing.
Figure 11B:
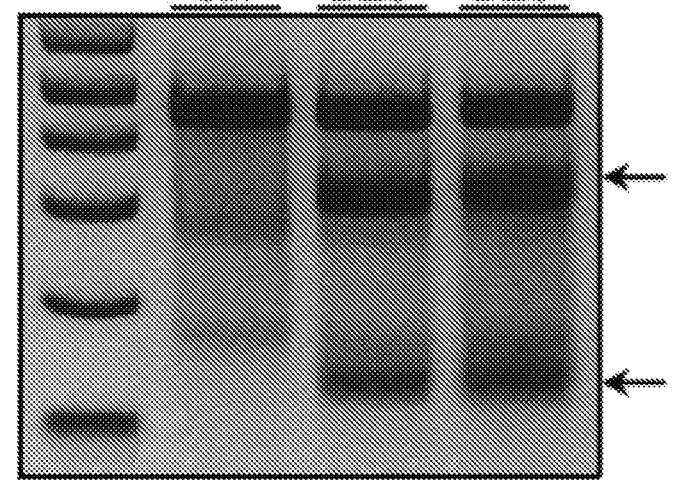

AAV8 vectors can be used to deliver base editors to the fetal liver in utero. Given the size of the base editor and the limited packaging capacity of AAV8, we will use an intein system to split the base editor for its packaging into two AAV8 viruses. Upon transduction of a cell by both viruses, intein-mediated recombination will allow for a functional base editor. This system has been shown to be feasible by other groups, and we have demonstrated the feasibility of this system in vitro in preliminary studies (FIG. 11).

LNP-Mediated Base Editing.

We have recently demonstrated the feasibility of in utero targeting of the fetal liver with LNPs delivered via the vitelline vein. LNPs, loaded with SpCas9 mRNA and a gRNA targeting Pcsk9, were delivered in utero and demonstrated efficient hepatocyte editing 5 days after delivery (FIG. 12).

Base Editing of Human Cells in a Liver Humanized Mouse Model.

A CBE can be used to silence the human HPD gene in vivo in a mouse model in which the endogenous hepatocytes have been replaced by human hepatocytes. As an initial step, we have screened gRNAs for conversion of glutamine and tryptophan amino acids to nonsense mutations by CBEs in vitro and identified two with significant editing activity (FIG. 9). We will use the FRG KO mouse model, which is a well-established model of a chimeric-liver humanized mouse, to investigate in vivo base editing to silence the human HPD gene.

Viral and LNP-Mediated Prenatal Delivery of a CBE to Introduce Nonsense Mutations in the Hpd Gene in the HT1 Mouse Model and Rescue of the Lethal Phenotype.

Fah$^{-/-}$ mice on NTBC will be time-dated and E16 fetuses injected via the vitelline vein with adenovirus, AAV8, or LNPs containing BE3 and the Hpd targeting gRNA (BE3.mHpd). The LNPs will contain BE3 mRNA (obtained from TriLink BioTechnologies) and Hpd gRNA (obtained from Axolabs GmbH) that have been optimized for stability. At birth, injected pups will be fostered with BALB/c wild-type mice not on NTBC to remove the drug from the diet. Control mice will consist of fetuses injected with BE3 and a gRNA not specific for any mouse DNA sequence (BE3.Null) and uninjected Fah-/- fetuses maintained on NTBC. Mice will be serially weighed and monitored for survival. Liver function will be monitored by measuring serum alanine transaminase (ALT), aspartate transaminase (AST), and total bilirubin levels at 1, 3, 6, and 12 months of age or prior to death in BE3.Null treated animals (at ~21 days based on previous work). Mice will be sacrificed at 1, 3, and 12 months of age and DNA from the liver, brain, heart, lungs, kidney, and spleen will be assessed for on-target Hpd editing via Surveyor assays and next-generation sequencing (NGS). Whole-genome sequencing (WGS) and long-read sequencing will be performed on liver DNA from 3 mice with evidence of the highest on-target editing rates at 1 month of age to determine, in an unbiased fashion, the incidence of off-target mutations and unwanted on-target large deletions and rearrangements. At the time of sacrifice, liver HPD protein expression will be assessed by IHC in experimental and control mice and quantified using the Aperio ImageScope software (Leica Biosystems) as we have previously done. We anticipate that prenatal base editing to silence the Hpd gene is more efficacious and safer than lifelong NTBC treatment. Similar to humans, Fah$^{-/-}$ mice maintained on NTBC have an increased risk of developing liver tumors as demonstrated by a 50% incidence of HCC and/or hepatomas at 10 months of age in this model. Although we saw no evidence of liver tumors in prenatally edited Fah-/- mice at 1 or 3 months of age, long-term studies are necessary to assess lifetime risk. Thus, in addition to comparing weight gain and liver function between prenatally base edited Fah$^{-/-}$ mice and Fah$^{-/-}$ mice on NTBC, a focused exam and histologic analysis of the liver can be performed, with specific attention to the presence of tumors, in the 12-month-old mice, to assess any benefit (or detriment) of prenatal base editing vs. life-long NTBC treatment.

Target Human HPD Gene in Human Hepatocytes In Vivo in Liver-Humanized Mice.

To assess in vivo base editing of the human HPD gene in human hepatocytes, FRG KO breeder mice will be obtained from Yecuris Corporation. Prior to human hepatocyte transplantation, mice are maintained on NTBC, which prevents death of the Fah-/- hepatocytes. At 1 to 3 months of age, 1×10$^6$ primary human hepatocytes (HEP10 Pooled Human Cryopreserved Hepatocytes; Thermo Fisher Scientific) will be injected into the lower pole of the spleen. Twenty four hours prior to hepatocyte transplantation, mice are injected intraperitoneally with an adenovirus expressing the secreted form of urokinase-type plasminogen activator (Yecuris) that increases the efficiency of human hepatocyte engraftment. Following transplantation, NTBC is withdrawn, resulting in death of endogenous Fah$^{-/-}$ hepatocytes and providing a survival advantage to the transplanted human hepatocytes. The serum of mice will be monitored for human albumin levels; a surrogate for the degree of human hepatocyte liver reconstitution. This model has been demonstrated to result in greater than 90% human hepatocyte engraftment. Once human hepatocyte reconstitution is confirmed, mice can be injected via the tail vein with BE3 and human HPD gRNA (BE3.hHPD) delivered in either adenovirus, AAV8, or LNPs. Controls will consist of mice injected with the BE3 and a gRNA not specific for any sequence in the human genome. Mice will be sacrificed at 1 and 6 months after injection, and liver DNA will be assessed by NGS for on-target HPD editing. Long-read sequencing will be performed to assessed for unwanted large deletions or complex rearrangements at the HPD target site. Since the injected human hepatocytes are from a pooled source, a baseline genome does not exist to allow comparison for WGS. Thus, the top 20 off-target sites as predicted by CRISPOR and ranked by the mitOfftargetScore will be assessed by NGS to determine off-target mutagenesis events. Finally, livers will also be assessed for HPD protein expression by immunohistochemistry at the time of sacrifice.

Although we do not anticipate high rates of off-target effects or unwanted on-target mutations based on the mechanism of action of base editing, the functional effect of these potential events can also be assessed. We know from previous studies that edited hepatocytes constitute greater than 90% of hepatocytes by 1 month post-editing (FIG. 8). We will harvest hepatocytes from prenatally edited Fah$^{-/-}$ mice and postnatally edited liver-humanized mice at one month and serially transplant them into adult FRG KO mice. Mice will be monitored for 1 year at which time the liver will be assessed for nodules and the development of HCC by histologic analysis.

Although base editing to silence the HPD gene will result in a significant reduction in morbidity, mortality, and health care resource utilization for HT1 patients, and this approach is relevant to other metabolic liver diseases (e.g., alpha-1 antitrypsin deficiency), it does not fix the underlying disease-causing mutation in the FAH gene. Due to a founder effect, HT1 is most prevalent in the Quebec region of Canada, a G→A splice site mutation in the FAH gene accounts for greater than 90% of disease-causing mutations. Similarly, the disease-causing mutation in the Fah$^{-/-}$ mouse is a G→A mutation in the Fah gene. Previous studies of postnatal CRISPR-mediated gene editing in the Fah$^{-/-}$ mouse resulted in low initial levels of mutation correction by HDR (0.8%) and high levels of unwanted NHEJ-induced indels (24%-26%). Inefficient HDR in these studies is due, in part, to the lack of proliferating target hepatocytes at the time of editing. Furthermore, the DSBs required to instigate HDR have been shown to be associated with an increased risk of off-target mutations and unwanted on-target large deletions and complex rearrangements. The ABE consists of a catalytically impaired SpCas9 protein (unable to make DSBs) that is capable of converting A→G in a site-specific fashion. In addition to being potentially safer, the ABE does not require proliferating cells to function efficiently. We anticipate that prenatal delivery of the ABE and Fah-targeting gRNA via viral and nonviral delivery mechanisms in Fah$^{-/-}$ mice will correct the mutation and rescue the lethal phenotype. Furthermore, we hypothesize that the ABE can efficiently correct the disease-causing FAH G→A mutation in a human 293 cell line which we have engineered to express this mutation. This hypothesis is based on our preliminary studies in Fah$^{-/-}$ mice in which ABE6.3 and a gRNA targeting the Fah mutation ameliorated the disease phenotype following postnatal hydrodynamic tail vein injection (FIG. 13), our published study demonstrating our ability to perform in utero base editing with BE3 (FIG. 8), and our studies demonstrating our ability to achieve in utero SpCas9 and BE3-mediated editing following adenovirus, AAV, and NP-mediated delivery.

ABE to Correct the Fah Mutation In Vivo in the HT1 Mouse Model.

Figure 13:
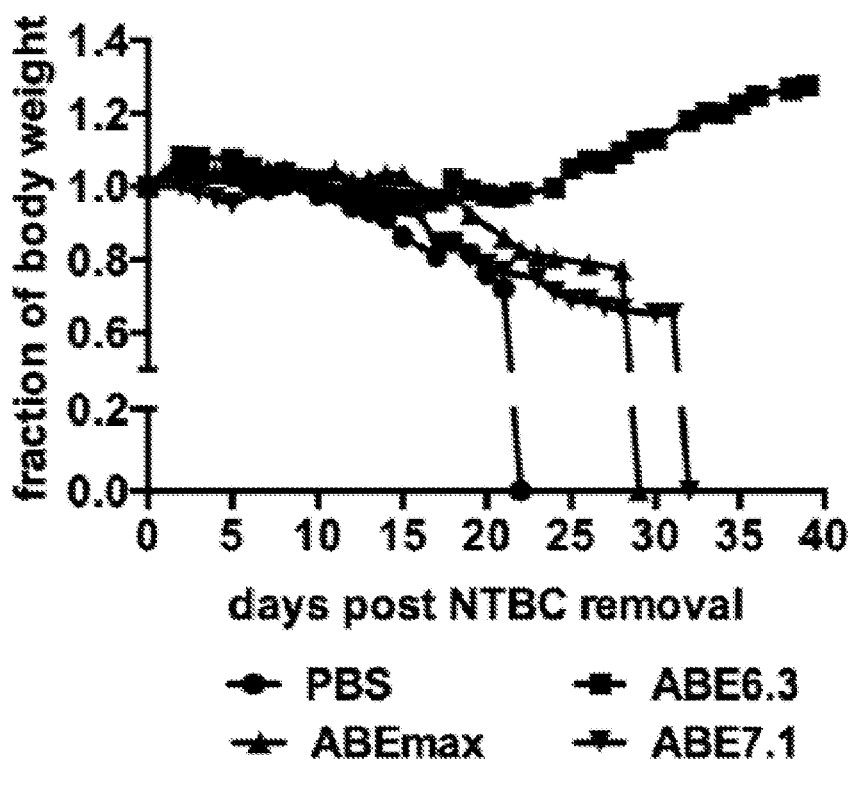
FIG. 13. Rescue of the lethal HT1 phenotype with ABE correction of the Fah gene. 6-week-old Fah−/− mice underwent hydrodynamic tail vein injection with PBS or plasmids containing ABEMax, ABE6.3, or ABE7.1 and a gRNA targeting the Fah G→A mutation. NTBC was removed 3 days post injection and mice were serially weighed. Weights adjusted to weights on the day of NTBC removal.

The G→A mutation in the Fah gene appears to be amenable to correction via the ABE. The target mutated adenine is located at position 9 of the protospacer sequence (11 bases upstream from the PAM sequence) and is thus just outside of the predicted editing window of ABE7.1. ABE6.3, however, has demonstrated editing activity at this position. We screened plasmids containing ABE7.1, ABEmax (optimized ABE 7.1), and ABE6.3 and the gRNA targeting the Fah mutation in the HT1 mouse model in vivo via hydrodynamic tail vein injection into 6-week-old mice. Mice were removed from NTBC 3 days following tail vein injection and monitored for survival. In contrast to control uninjected mice and those injected with ABE7.1 and ABEmax, the Fah-/- mouse injected with ABE6.3 continues to survive and gain weight off of NTBC, suggesting correction of the Fah mutation (FIG. 13).

Introduction of the Quebec Mutation into Human HEK 293 Cells and ABE-Mediated Correction of the Mutation.

We noted that the location of the Quebec founder G→A mutation, in an intron 5 bases downstream of the exon-intron junction, lies within the editing window of BE3 when oriented to a PAM in the antisense strand (FIG. 14). Using the appropriate gRNA, we used BE3 to introduce the desired sense strand G→A change in HEK 293 cells. In our experiment, because there were multiple cytosines within the BE3 editing window, we obtained cells with a variety of edited alleles. None of the clonal cell lines we screened had the Quebec mutation alone. We chose a clonal cell line with an allele with the Quebec mutation and an additional upstream G→A edit. We then used ABE7.1 with a gRNA that placed the Quebec mutation within the adenine editing window. The gRNA had two mismatches to the reference genome sequence, corresponding to the Quebec mutation and the additional upstream G→A edit. Upon delivery of ABE7.1 and the gRNA into the clonal edited HEK 293 cell line, followed by NGS of the target site, we observed that 9% of the target alleles were successfully edited so as to restore the Quebec mutation to the wildtype state (i.e., an A→G edit) (FIG. 14). Of note, a large proportion of the alleles had additional AáG edits within the adenine editing window of ABE7.1.

Viral and LNP-Mediated Prenatal Delivery of an ABE to Correct the Causal G→a Mutation in the Fah Gene and Rescue the Lethal Phenotype in the HT1 Mouse Model.

E16 Fah$^{-/-}$ fetuses will be injected via the vitelline vein with adenovirus, AAV8, or LNPs containing ABE6.3 and the Fah targeting gRNA (ABE6.3.mFah). ABE6.3 has been chosen because, compared to other ABE versions, it resulted in higher rates of editing adenines in position 9 of the base editing window, the position of the target adenine in the Fah gene9. At birth, injected pups will be fostered with BALB/c wild-type mice not on NTBC. Control mice will consist of fetuses injected with ABE6.3 and a gRNA not specific for any DNA sequence in the mouse genome (ABE6.3.Null) as well as uninjected Fah-/- fetuses maintained on NTBC. We will assess the same outcomes as described above with the exception that histologic analysis of the liver will be for FAH protein expression instead of HPD expression. Briefly, hepatocytes from prenatally edited mice will be harvested and serially transplanted into FRG KO mice, which will be analyzed at 1 year post-transplant for HCC and other untoward functional effects of prenatal base editing.

Production of a Human Cell Line Containing the Quebec Mutation and Correct the Mutation with an ABE.

We have already used base editing with BE3 to introduce the Quebec founder G→A mutation in the FAH gene in human HEK 293 cells, albeit with an extra G→A mutation. Additional base-edited clones can be screened to identify one that has only the Quebec mutation. In an alternative approach, we will use standard SpCas9 with a single-strand DNA oligonucleotide to perform HDR knock-in of the Quebec mutation. To obtain a clone that is heterozygous for a "clean" Quebec mutation allele and a second allele (whether wild-type or mutant), we will use SpCas9 with two flanking gRNAs to delete a large portion (>1 kb) of the second allele, which will render the clone hemizygous for the Quebec mutation.

The desired clonal edited cell line (referred to as 293.FAH cells), can be fully characterized including quantification of FAH gene transcription by quantitative reverse transcriptase-PCR (qRT-PCR) and FAH protein production by immunoblotting in 293.FAH cells compared to unedited control cells. After characterizing the 293.FAH cells, we will screen gRNAs and different ABEs (ABE6.3, 7.1, max, 7.8, and 7.9; all available from Addgene) for the ability to correct the G→A mutation in the human FAH gene. For this screening, 293.FAH cells will be transfected with a plasmid containing the ABE and a second plasmid containing the gRNA. Controls will consist of 293.FAH cells transfected with the plasmid containing the ABE but no gRNA. DNA will be isolated from the cells and on-target FAH editing will be assessed by Surveyor assays, Sanger sequencing, and NGS to evaluate the specific DNA changes that occurred. The top 20 off-target sites as predicted by CRISPOR and ranked by the mitOfftargetScore will be assessed by NGS to determine off-target mutagenesis events. We will also obtain clonal cell lines following ABE editing and assess the phenotypic effect of correction of the FAH mutation (with or without additional adenine edits) via the ABE by quantifying FAH gene transcription Homologous recombination to introduce the wild-type FAH gene into its endogenous locus or into the locus of a highly expressed liver protein, e.g., albumin, offers the potential of correcting the genetic disease without correction of the underlying mutation. Recently, the use of CRISPR-mediated editing to put genes in their endogenous loci via HDR has been used to address genetic diseases which do not have a single common mutation as the cause, such as hemophilia. Although beneficial, this carries with it the increased risks associated with the necessary DSBs inherent to CRISPR-mediated editing. As an alternative, endonuclease free HDR has been used to place the corrective genes for hemophilia and alpha-1-antitrypsin within the albumin locus via a promoter-less AAV system. A limitation to both CRISPR-mediated and endonuclease-free HDR approaches is the low efficiency of recombination due, in part, to the lack of proliferation of the target cell population. As discussed above, a potential benefit of the fetal recipient is the large number of accessible highly proliferative cells, particularly in the fetal liver. Furthermore, the selective survival advantage of corrected hepatocytes in the HT1 model will allow them to expand to fill the liver and suggests that this approach, even at a relatively low efficiency, will be effective to cure the disease.

Figure 15:
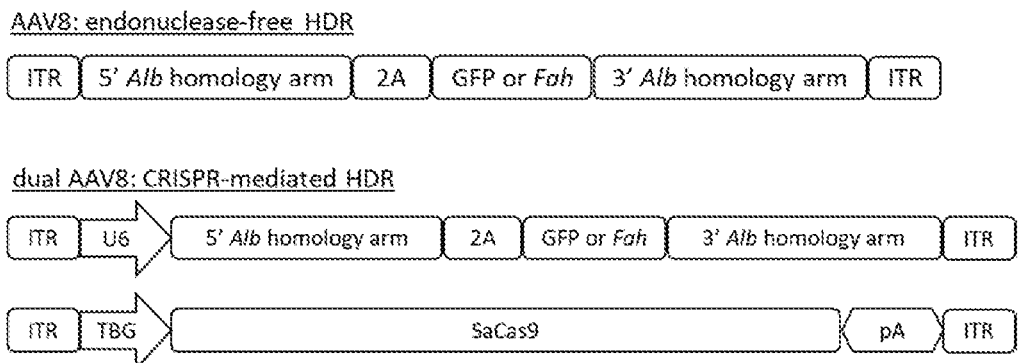
FIG. 15. Endonuclease-free and CRISPR-mediated HDR. Schematic representation of the AAV8 systems used to compare endonuclease-free and CRISPR-mediated integration of GFP or Fah into the albumin locus for prenatal and postnatal gene editing.

It appears that prenatal CRISPR-mediated and endonuclease-free HDR will be more efficient compared to a postnatal approach and that endonuclease-free HDR will be safer with less unwanted on- and off-target mutations than CRISPR-mediated HDR. Furthermore, we hypothesize that prenatal CRISPR-mediated and endonuclease-free HDR to place the Fah gene in the albumin locus will rescue the disease phenotype in Fah$^{-/-}$ mice. This hypothesis can be tested using a promoter-less AAV8 to target the liver. The transgene will include 5' and 3' albumin homology arms as well as either endonuclease-free HDR. For CRISPR-mediated HDR, we will use a dual AAV8 system—one AAV containing Staphylococcus aureus Cas9 (SaCas9) expressed from a liver-specific promoter and the other AAV containing the gRNA targeting the albumin locus along with the Fah or GFP transgene (FIG. 15). The rationale for this approach is that it will provide a universal approach, independent of the underlying Fah mutation, to correct the HT1 phenotype and that it will exploit the natural properties of the fetus to facilitate a non-CRISPR-mediated, potentially safer approach for HDR. This approach should also be applicable to other metabolic liver diseases in addition to HT1.

In Utero Endonuclease-Free Homologous Recombination.

Figure 16:
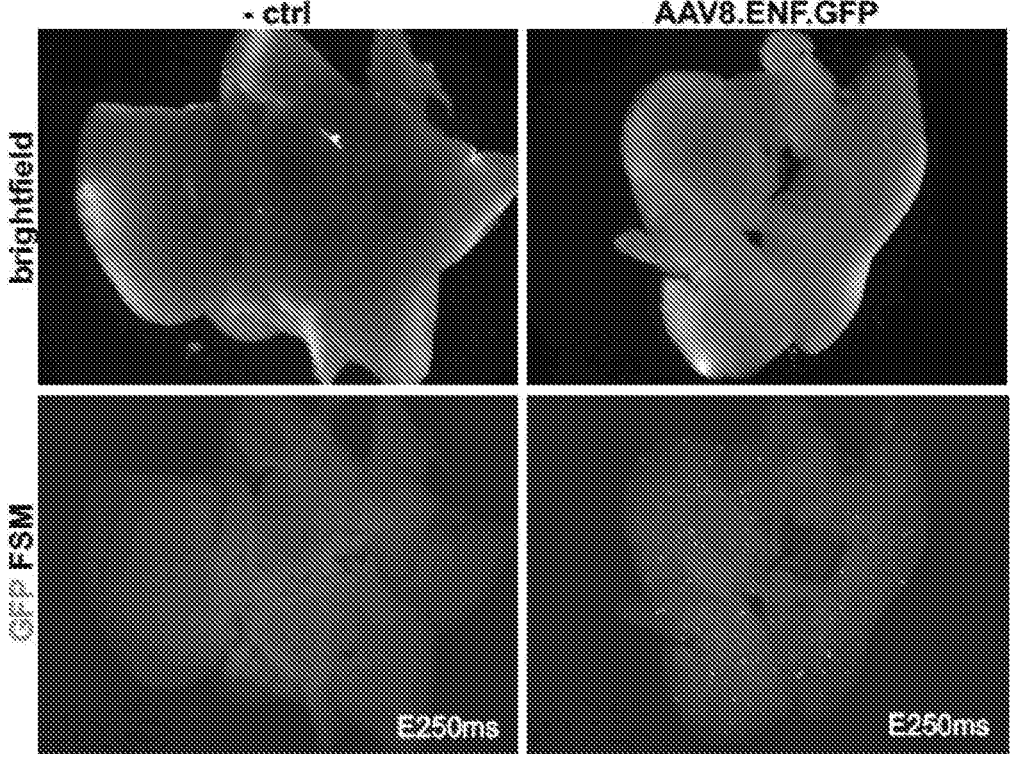
FIG. 16. In utero endonuclease-free HDR. E16 BALB/c fetuses were injected with AAV8.ENF.GFP, a promoter-less AAV targeting the GFP transgene for integration in the albumin locus. Livers were harvested 5 days after injection and assessed by stereomicroscope. In contrast to uninjected fetuses (−ctrl), injected fetuses demonstrated discrete areas of green fluorescence suggesting successful integration of the GFP transgene. PCR of liver DNA using a forward primer within the GFP transgene and a reverse primer downstream of the 3' Alb homology arm and viral template demonstrated a 1.6 kb band (arrow) consistent with HDR.

We have demonstrated, in preliminary studies, our ability to target the fetal liver with AAV8 (FIG. 10). We next sought to evaluate the feasibility of in utero liver-directed endonuclease free homologous recombination. We have designed a promoter-less AAV8 that contains a 2A-peptide coding sequence and GFP cDNA targeted for integration just upstream of the albumin STOP c odon in the albumin locus via 5' and 3' Alb homology arms (called AAV8.ENF.GFP) (FIG. 15). Integration of the GFP transgene as a 2A-fusion protein in the albumin locus allows for the co-expression of the transgene with albumin and takes advantage of the strong albumin promoter. Using this construct, we have demonstrated liver GFP expression 5 days after vitelline vein injection of AAV8.ENF.GFP into E16 BALB/c fetuses (FIG. 16).

Prenatal Vs. Postnatal CRISPR-Mediated and Endonuclease-Free HDR.

We hypothesize that prenatal CRISPR-mediated and endonuclease-free HDR will be more efficient than a postnatal approach and that CRISPR-mediated HDR will be more efficient than endonuclease-free HDR but will also be associated with higher rates of unwanted on- and off-target mutations. To address this hypothesis, we will use the promoter-less AAV8.ENF.GFP construct in which the GFP cDNA is flanked by Alb homology arms to evaluate endonuclease-free HDR as described above (FIG. 15). This will be compared to the CRISPR-mediated approach which involves a dual AAV8 system in which one virus contains SaCas9 and the other contains the gRNA targeting the albumin locus and the GFP-2A peptide cDNA (FIG. 15). Of note, we have chosen to use SaCas9 instead of SpCas9 due to the limited packaging capacity of AAV and the smaller size of SaCas9. The viral vectors will be injected into E16 BALB/c fetuses via the vitelline vein or into 6-week-old BALB/c adults via tail vein. Outcomes to be assessed include the efficiency of hepatocyte editing via flow cytometry and IHC for GFP-positive hepatocytes as well as PCR for the expected DNA insert if HDR occurred successfully. On- and off-target mutations will be assessed and compared between approaches via NGS of the on-target site and the top 20 predicted off-target sites based on sequence similarity. Control animals will consist of fetuses and adults injected with a promoter-less AAV8 containing the GFP transgene without albumin homology arms and those injected with only the AAV8 containing SaCas9.

Prenatal CRISPR-Mediated and Endonuclease-Free HDR to Cure HT.

To test the hypothesis that prenatal CRISPR-mediated and endonuclease-free HDR can result in precise integration of the wild-type Fah gene in the genome and rescue the lethal phenotype in the HT1 mouse model, we will use similar AAV8 constructs to those described above, with the exception that the GFP cDNA will be replaced with the Fah cDNA. AAV8 vectors will be injected via the vitelline vein into E16 Fah$^{-/-}$ fetuses. At birth, mice will be placed with BALB/c foster moms not on NTBC, thus removing the drug from their diet. Controls will consist of Fah$^{-/-}$ fetuses injected with AAV8 vectors containing the GFP transgene instead of the Fah transgene, from which NTBC will be withheld from the time of birth, and uninjected Fah$^{-/-}$ fetuses that are maintained on NTBC after birth. We will assess for outcomes including weight gain, survival, liver function tests, and liver histology including FAH expression and quantification. Editing will be assessed by PCR for the expected DNA insert in the albumin locus if successful integration occurred. On- and off-target mutations will be assessed and compared between approaches via NGS of the on-target site and the top 20 predicted off-target sites based on sequence similarity. As discussed above, hepatocytes from prenatally edited mice will be harvested and serially transplanted into FRG KO mice, which will be analyzed at 1 year post-transplant for HCC and other untoward functional effects of prenatal CRISPR-mediated and endonuclease-free HDR.

DISCUSSION

CRISPR-Cas9 has garnered excitement for the possibility of curing genetic abnormalities that result in significant morbidity and mortality and for which there exists no adequate treatment. Although many genetic diseases would best be treated with CRISPR-Cas9 genome editing after birth, the natural characteristics of the developing fetus as well as the timing of onset of some diseases make prenatal therapeutic CRISPR-Cas9 genome editing an attractive approach. This is best exemplified by diseases which can be prenatally diagnosed, and which cause significant morbidity and/or mortality before or immediately after birth. Furthermore, diseases in which the deleterious effects of a disease-causing gene begin at or before birth and accumulate throughout the lifetime of the individual may also be better served, one day, from prenatal or early postnatal genome editing.

In addition to being able to treat a disease before symptom onset, prenatal genome editing offers the potential to take advantage of the normal developmental properties of the fetus, including fetal immunologic immaturity and accessible target cell populations, to enhance the likelihood of genome editing success. The ability to induce immune tolerance to a foreign protein secondary to fetal immunologic immaturity by introduction of that protein during development is a concept established by Billingham, Medawar, and others in the 1950s29.

Among the different approaches to deliver Cas9 in vivo, viral vectors have been used in multiple studies and hold promise for clinical application. However, it is well established that a limitation to successful postnatal viral vector-based gene therapy is an immune response to both the viral vector and the transgene product 8, 30. In contrast, studies of in utero viral vector-based gene therapy in large and small animals suggest the lack of an immune response to the viral vector and transgene product with the induction of immune tolerance to the transgene product. Similarly, with respect to CRISPR-Cas9 mediated genome editing, a recent study by Wang et al. demonstrated the induction of anti-SpCas9 antibodies in mice following postnatal adenoviral mediated delivery of SpCas9, and concern about pre-existing Cas9 antibodies in humans secondary to natural infection has been raised. In our current study, elevated levels of anti-Ad and anti-SpCas9 antibodies were demonstrated in the serum of mice injected postnatally with Ad.BE3.Pcsk9 in contrast to those injected prenatally. Interestingly, also noted was the lack of persistence of high levels of edited cells in postnatal recipients Ad.BE3.Pcsk9 at 2 and 3 months of age in contrast to prenatal recipients of Ad.BE3.Pcsk9 in which the editing efficiency remained stable at 5 days and 3 months post injection. Together, these findings suggest that one potential explanation for the loss of edited cells following postnatal administration is an immune response to the viral vector or SpCas9.

In this study we rescued the lethal phenotype of HT1 in the Fah$^{-/-}$ mouse model. HT1 is an attractive model for therapeutic genome editing because corrected cells have a survival advantage and will repopulate the liver. In previous studies in this model, HDR was used to correct the disease-causing mutation following delivery of Cas9, gRNA, and a single strand DNA repair template to adult mice in plasmids via hydrodynamic tail vein injection or in a combined lipid nanoparticle/adeno-associated virus approach. On-target repair rates following HDR, which requires proliferating cells to occur efficiently, were 0.8% by NGS with 0.4-6% FAH+ hepatocytes on immunohistochemistry at 6-7 days following injection. Importantly, at the time of analysis, Fah–/– mice were maintained on NTBC to prevent a competitive advantage for corrected cells. On-target repair rates reached 9% by NGS with 33% FAH+ hepatocytes following 1 month off of NTBC, consistent with a competitive survival advantage conferred by successful genome editing. The Cas9 used in these studies is capable of making DSBs with the potential for high rates of indel mutagenesis which were noted to be 24-26%. In contrast to HDR with Cas9, base editing with BE3 does not require proliferating cells for efficient editing and BE3 is incapable of making DSBs. In our studies we noted a higher initial rate of editing wile on NTBC (13.5% at DOL1) that also dramatically increased following NTBC removal (37% and 40% at 1 and 3 months of age), whereas the indel mutagenesis rate was only 4% following prenatal Ad.BE3.Hpd injection. Finally, a more recent study in the adult Fah$^{-/-}$ model employed hydrodynamic tail vein injection to deliver plasmids containing Cas9 and gRNAs targeting introns adjacent to exons 3 and 4 of the Hpd gene2. This study employed CRISPR-Cas9 to excise exons 3 and 4 via NHEJ to silence the Hpd gene. This study demonstrated improved survival and editing efficiencies of 15% and 63% by NGS at 1 and 4 weeks post treatment, with 92% HPD-negative hepatocytes on immunohistochemistry by 8 weeks post treatment. Similarly, using the catalytically impaired and thus potentially safer BE3, the inventors demonstrated 95% HPD-negative hepatocytes at 1 month of age with 89% survival at 3 months of age and normal liver function.

One potential benefit of genetically silencing the Hpd gene as opposed to pharmacologic inhibition of HPD with NTBC is a more complete block of tyrosine catabolism with subsequent decreased risk of developing hepatocellular carcinoma (HCC). In children diagnosed with HT1, treatment with NTBC has significantly improved outcomes but has not completely eliminated the risk of HCC and need for a liver transplant. Interestingly, the initiation of NTBC in children less than 1 month of age results in a significant reduction in the need for liver transplant compared to those who begin treatment after 1 month. This raises the possibility that even earlier silencing of the Hpd gene, perhaps prior to birth, would result in even better outcomes. Similar to humans, Fah$^{-/-}$ mice maintained on NTBC have an increased risk of developing liver tumors as demonstrated by a 50% incidence of HCC and/or hepatomas at 10 months of age in this model. The inventors saw no evidence of liver tumors in prenatally edited Fah$^{-/-}$ mice at 1 or 3 months of age, though longer-term studies will be needed to assess the lifetime risk.

We have established the feasibility of in utero CRISPR-mediated therapeutic editing of metabolic genes. We highlight prenatal base editing to target a gene involved in a chronic medical condition as well as the more clinically relevant approach of treating a congenital genetic disease that has the potential to result in death in the early postnatal period. Improved delivery techniques combined with the flexibility of the CRISPR-Cas9 system, the natural developmental properties of the fetus, and advances in prenatal care such that most genetic abnormalities can be diagnosed before birth, offer hope for the potential of prenatal genome editing to shift the therapeutic paradigm for devastating congenital diseases which currently have no adequate treatment.

Many inherited diseases, including sickle cell anemia, hemophilia and cystic fibrosis, are caused by mutations within a single gene. We know of 10,000 single-gene conditions and together, they affect about one in 100 births.

Beta Thalassemia

Beta thalassemia is a blood disorder that reduces the production of hemoglobin. Beta thalassemia is classified into two types depending on the severity of symptoms: thalassemia major (also known as Cooley's anemia) and thalassemia intermedia. Of the two types, thalassemia major is more severe.

Mutations in the hemoglobin subunit beta (HBB) gene cause beta thalassemia. Thus far, close to 400 mutations in the HBB gene have been found to cause beta thalassemia. Most of the mutations involve a change in a single DNA building block (nucleotide) within or near the HBB gene. Other mutations insert or delete a small number of nucleotides in the HBB gene.

HBB gene mutations that decrease beta-globin production result in a type of the condition called beta-plus (B$^+$) thalassemia. Mutations that prevent cells from producing any beta-globin result in beta-zero (B$^0$) thalassemia.

Problems with the subunits that make up hemoglobin, including low levels of beta-globin, reduce or eliminate the production of this molecule. A lack of hemoglobin disrupts the normal development of red blood cells. A shortage of mature red blood cells can reduce the amount of oxygen that is delivered to tissues to below what is needed to satisfy the body's energy needs. A lack of oxygen in the body's tissues can lead to poor growth, organ damage, and other health problems associated with beta thalassemia.

The HBB gene encodes a protein called beta-globin, which is a subunit of hemoglobin. Hemoglobin consists of four protein subunits, typically two subunits of beta-globin and two subunits of another protein called alpha-globin.

Some mutations in the HBB gene entirely prevent the production of beta-globin. The absence of beta-globin is referred to as beta-zero ($B^0$) thalassemia. Other HBB gene mutations allow beta-globin to be produced in reduced amounts. A reduced amount of beta-globin is called beta-plus ($B^+$) thalassemia. Having either $B^0$ or $B^+$ thalassemia does not necessarily predict disease severity, however; people with both types have been diagnosed with thalassemia major and thalassemia *intermedia*.

A lack of beta-globin leads to a reduced amount of functional hemoglobin. Without sufficient hemoglobin, red blood cells do not develop normally, causing a shortage of mature red blood cells. The low number of mature red blood cells leads to anemia and other associated health problems in people with beta thalassemia.

A fetus of a patient is determined by prenatal genetic testing to have a mutation in a single nucleotide in the G23X (HBB) gene that causes a premature stop codon. The present in utero gene editing is used to target the mutated HBB gene in the fetus and base editing this HBB gene to correct the single-nucleotide mutation, thereby allowing the HBB gene to produce beta-globin. Postnatally, the infant has no abnormality in the G23X (HBB) gene and does not exhibit any phenotype associated with G23X (HBB) deficiency.

Huntington's Disease

Huntington's Disease (HD) is a progressive brain disorder that causes uncontrolled movements, emotional problems, problems in communication, mental processes and movement, and loss of thinking ability (cognition). HD is caused by a mutation in the Huntington (HTT) gene, which encodes the protein huntingtin. The HTT mutation, a specific tri-nucleotide sequence, the CAG segment, is repeated 36 to more than 120 times. Although "environmental" factors such as exercise may slow Huntington's progression, the number of CAG repeats accurately predicts the age of illness onset. For example, an individual with around 40 repetitions is likely to get their first symptoms in late middle age. However, a person with 36 to 39 CAG repeats may or may not develop the signs and symptoms of Huntington disease. The increase in the size of the CAG segment of 40 or more CAG segments leads to the production of an abnormally long version of the huntingtin protein. This elongated protein is cut into smaller, toxic fragments that bind together and accumulate in neurons, disrupting the normal functions of these cells. The dysfunction and eventual death of neurons in certain areas of the brain cause the signs and symptoms of Huntington disease. Amniocentesis may be used to detect this genetic disorder.

A fetus of a patient is determined by prenatal genetic testing to have a mutation in the HTT gene. The present in utero gene editing is used to target the mutated HTT gene in the fetus and base editing this HTT gene to correct the mutation, thereby allowing the HTT gene to encode the huntingtin of a length that has less than 40 CAG repetitions. Postnatally, the infant has no abnormality in the HTT gene and does not exhibit any phenotypes associated with HTT mutation, thereby blocking the development of HD in the treated subject.

3-beta-hydroxysteroid Dehydrogenase Deficiency 3-beta (β)-hydroxysteroid dehydrogenase (HSD) deficiency is an inherited disorder that affects hormone-producing glands including the gonads, i.e., ovaries in females and testes in males, and the adrenal glands. The HSD3B2 gene encodes the 3β-HSD enzyme, which is involved in the production of many hormones, including cortisol, aldosterone, androgens, and estrogen; the 3β-HSD enzyme is found in the gonads and adrenal gland. Mutations in the hydroxy-delta-5-steroid dehydrogenase, 3 beta- and steroid delta-isomerase 2 (HSD3B2) gene cause 3β-HSD deficiency. Individuals with 3β-HSD deficiency lack many of the hormones that are made in these glands, and the deficiency impairs hormone production and disrupts sexual development and maturation.

A fetus of a patient is determined by prenatal genetic testing to have a mutation in the HSD3B2 gene. The present in utero gene editing is used to target the mutated HSD3B2 gene in the fetus and base editing this HSD3B2 gene to correct the mutation, thereby allowing the HSD3B2 gene to encode the 3β-HSD enzyme. Postnatally, the infant has no abnormality in the HSD3B2 gene and does not exhibit any phenotypes associated with HSD deficiency.

GJB2 Hearing Impairment

A single nucleotide that changes a codon to an amino acid with similar properties, i.e., M34T and V37I variants of the gap junction protein beta 2 (GJB2) gene, results in hearing loss or impairment. The GJB2 gene encodes a protein called gap junction beta 2, more commonly known as connexin 26 is found in cells throughout the body, including the inner ear.

Because of its presence in the inner ear, especially the snail-shaped structure called the cochlea, this protein may have a role in hearing. Hearing requires the conversion of sound waves to electrical nerve impulses, which involves many processes, including maintenance of a proper level of potassium ions in the inner ear. Some studies indicate that channels made with connexin 26 help to maintain the correct level of potassium ions. Other research suggests that connexin 26 is required for the maturation of certain cells in the cochlea. Connexin 26 also is present in the skin, where it is thought to play a role in the growth, maturation, and stability of the skin's outermost layer, the epidermis. At least one GJB2 gene mutation has been identified in people with *hystrix*-like ichthyosis with deafness (HID), which is characterized by dry, scaly skin (ichthyosis) and hearing loss that is typically profound. This mutation replaces the amino acid aspartic acid with the amino acid asparagine at protein position 50, i.e., Asp50Asn or D50N. Mutation analysis of the GJB2 gene is widely available as a genetic diagnostic test.

A fetus of a patient is genetic testing prenatally and is found to have a mutation in the GJB2 gene. The present in utero gene editing is used to target the mutated GJB2 gene in the fetus and base editing this GJB2 gene to correct the mutation, thereby allowing the GJB2 gene to encode the gap junction beta 2 protein. Postnatally, the infant has no abnormality in the GJB2 gene and does not exhibit any phenotypes associated with GJB2 deficiency, i.e., hearing impairment or HID.

Human Immunodeficiency Virus (HIV)

The human immunodeficiency virus (HIV) destroys immune cells called T-cells by exploiting the C-C motif chemokine receptor 5 (CCR5) on the surface of T cells. The CCR5 gene encodes a member of the beta chemokine receptor family, which is predicted to be a seven transmembrane protein similar to G protein-coupled receptors. This protein is expressed by T cells and macrophages, and is known to be an important co-receptor for macrophage-tropic virus, including HIV, to enter host cells. Whereas defective alleles of the CCR5 gene have been associated with the HIV infection resistance. Many people who are resistant to HIV have a mutation in the CCR5 gene called CCR5-delta32. The CCR5-delta32 mutation results in a smaller protein that is not present on the outside of the cell. Most forms of HIV cannot infect cells if there is no CCR5 on the surface.

The present in utero gene editing is used to target the CCR5 gene in the fetus of a patient infected with HIV and a defect (mutation) is introduced into CCR5 gene, for example in stem cells that give rise to T cells a nonsense codon is introduced by base pair editing, thereby blocking HIV infection. Postnatally, the infant has an abnormality in the CCR5 gene, and does not exhibit any phenotypes associated with infection by HIV.

Marfan Syndrome

The fibrillin 1 (FBN1) gene encodes a large protein called fibrillin-1. Molecules of fibrillin-1 bind to each other and to other proteins to form threadlike filaments called microfibrils; microfibrils form elastic fibers, which enable the skin, ligaments, and blood vessels to stretch. Microfibrils also provide support to more rigid tissues, such as bones, ligaments, muscles, blood vessels, and heart valves, and the tissues that support the nerves, muscles, and lenses of the eyes. In addition, microfibrils store a protein called transforming growth factor beta (TGF-$\beta$), a critical growth factor.

Mutations in the FBN1 gene cause Marfan syndrome, which is characterized by a reduced amount of functional fibrillin-1 that is available to form microfibrils, leading to decreased microfibril formation. As a result, excess growth factors are released (since the reduced amount microfibrils cannot store them), and elasticity in many tissues is decreased, leading to overgrowth and instability of tissues. Marfan syndrome is inherited in an autosomal dominant pattern, i.e., one copy of the altered gene in each cell is sufficient to cause the disorder. Marfan syndrome has an incidence of at least 1:10 000 and about 25-30% of cases represent new mutations. No particular genetic hot spots are implicated in this disorder, since mutations are found throughout the entire fibrillin-1 gene; however, a clustering of mutations associated with the most severe form of Marfan syndrome, neonatal Marfan (nMFS) syndrome, has been identified in a region encompassing exons 24 to 32, and using strict clinical definition of nMFS, there is a clustering of mutations in exons 24-27, where missense mutations as well as small deletions and one exon skipping mutation have been detected in nMFS patients, as well as exon skipping mutations in exons 31-32.

The present in utero gene editing is used to target mutation(s) in the FBN1 gene in the fetus of a patient, and genome editing by base editing corrects mutations, such as missense mutations and/or deletions exons 24 to 32, and in particular, the mutation in exons 24-27. Postnatally, the infant presents no abnormalities in the FBN1 gene, and does not exhibit any phenotypes associated with lack of fibrillin-1 and/or defective storage of TGF-$\beta$.

Fragile X Syndrome

The fragile X mental retardation 1 (FMR1) gene encodes a protein called FMRP. FMRP is present in many tissues, including the brain, testes, and ovaries; in the brain, it may play a role in the development of connections between nerve cells, i.e., synapses, where cell-to-cell communication occurs. It is thought that FMRP acts as a shuttle within cells by transporting molecules called messenger RNA (mRNA).

Mutations in the FMR1 gene cause fragile X syndrome. Almost all FMR1 mutations are caused by a mutation in which a DNA segment, known as the CGG triplet repeat, is expanded within the FMR1 gene. Normally, the CGG triplet repeat is repeated from 5 to about 40 times. However, in individuals with fragile X syndrome, the CGG segment is repeated more than 200 times. The abnormally expanded CGG segment turns off (silences) the FMR1 gene, thus preventing the gene from producing FMRP. A deficiency of this protein disrupts nervous system functions and leads to the symptoms of fragile X syndrome.

The presently provided utero gene editing method is used to target mutations in the FMR1 gene in the fetus of a patient, and genome editing by base editing corrects mutations, such as deleting the excessive repetition of the CGG triplet to turn on the FMR1 gene. Postnatally, the infant does not exhibit symptoms of fragile X syndrome, and the FMR1 gene does not comprise more than 200 repeats of the CGG segment.

Pre-Implantation Genetic Diagnosis (PGD) and in Utero Genomic Editing

Embryos can be screened using pre-implantation genetic diagnosis (PGD) for patients undergoing in vitro fertilization (IVF). The main candidates for PGD are couples with a family history of X-linked disorders; these couples have a 25% risk of having an affected embryo (half of male embryos); couples with chromosome translocations, which can cause implantation failure, recurrent pregnancy loss, or mental or physical problems in offspring; carriers of autosomal recessive diseases, for these carriers the risk an embryo may be affected is 25%; carriers of autosomal dominant diseases, for these carriers, the risk an embryo may be affected is 50%; women of advanced maternal age; couples with a history of recurrent pregnancy loss or with repeated IVF failure a male partner with severe male factor infertility.

PGD is used to identify single gene defects such as cystic fibrosis, Tay-Sachs disease, sickle cell anemia, and Huntington disease. In such diseases, the abnormality is detectable with techniques using polymerase chain reaction (PCR) amplification of DNA from a single cell. While progress has been made, some single gene defects, such as cystic fibrosis, have multiple known mutations. In cystic fibrosis, only 25 mutations are currently routinely tested. Because most of these rare mutations are not routinely tested, a parent without any clinical manifestations of cystic fibrosis could still be a carrier; consequently, the possibility exists for a parent carrying a rare mutation gene to be tested as "negative", but still have the ability to pass on the mutant cystic fibrosis gene. PGD can also be used to identify genetic mutations like BRCA–1, which does not cause a specific disease but increases the risk of a set of diseases.

The presently provided genome editing methods may be used after a pre-implantation genetic diagnosis of an embryo, including but not limited to any of the genetic defects discussed above, e.g., single gene defects, sex-linked recessive disorders include hemophilia, fragile X syndrome, most neuromuscular dystrophies (currently, >900 neuromuscular dystrophies are known), and hundreds of other diseases. Sex-linked dominant disorders include Rett syndrome, incontinentia pigmenti, pseudohyperparathyroidism, and vitamin D-resistant rickets. Another disease for which the genome editing methods provided herein, may be utilized includes an X-linked recessive disease called Wiskott-Aldrich syndrome (WAS), caused by mutation in the Wiskott-Aldrich syndrome (WAS) gene, a gene defect that affects many immune cells, including B cells, T cells and platelets.

Any patent, patent application publication, or scientific publication, cited herein, is incorporated by reference herein in its entirety.

The examples are presented in order to more fully illustrate embodiments of the invention. They should in no way be construed, however, as limiting the broad scope of the invention.

While certain features of the invention have been described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method for in utero genome editing in a fetal subject in need thereof, the method comprising:
   (a) administering to the fetal subject, a pharmaceutical composition comprising at least one of
      i) a lipid nanoparticle delivery vehicle;
      ii) an adenovirus (AV) vector; or
      iii) an adeno-associated virus (AAV) vector,
   wherein at least one of i), ii) or iii) comprise nucleic acids encoding a CRISPR-mediated base editor 3 (BE3) or base editor 4 (BE4) and a guide RNA (gRNA) comprising a protospacer adjacent motif (PAM), which upon expression in said subject, form a CRISPR complex at a target site present in a 4-hydroxyphenylpyruvate dioxygenase (Hpd) gene; and
   (b) introducing a modified codon at said target site in the Hpd gene by CRISPR complex mediated base editing for reducing Hpd expression, thereby treating, or reducing the risk of, hereditary tyrosinemia type I (HT1) disorder in said fetal subject, wherein said gRNA includes the nucleotide sequence of SEQ ID NO: 36, 5'-CATTCAACGTCACAACCACC-3', an AGG PAM sequence and the editing is a C to T change on a sense strand encoding the Hpd gene at a mean editing rate of ~15%.

2. The method of claim 1, further comprising before step (a):
   (i) identifying a target codon for base editing into a nonsense codon; and
   (ii) generating the adenoviral vector by cloning BE3-encoding gene, a synthetic polyadenylation sequence from pCMV-BE3, CAG reporter from pCas9_GFP, and U6 promoter-driven gRNA cassette with a protospacer sequence into a dual-expression vector.

3. The method of claim 2, wherein the target codon is screened for a glutamine residue and a tryptophan residue, wherein the glutamine and tryptophan residues are within a base editing window of a protospacer adjacent motif (PAM) of the BE3, wherein the window is flanked by four proximal and four distal bases, wherein the proximal and distal bases match reference sequences.

4. The method of claim 3, further comprising assessing C bases within the window for a change to another base, wherein
   a) the change is via a C to T or G to A on sense strand, and the modified codon is changed to a nonsense codon, or
   b) the change is via a C to T or G to A on an antisense strand, and the modified codon is changed to a nonsense codon.

5. The method of claim 4, wherein the BE3 PAM sequence (NGG) in selected gRNAs is 13-17 nucleotides distal to the target cytosine base(s).

6. The method of claim 1, wherein the base editing occurs prior to onset of said disorder and said pharmaceutical composition is administered via injection into a vein in a human fetus.

7. The method of claim 6, wherein the base editing occurs in the liver of said fetal subject, wherein the fetal subject is inside a uterus of a body of a living carrier.

8. The method of claim 1, wherein the base editing decreases a risk of developing said disorder.

9. The method of claim 6, wherein the modified codon is a nonsense codon in the Hpd gene which knocks out Hpd gene function.

10. The method of claim 9, wherein loss of Hpd function restores normal liver function in the subject prior to birth or treats hereditary tyrosinemia type I (HT1) disorder in the subject prior to birth.

11. The method of claim 1, wherein said vector is an adeno-associated vector.

12. The method of claim 1, wherein said CRISPR-mediated base editor 3 (BE3) and a guide RNA (gRNA) are delivered on a lipid based nanoparticle.

13. The method of claim 1, wherein a combination of lipid-based nanoparticles and an AV vector are administered.

14. The method of claim 1, wherein a combination of lipid-based nanoparticles and an AAV vector are administered.

15. The method of claim 1, wherein said AAV vector is AAV8 or AAV9.

16. The method of claim 1, wherein said CRISPR-mediated base editor 4 (BE4) and a guide RNA (gRNA) are delivered on a lipid based nanoparticle.

* * * * *